US009650630B2

(12) United States Patent
Otte et al.

(10) Patent No.: US 9,650,630 B2
(45) Date of Patent: May 16, 2017

(54) NUCLEIC ACID FRAGMENTS FROM A RIBOSOMAL PROTEIN PROMOTER FOR ENHANCING GENE EXPRESSION

(75) Inventors: Arie Pieter Otte, Amersfoort (NL); Femke Hoeksema, Duivendrecht (NL); John Antonius Verhees, Wageningen (NL); Henricus Johannes Maria Van Blokland, Wijde Wormer (NL)

(73) Assignee: CellaGenics B.V., Amsterdam (NL)

( * ) Notice: Subject to any disclaimer, the term of this patent is extended or adjusted under 35 U.S.C. 154(b) by 0 days.

(21) Appl. No.: 13/820,083

(22) PCT Filed: Aug. 31, 2011

(86) PCT No.: PCT/NL2011/050593
§ 371 (c)(1),
(2), (4) Date: May 13, 2013

(87) PCT Pub. No.: WO2012/030218
PCT Pub. Date: Mar. 8, 2012

(65) Prior Publication Data
US 2013/0236956 A1    Sep. 12, 2013

Related U.S. Application Data

(60) Provisional application No. 61/379,025, filed on Sep. 1, 2010.

(51) Int. Cl.
| | | |
|---|---|---|
| *C12N 15/113* | (2010.01) | |
| *C07K 14/47* | (2006.01) | |
| *C12N 15/85* | (2006.01) | |
| *C12N 15/10* | (2006.01) | |

(52) U.S. Cl.
CPC ............ *C12N 15/113* (2013.01); *C07K 14/47* (2013.01); *C12N 15/1086* (2013.01); *C12N 15/85* (2013.01)

(58) Field of Classification Search
None
See application file for complete search history.

(56) References Cited

U.S. PATENT DOCUMENTS

| | | | |
|---|---|---|---|
| 4,965,196 A | 10/1990 | Levinson et al. | |
| 6,110,707 A | 8/2000 | Newgard et al. | |
| 6,165,715 A | 12/2000 | Collins et al. | |
| 7,041,483 B2 | 5/2006 | Rothnagel et al. | |
| 2002/0019049 A1 | 2/2002 | Lok | |
| 2006/0172382 A1 | 8/2006 | Otte et al. | |
| 2008/0286824 A1 | 11/2008 | Dupraz et al. | |

FOREIGN PATENT DOCUMENTS

| | | |
|---|---|---|
| WO | WO-01/32901 A1 | 5/2001 |
| WO | WO-03/004704 A2 | 1/2003 |
| WO | WO-03/106674 A2 | 12/2003 |
| WO | WO-03/106684 A2 | 12/2003 |
| WO | WO-2006/005718 A2 | 1/2006 |
| WO | WO-2006/048459 A2 | 5/2006 |
| WO | WO-2006/123097 A2 | 11/2006 |
| WO | WO-2007/096399 A2 | 8/2007 |
| WO | WO-2010/147462 A2 | 12/2010 |

OTHER PUBLICATIONS

Genbank Accession AC018843.4, 2001, accessed on Apr. 19, 2014: http://www.ncbi.nlm.nih.gov/nucleotide/13899386?report=genbank&log$=nuclalign&blast_rank=1&RID=N59Y1JJS01R.*
Kozak, Gene, 2005, vol. 361, pp. 13-37.*
McCormick et al., Molecular and Cellular Biology, 1984, vol. 4, pp. 166-172.*
Kozak. Constraints on reinitation of translation in mammals. Nucleic Acids Research, vol. 29, No. 24, pp. 5226-5232, 2001.
US Office Action on U.S. Appl. No. 13/378,006 DTD Jun. 10, 2013.
US Office Action on U.S. Appl. No. 13/378,006 DTD Sep. 10, 2013.
Fan, et al. "Development of a highly-efficient CHO cell line generation system with engineered SV40E promoter", Journal of Biotechnology, 2013, vol. 168, pp. 652-658.
Kane, et al. "MDR1 bicistronic vectors: analysis of selection stringency, amplified gene expression, and vector stability in cell lines", Biochemical Pharmacology, 2001, vol. 62, pp. 693-704.
Yan, et al. "A mini-IRES sequence for stringent selection of high producers", J. Biosci., Jun. 2013, vol. 38, No. 2, pp. 245-249.
Bergdoll, et al., "All in the family: Structural and evolutionary relationships among three modular proteins with diverse functions and variable assembly", Protein Science, (1998), vol. 7, pp. 1661-1670, XP002596221.
Dumas, et al., "Crystal structure and site-directed mutagenesis of a bleomycin resistance protein and their significance for drug sequestering," The European Molecular Biology Organization (EMBO) Journal, (1994) vol. 13, No. 11, pp. 2483-2492, XP002596206.
International Search Report in PCT/NL2010/050367 dated Mar. 10, 2011.
Levine, et al., "Efficient gene expression in mammalian cells from a dicistronic transcriptional unit in an improved retroviral vector," Gene, (1991), vol. 108, pp. 167-174, XP0023541477.
Mulsant, et al., "Phleomycin Resistance as a Dominant Selectable Marker in CHO Cells," Somatic Cell and Molecular Genetics, (1988), vol. 14, No. 3, pp. 243-252, XP009137462.

(Continued)

*Primary Examiner* — Anne Gussow
*Assistant Examiner* — Mindy G Brown
(74) *Attorney, Agent, or Firm* — Gilberto M. Villacorta; Sunit Talapatra; Foley & Lardner LLP

(57) ABSTRACT

The present invention relates to nucleic acid fragments and constructs comprising genomic nucleotide sequences from the promoter region of a 60S ribosomal protein L32 gene (RPL32), for the production of a gene product of interest in a eukaryotic, preferably mammalian, host cell in the presence of a stringent selectable marker. The invention further relates to host cells comprising the nucleic acid constructs, to methods for generating the host cells and to methods for producing a gene product of interest using the host cells.

21 Claims, 10 Drawing Sheets

(56) References Cited

OTHER PUBLICATIONS

Needham et al., "Further Development of the Locus Control Region/Murine Erythroleukemia Expression System: High Level Expression and Characterization of Recombinant Human Calcitonin Receptor", 1995, Protein Expression and Purification, vol. 6, pp. 124-131.

Otte et al, "Various Expression—Augmenting DNA Elements Benefit from STAR-Select, a Novel High Stringency Selection System for Protein Expression", 2007, Biotechnol. Prog., vol. 23, pp. 801-807.

Rees et al., "Bicistronic Vector for the Creation of Stable Mammalian Cell Lines that Predisposes All Antibiotic-Resistant Cells to Express Recombinant Protein", Jan. 1996, BioTechniques, vol. 20, pp. 102-110.

Van Blokland, et al., "A novel, high stringency selection system allows screening of few clones for high protein expression," (2007), vol. 128, pp. 237-245, XP005829332.

Database EMBL [Online] Dec. 19, 2011 (Dec. 19, 2011), "*Homo sapiens* RPL32 gene for ribosomal protein L32, complete cds and sequence.", XP002663329, retrieved from EBI accession No. EM_HUM:AB061831.

Database EMBL [online] Apr. 7, 2000 (Apr. 7, 2000), "*Homo sapiens* chromosome 3 clone RP11-767C1 map 3p, complete sequence.", XP002663328, retrieved from EBI accession No. EM_HUM:AC034198.

Hoeksema, F. et al: "Placing the RPL32 Promoter Upstream of a Second Promoter Results in a Strongly Increased Number of Stably Transfected Mammalian Cell Lines That Display High Protein Expression Levels", Biotechnology Research International, vol. 2011, 492875, Dec. 19, 2010 (Dec. 19, 2010), XP002663330.

International Search Report for PCT/NL2011/050593—mailed Nov. 29, 2011.

Perry, Robert P.: "The architecture of mammalian ribosomal protein promoters", BMC Evolutionary Biology, vol. 5, No. 15, Feb. 13, 2005 (Feb. 13, 2005), pp. 1-16, XP002601726, Biomed Central Ltd., London, GB.

Yoshihama, Maki et al: "The Human Ribosomal Protein Genes: Sequencing and Comparative Analysis of 73 Genes", Genome Research, vol. 12, No. 3, Mar. 1, 2002 (Mar. 1, 2002), pp. 379-390, XP002516388, Cold Spring Harbor Laboratory Press, Woodbury, NY, US.

Yoshihama et al., "The human ribosomal protein genes: sequencing and comparative analysis of 73 genes." Genome Research, 2002, vol. 12, No. 3, pp. 379-390.

\* cited by examiner

Fig 1
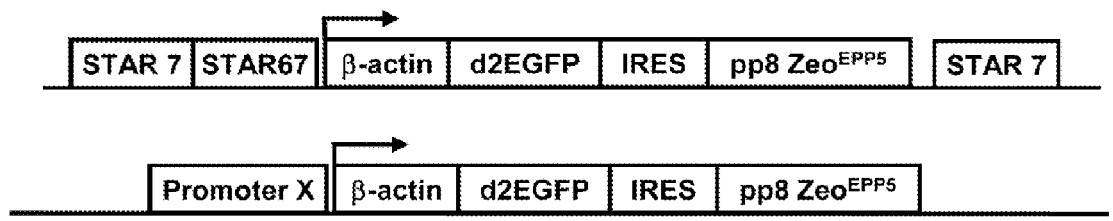
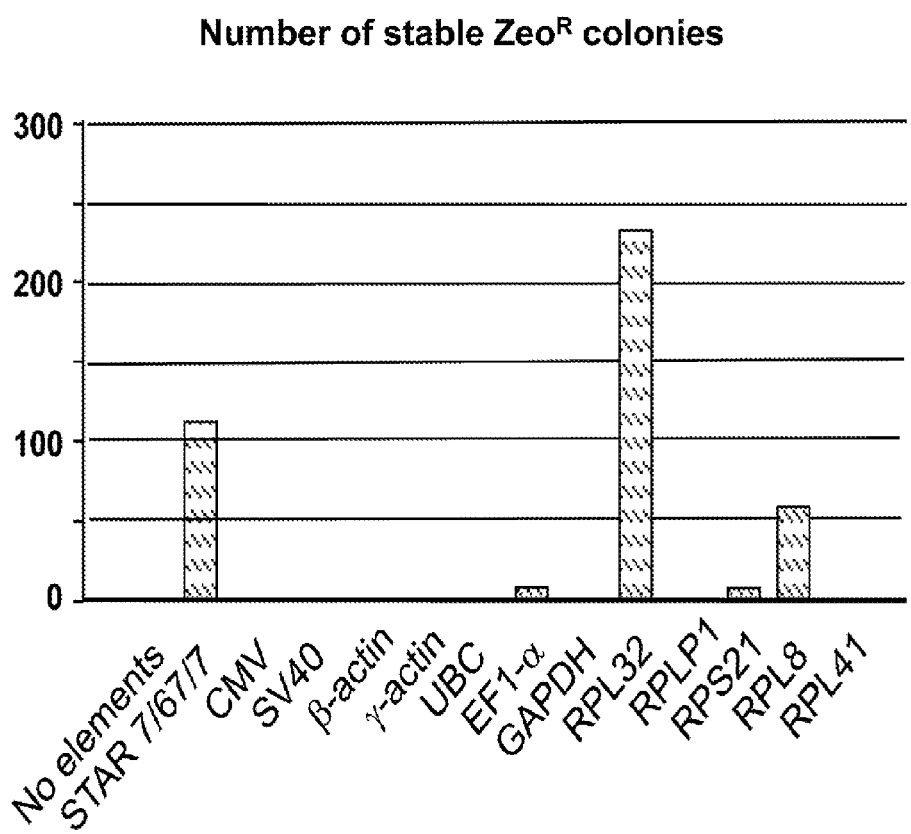

Fig 2
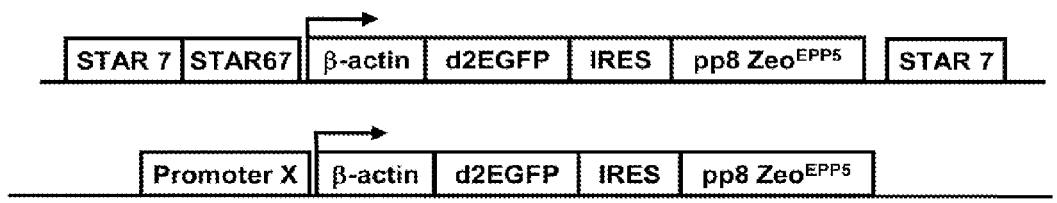
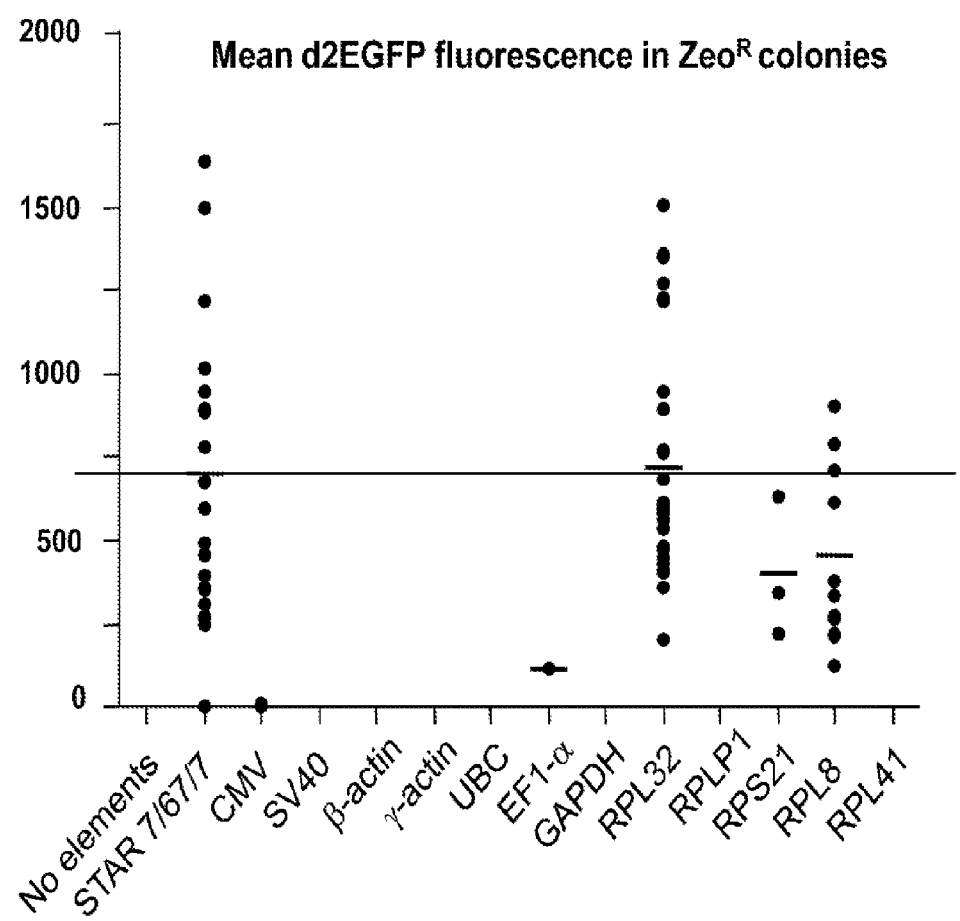

SEQUENCE LISTING

```
<160> NUMBER OF SEQ ID NOS: 47

<210> SEQ ID NO 1
<211> LENGTH: 3220
<212> TYPE: DNA
<213> ORGANISM: Homo sapiens
<220> FEATURE:
<221> NAME/KEY: Start_trancription
```

<222> LOCATION: (1921)..(1921)

<400> SEQUENCE: 1

```
cttggcattg acttagacac cctaggaatc taacttgaga aaatgttttc attaaaaaaa      60
atctcaggaa gtaaaacctc ctgaatgatt actgagttga cataaatctt atgtgtatat     120
tcttatcaga aaaaaagtat cttcattttg tgggacacca attcatgtat tattattatt     180
ttgagacaaa gtttcgctct tgttgcccag gctggagtgc aatggcgcga tctccactta     240
ctgcaacctc cacctcctga gttcaagtga ttctcgtgcc tcagcctccc tagtagctgg     300
aactacaggc atgtgccacc acacccagct aatttttgt aactttagta gagatggggt      360
ttcaccatgt tggccaggat ggactcgaac tcctgaccac aggtgatctg cccacctcag     420
cttcccaaag tgctgggatt acaggcatga gccaccgcgc ccagtcgctg gtcttacag      480
taactttatg tttaacattt tgaggaaatg ctattctttt ccaaagtgac tgcaccattt     540
catatttgca ctagcactgt acggacattc ccatttctct gtcctagtga gtgtgaaatg     600
gtatctcact gcagttccag tttgtatttc cctgatggct aatgatgtgg atcatttcat     660
gtgttcattg ccacagaga aatgtctatt tggattcttt acccattttt caattgggtt      720
atttgtcttt ataggtttgt tgttgttgag acagagtctt gctctgtcac tcaggctgga     780
gtgcagtggc attatcacag ctaactgcag tctagaactg ctgggctcac gtgatcatcc     840
cagctcagcc tctcgagtaa ctgggactac aggcatgcgc caccagcccc agctaattat     900
tttatttttt gtagagacag ggtcttacta tgttgcctag gccggtcttg aactcctggg     960
ctcaagcaaa tctcccacct cagactccca agtattgga attataggtg tgaaccatag     1020
tgctcagcca atttgcacaa taatcttaaa tacaaaagct aagcaaaaca aatcaagagc    1080
atctttaaaa actaggcagt ctgggaggca ggggctgccg tgagccgtga gatggcacct    1140
ttgcattcca gcctaggtga cagagggagg ccctgtctaa aaaaaaccaa aaaccaaaaa    1200
acaaaacaaa acaaaaaaca tctaggcagt agctcgtgcc cgtaatccca gctactcagg    1260
aggctgaggc gagagaatcg tttgagccca ggagttcaag accagcctgg caacagagt     1320
gagacccccat ttctaaaaaa tgaacaaaga aaaactaggc agtttcgccc agtggttaga    1380
agcgtggagt ttggagtcaa gtctccaaat ttcatcttcc acatatgcaa aatggagaca    1440
ataatagggg tacgttatag aattgtggta ggcatagtga actccatcgc atgttagctg    1500
ttttcgttac tatttactgt ctaaattcgg tgatgaaatt attaggaagt ctctgtcttg    1560
ttctcttctg accactaaga ggcgcacttc ggagtagaag aaacgcgggc ggaaatagcc    1620
caaaagcgga ttggcttcga cttctggcgg aagtaaattc ctccctccac caggtcttat    1680
tagctcagaa agaattccaa atttctacgt agtcccaagg ataggtagaa tacatttctc    1740
agtcctattc ctagttatta ttgtctatta aaacatgtat actcagaatt tttgcggcat    1800
tattttttga cgtgtcttta ttttatttaa aagagccgga gccggaagtg cttgcctttt    1860
tccctgctag gacccagggg ttacgaccca tcagcccttg cgcgccaccg tcccttctct    1920
cttcctcggc gctgcctacg gaggtggcag ccatctcctt ctcggtaagt gttaatccgt    1980
ggcaatccgc attcctgcgg gattcatctg gccccgtcgc ccagtggtgc ggaggcctcc    2040
ccttcagcgc ggtagtgtct gtgggtattg ttattgtcag cttactggag cgtgtacagg    2100
aacagaacga agccgccgag ttgataggc tttgcgtccc agagcctcct gccctccgcc     2160
tgtattcaga gctgcgggct gcttgttgt tccttggcgg tggagggtgc tagttgaggc     2220
cagacttcgg ggtctcctgg gggccgtggg acgaccaggg gtggcccagc ttgacagctt    2280
```

```
tcagctggga tctgtggatc ccagcgctca ccaatgtcgg cccacgtgta ttcgttcatg    2340
ccatggccgg cttcttccgc tgcagtctct ggcccgaggg ctgctgctgc gggaccgcca    2400
aggaaagacg agctgtaggt cggctggtcc agctgcaggc agaaattctg gtagtatctc    2460
tgggaatatg aagatgcaac tgcccccacc ttgccttcga ggatatcatg ggccagaagg    2520
cagagtcgtt ttgaatacgt ggttcattga gtacccactc tgggccagtt gatggctgcg    2580
aagagagcag aaggggtgct gctgtaggaa atcaatggct cggaagacca cactgaggaa    2640
ggtgtgagtt gatactggaa gatctccagg tttgaggcat cttcagaggt atatggtggt    2700
tttgtgtgtg ttgagggtgt ggtagcgcag cagctcccta gggaattaga aggttttatt    2760
gaacatttac cctgtgacag gcactgcagg cattcagcgc gcagtgtcat cttcatttta    2820
caggtgagga aaagactcag gttcaagtag atggtcaagg ccagtactac cggaaggacc    2880
atctgggggt tcggacactg gtggggtggg atttgctgcc ccttgcaaat tgagagtgtc    2940
ttggggtcag ttttgatttg ctcagctgtt ggcattcttt gggctctgag tgggtgaggt    3000
gacccttgac ctcctgggat cgcatctgga gagtgcctag tattctgcca gcttcggaaa    3060
gggagggaaa gcaagcctgg cagaggcacc cattccattc ccagcttgct ccgtagctgg    3120
cgattggaag acactctgcg acagtgttca gtccctgggc aggaaagcct ccttccagga    3180
ttcttcctca cctggggccg cttcttcccc aaaaggcatc                          3220

<210> SEQ ID NO 2
<211> LENGTH: 7927
<212> TYPE: DNA
<213> ORGANISM: Artificial
<220> FEATURE:
<223> OTHER INFORMATION: ppZeo expression cassette of Example 1

<400> SEQUENCE: 2
tgggtcctat gattatgtcc ggttaaggat ccaccatggc caagttgacc agtgccgttc      60
cggtgctcac cgcgcgcgac gtcgcaggag cggtcgggtt ctggaccgac cggctcgggt     120
tctcccggga cttcgtggag gacgacttcg ccggtgtggt ccgggacgac gtgaccctgt     180
tcatcagcgc ggtccaggac caggtggtgc cggacaacac cctggcctgg gtgtgtgtgc     240
gcggcctgga cgagctgtac accgagtggt cggaggtcgt gtccacgaac ttccgggacg     300
cctccgggcc ggccatgacc gagatcgcg agcagccgtg ggggcgggag ttcgccctgc     360
gcgacccggc cggcaactgc gtgcacttcg tggccgagga gcaggactga attcgcggcc     420
gcttcccttt agtgagggtt aatgcttcga gcagacatga taagatacat tgatgagttt     480
ggacaaacca caactagaat gcagtgaaaa aaatgcttta tttgtgaaat ttgtgatgct     540
attgctttat ttgtaaccat tataagctgc aataaacaag ttaacaacaa caattgcatt     600 catttatgt ttcaggttca ggggggagatg tgggaggttt tttaaagcaa gtaaaacctc     660
tacaaatgtg gtaaaatccg ataaggatcg atccgggctg cgtaatagc gaagaggccc     720 gcaccgatcg ccccttccca cagttgccct actagtcggc cgtacgatcg acaccgctag    780
cattaccctg ttatccctac tcgacctgca ggcatgcaag cttggcgtaa tcatggtcat     840
agctgtttcc tgtgtgaaat tgttatccgc tcacaattcc acacaacata cgagccggaa    900
gcataaagtg taaagcctgg ggtgcctaat gagtgagcta actcacatta attgcgttgc     960
gctcactgcc cgctttccag tcgggaaacc tgtcgtgcca gctgcattaa tgaatcggcc    1020
aacgcgcggg gagaggcggt ttgcgtattg ggcgctcttc cgcttcctcg ctcactgact    1080
```

```
cgctgcgctc ggtcgttcgg ctgcggcgag cggtatcagc tcactcaaag gcggtaatac      1140
ggttatccac agaatcaggg gataacgcag gaaagaacat gtgagcaaaa ggccagcaaa      1200
aggccaggaa ccgtaaaaag gccgcgttgc tggcgttttt ccataggctc cgcccccctg      1260
acgagcatca caaaaatcga cgctcaagtc agaggtggcg aaacccgaca ggactataaa      1320
gataccaggc gtttccccct ggaagctccc tcgtgcgctc tcctgttccg accctgccgc      1380
ttaccggata cctgtccgcc tttctccctt cgggaagcgt ggcgctttct catagctcac      1440
gctgtaggta tctcagttcg gtgtaggtcg ttcgctccaa gctgggctgt gtgcacgaac      1500 ccccgttca gcccgaccgc tgcgccttat ccggtaacta tcgtcttgag tccaacccgg      1560
taagacacga cttatcgcca ctggcagcag ccactggtaa caggattagc agagcgaggt      1620
atgtaggcgg tgctacagag ttcttgaagt ggtggcctaa ctacggctac actagaagga      1680
cagtatttgg tatctgcgct ctgctgaagc cagttacctt cggaaaaaga gttggtagct      1740
cttgatccgg caaacaaacc accgctggta gcggtggttt ttttgtttgc aagcagcaga      1800
ttacgcgcag aaaaaaagga tctcaagaag atcctttgat cttttctacg ggtctgacg      1860 ctcagtggaa cgaaaactca cgttaaggga ttttggtcat gagattatca aaaaggatct      1920
tcacctagat ccttttaaat taaaaatgaa gttttaaatc aatctaaagt atatatgagt      1980
aaacttggtc tgacagttac caatgcttaa tcagtgaggc acctatctca gcgatctgtc      2040
tatttcgttc atccatagtt gcctgactcc ccgtcgtgta gataactacg atacgggagg      2100
gcttaccatc tggccccagt gctgcaatga taccgcgaga cccacgctca ccggctccag      2160
atttatcagc aataaaccag ccagccggaa gggccgagcg cagaagtggt cctgcaactt      2220
tatccgcctc catccagtct attaattgtt gccgggaagc tagagtaagt agttcgccag      2280
ttaatagttt gcgcaacgtt gttgccattg ctacaggcat cgtggtgtca cgctcgtcgt      2340
ttggtatggc ttcattcagc tccggttccc aacgatcaag gcgagttaca tgatccccca      2400
tgttgtgcaa aaaagcggtt agctccttcg gtcctccgat cgttgtcaga agtaagttgg      2460
ccgcagtgtt atcactcatg gttatggcag cactgcataa ttctcttact gtcatgccat      2520
ccgtaagatg cttttctgtg actggtgagt actcaaccaa gtcattctga atagtgta      2580 tgcggcgacc gagttgctct tgcccggcgt caatacggga taataccgcg ccacatagca      2640
gaactttaaa agtgctcatc attggaaaac gttcttcggg gcgaaaactc tcaaggatct      2700
taccgctgtt gagatccagt tcgatgtaac ccactcgtgc acccaactga tcttcagcat      2760
cttttacttt caccagcgtt tctgggtgag caaaaacagg aaggcaaaat gccgcaaaaa      2820
agggaataag ggcgacacgg aaatgttgaa tactcatact cttccttttt caatattatt      2880
gaagcattta tcagggttat tgtctcatga gcggatacat atttgaatgt atttagaaaa      2940
ataaacaaat aggggttccg cgcacatttc cccgaaaagt gccacctgac gtctaagaaa      3000
ccattattat catgacatta acctataaaa ataggcgtat cacgaggccc ttaaggccgc      3060
ctgatgcggt attttctcct tacgcatctg tgcggtattt cacaccgcat atggtgcact      3120
ctcagtacaa tctgctctga tgccgcatag ttaagccagc cccgacaccc gccaacaccc      3180
gctgacgcgc cctgacgggc ttgtctgctc ccggcatccg cttacagaca agctgtgacc      3240
gtctccggga gctgcatgtg tcagaggttt tcaccgtcat caccgaaacg cgcgagacga      3300
aagggcccgt accttaatta agatctgat aattcctttg cctaattttc gagttctata      3360
gtgtcgcggc gctatggta ccggcgcgcc gggccagata tacgcgtcct gcagctgaaa      3420
gatacaaggc cagggacagg acagtcccat ccccaggagg cagggagtat acaggctggg      3480
```

| | |
|---|---|
| gaagtttgcc cttgcgtggg gtggtgatgg aggaggctca gcaagtcttc tggactgtga | 3540 |
| acctgtgtct gccactgtgt gctgggtggt ggtcatcttt cccaccaggc tgtggcctct | 3600 |
| gcaaccttca agggaggagc aggtcccatt ggctgagcac agccttgtac cgtgaactgg | 3660 |
| aacaagcagc ctccttcctg ccacaggtt ccatgtcctt atatggactc atctttgcct | 3720 |
| attgcgacac acactcagtg aacacctact acgcgctgca aagagccccg caggcctgag | 3780 |
| gtgccccac ctcaccactc ttcctatttt tgtgtaaaaa tccagcttct tgtcaccacc | 3840 |
| tccaaggagg gggaggagga ggaaggcagg ttcctctagg ctgagccgaa tgccctctg | 3900 |
| tggtcccacg ccactgatcg ctgcatgccc accacctggg tacacacagt ctgtgattcc | 3960 |
| cggagcagaa cggaccctgc ccacccgtc ttgtgtgcta ctcagtggac agacccaagg | 4020 |
| caagaaaggg tgacaaggac agggtcttcc caggctggct ttgagttcct agcaccgccc | 4080 |
| cgcccccaat cctctgtggc acatggagtc ttggtcccca gagtccccca gcggcctcca | 4140 |
| gatggtctgg gagggcagtt cagctgtggc tgcgcatagc agacatacaa cggacggtgg | 4200 |
| gcccagaccc aggctgtgta gacccagccc ccccgccccg cagtgcctag gtcacccact | 4260 |
| aacgccccag gccttgtctt ggctgggcgt gactgttacc ctcaaaagca ggcagctcca | 4320 |
| gggtaaaagg tgccctgccc tgtagagccc accttccttc ccagggctgc ggctgggtag | 4380 |
| gtttgtagcc ttcatcacgg gccacctcca gccactggac cgctgcccc tgccctgtcc | 4440 |
| tggggagtgt ggtcctgcga cttctaagtg gccgcaagcc acctgactcc cccaacacca | 4500 |
| cactctacct ctcaagccca ggtctctccc tagtgaccca cccagcacat ttagctagct | 4560 |
| gagccccaca gccagaggtc ctcaggccct gctttcaggg cagttgctct gaagtcggca | 4620 |
| aggggggagtg actgcctggc cactccatgc cctccaagag ctccttctgc aggagcgtac | 4680 |
| agaacccagg gccctggcac ccgtgcagac cctggcccac cccacctggg cgctcagtgc | 4740 |
| ccaagagatg tccacaccta ggatgtcccg cggtgggtgg ggggcccgag agacgggcag | 4800 |
| gccggggca ggcctggcca tgcggggccg aaccgggcac tgcccagcgt ggggcgcggg | 4860 |
| ggccacggcg cgcgccccca gccccgggc ccagcacccc aaggcggcca acgccaaaac | 4920 |
| tctccctcct cctcttcctc aatctcgctc tcgctctttt ttttttcgc aaaaggaggg | 4980 |
| gagagggggt aaaaaaatgc tgcactgtgc ggcgaagccg gtgagtgagc ggcgcggggc | 5040 |
| caatcagcgt gcgccgttcc gaaagttgcc ttttatggct cgagcggccg cggcggcgcc | 5100 |
| ctataaaacc cagcggcgcg acgcgccacc accgccgaga ccgcgtccgc cccgcgagca | 5160 |
| cagagcctcg cctttgccga tccgccgccc gtccacaccc gccgccaggt aagcccggcc | 5220 |
| agccgaccgg ggcaggcggc tcacggcccg gccgcaggcg gccgcggccc cttcgcccgt | 5280 |
| gcagagccgc cgtctgggcc gcagcggggg gcgcatgggg gggaaccgg accgccgtgg | 5340 |
| ggggcgcggg agaagcccct gggcctccgg agatggggga caccccacgc cagttcggag | 5400 |
| gcgcgaggcc gcgctcggga ggcgcgctcc ggggtgccg ctctcggggc ggggggcaacc | 5460 |
| ggcggggtct ttgtctgagc cgggctcttg ccaatgggga tcgcagggtg ggcgcggcgg | 5520 |
| agccccgcc aggccggtg ggggctgggg cgccattgcg cgtgcgcgct ggtcctttgg | 5580 |
| gcgctaactg cgtgcgcgct gggaattggc gctaattgcg cgtgcgcgct gggactcaag | 5640 |
| gcgctaactg cgcgtgcgtt ctggggcccg gggtgccgcg gcctgggctg gggcgaaggc | 5700 |
| gggctcggcc ggaaggggtg gggtcgccgc ggctcccggg cgcttgcgcg cacttcctgc | 5760 |
| ccgagccgct ggccgcccga gggtgtggcc gctgcgtgcg cgcgcgccga cccggcgctg | 5820 |

```
tttgaaccgg gcggaggcgg ggctggcgcc cggttgggag ggggttgggg cctggcttcc    5880
tgccgcgcgc cgcggggacg cctccgacca gtgtttgcct tttatggtaa taacgcggcc    5940
ggcccggctt cctttgtccc caatctgggc gcgcgccggc gccccctggc ggcctaagga    6000
ctcggcgcgc cggaagtggc cagggcgggg gcgacctcgg ctcacagcgc gcccggctat    6060
tctcgcagct caccaccggt gagctcgttt agtgaaccgt cagatcacta gaagctttat    6120
tgcggtagtt tatcacagtt aaattgctaa cgcagtcagt gcttctgaca caacagtctc    6180
gaacttaagc tgcagtgact ctcttaaggt agccttgcag aagttggtcg tgaggcactg    6240
ggcaggtaag tatcaaggtt acaagacagg tttaaggaga ccaatagaaa ctgggcttgt    6300
cgagacagag aagactcttg cgtttctgat aggcacctat tggtcttact gacatccact    6360
ttgcctttct ctccacaggt gtccactccc agttcaatta cagctcttaa ggctagagta    6420
cttaatacga ctcactatag gctagatccg gaatggtgag caagggcgag gagctgttca    6480
ccggggtggt gcccatcctg gtcgagctgg acggcgacgt aaacggccac aagttcagcg    6540
tgtccggcga gggcgagggc gatgccacct acggcaagct gaccctgaag ttcatctgca    6600
ccaccggcaa gctgcccgtg ccctggccca ccctcgtgac caccctgacc tacggcgtgc    6660
agtgcttcag ccgctacccc gaccacatga agcagcacga cttcttcaag tccgccatgc    6720
ccgaaggcta cgtccaggag cgcaccatct tcttcaagga cgacggcaac tacaagaccc    6780
gcgccgaggt gaagttcgag ggcgacaccc tggtgaaccg catcgagctg aagggcatcg    6840
acttcaagga ggacggcaac atcctggggc acaagctgga gtacaactac aacagccaca    6900
acgtctatat catggccgac aagcagaaga acggcatcaa ggtgaacttc aagatccgcc    6960
acaacatcga ggacggcagc gtgcagctcg ccgaccacta ccagcagaac ccccccatcg    7020
gcgacggccc cgtgctgctg cccgacaacc actacctgag cacccagtcc gccctgagca    7080
aagaccccaa cgagaagcgc gatcacatgg tcctgctgga gttcgtgacc gccgccggga    7140
tcactctcgg catggacgag ctgtacaaga agcttagcca tggcttcccg ccggaggtgg    7200
aggagcagga tgatgcacg ctgcccatgt cttgtgccca ggagagcggg atggaccgtc    7260
accctgcagc ctgtgcttct gctaggatca atgtgtagtc cggaacgcgt cgagcatgca    7320
tctagggcgg ccaattccgc ccctctccct cccccccccc taacgttact ggccgaagcc    7380
gcttggaata aggccggtgt gcgtttgtct atatgtgatt ttccaccata ttgccgtctt    7440
ttggcaatgt gagggcccgg aaacctggcc ctgtcttctt gacgagcatt cctagggtc     7500
tttcccctct cgccaaagga atgcaaggtc tgttgaatgt cgtgaaggaa gcagttcctc    7560
tggaagcttc ttgaagacaa acaacgtctg tagcgaccct ttgcaggcag cggaaccccc    7620
cacctggcga caggtgcctc tgcggccaaa agccacgtgt ataagataca cctgcaaagg    7680
cggcacaacc ccagtgccac gttgtgagtt ggatagttgt ggaaagagtc aaatggctct    7740
cctcaagcgt attcaacaag gggctgaagg atgcccagaa ggtacccat tgtatgggat    7800
ctgatctggg gcctcggtgc acatgcttta catgtgttta gtcgaggtta aaaaaacgtc    7860
taggcccccc gaaccacggg gacgtggttt cctttgaaa aacacgatga taatatggcc    7920
acaacca                                                              7927
```

<210> SEQ ID NO 3
<211> LENGTH: 14004
<212> TYPE: DNA
<213> ORGANISM: Artificial
<220> FEATURE:
<223> OTHER INFORMATION: ppZeo expression cassette of Example 1
    including STAR elements

<400> SEQUENCE: 3

```
tgggtcctat gattatgtcc ggttaaggat ccaccatggc caagttgacc agtgccgttc      60
cggtgctcac cgcgcgcgac gtcgcaggag cggtcgggtt ctggaccgac cggctcgggt     120
tctcccggga cttcgtggag gacgacttcg ccggtgtggt ccgggacgac gtgaccctgt     180
tcatcagcgc ggtccaggac caggtggtgc cggacaacac cctggcctgg gtgtgtgtgc     240
gcggcctgga cgagctgtac accgagtggt cggaggtcgt gtccacgaac ttccgggacg     300
cctccgggcc ggccatgacc gagatcggcg agcagccgtg ggggcgggag ttcgccctgc     360
gcgacccggc cggcaactgc gtgcacttcg tggccgagga gcaggactga attcgcggcc     420
gcttcccttt agtgagggtt aatgcttcga gcagacatga taagatacat tgatgagttt     480
ggacaaacca caactagaat gcagtgaaaa aaatgcttta tttgtgaaat ttgtgatgct     540
attgctttat ttgtaaccat tataagctgc aataaacaag ttaacaacaa caattgcatt     600
cattttatgt ttcaggttca ggggagatg tgggaggttt tttaaagcaa gtaaaacctc      660
tacaaatgtg gtaaaatccg ataaggatcg atccgggctg gcgtaatagc gaagaggccc     720
gcaccgatcg cccttcccaa cagttgccct actagtcggc cgtacgggat ccgatcatgc     780
cagcttaggc gacagagtga gactggacat aataacaata ataataaaaa taaataaata     840
aaacaattat ctgagaggaa aaatttgatt cataataaag agaataaagg ttttggcgt      900 gtttgttttg ttttcaccta agaacagctg ttcccctcat tgggttagtt ttatttgcaa     960
gcagaaatca tctccgcatg atttccaggg tgatggaaaa ctgaatatga atccaccttc    1020
tgccatctat tcacttgtca catttaataa gacactcatg cctattttag catgttttct    1080
tccctaccaa atgagttagt aacatcaaga gattaaaata acacaaataa gaacattgaa    1140
ggtattcaaa tgttacatac aaatattaaa cacaatatta ttataattat tcctggaaat    1200
gacattgcct ctactctcaa ggtaaaggtc attttcttg atttaaactt ttttctcaag     1260
tttgaaatct ctaagtttca acccgtaatc tatttgcaag tttgtgcaaa ttttagggat    1320
tgaatccata gtaattagtg atttattgtg gtgtagggag acaagtcaaa gaatcagga    1380 ctgctaggta gatgactaag gaaaggatgg ttcacgaggt gacataaagc actcagaaga    1440
aaaaggtcag gaaacggagg acagaaaaaa acctaagttc tgctgggtga tgctgaattt    1500
gtcatcacaa atctgcatt gtggaagctt tagctattga ggagattgct caagtgtaga    1560
actgagaaca ataggcagtg aacccgagag aacatcaaga gactgagaga aaatgaacca    1620
gacttccagg tgctccatgt tccaaccaac attttgtatt gtcagaagga attgagaggc    1680
aaaaggaaac ccaataaaaa ataaaacagg aagggcata catgattacc accccttttc     1740
tcaccagctg ctcatggacc agctttctcc tagtgctatt ttcttggtca ctgcatcact    1800
ctgctaacat agtttcccca ctagctctga ggctgtccca gagggaagc cagctgtcat     1860 ctccttcttc cacactctgt tggaggaacc tgtcattagc agctccctac taaacgcatt    1920
tatgacaaac aggcaggaga taattaacta gaaagtgaac aaactcaaac ttcagagcct    1980
ctcatttgta tgaatgccct tgtaaggtct tgggcctatt ttaatatta taaatgtgtt     2040
```

```
attttcttct aaagaaaacc accaaattgt ataagctaca gaatctgcaa aactgaggtc    2100
catccatgca ctcaggatac attcatagca tctctgagct ggaaaatatc ttaaaggtca    2160
tatatgtcct ccaacactgc aagaatctct ctggcagcat tcttttaaaa tcatcatcta    2220
aaagagggaa atccccagct gtgtttggat tttgctctgt cacttgtcca gtttccccat    2280
ccataaaagg gcaacaatat gaatttcctg ataaggtagt tgttaatata aatacaaagt    2340
gcgtagccac ttccctaaga aaaatatggg gtttctgctt cacagtctag ggagaggaaa    2400
aaaaaggggg gtcagaagtg attattatta tcattctata ttggaatgtt ttcagacata    2460
aaaagctcac cacgtcttag gccagacaga tgcattatga aagttaagct aagtcttcct    2520
catcatgagc tgcacctata tccccattac ttcttctaga actgcataat ttatttattc    2580
tttcttcaaa agtttgagag agccattctt gtcctctaag atttttttttt tttttttgg    2640 agacagagtc tccgtctgtt gcccaggctg gagtgcaatg gcactatctc agctcactgc    2700
aacctctgcc tcccagattc aagtgattct cctgcctcag cctcccgagt agctgggatt    2760
acaagcacgc accaccacaa ccagctaatt tttcgtattt tttagtagag acgaggtttt    2820
accatgttgg ccaggctggt cttgaactcc tgacctcggg tgatcgcggc cgcatgcaag    2880
cttggcgtaa tcatggtcat agctgttttcc tgtgtgaaat tgttatccgc tcacaattcc    2940
acacaacata cgagccggaa gcataaagtg taaagcctgg ggtgcctaat gagtgagcta    3000
actcacatta attgcgttgc gctcactgcc cgctttccag tcgggaaacc tgtcgtgcca    3060
gctgcattaa tgaatcggcc aacgcgcggg gagaggcggt ttgcgtattg ggcgctcttc    3120
cgcttcctcg ctcactgact cgctgcgctc ggtcgttcgg ctgcggcgag cggtatcagc    3180
tcactcaaag gcggtaatac ggttatccac agaatcaggg gataacgcag gaaagaacat    3240
gtgagcaaaa ggccagcaaa aggccaggaa ccgtaaaaag gccgcgttgc tggcgttttt    3300
ccataggctc cgcccccctg acgagcatca caaaaatcga cgctcaagtc agaggtggcg    3360
aaacccgaca ggactataaa gataccaggc gtttccccct ggaagctccc tcgtgcgctc    3420
tcctgttccg accctgccgc ttaccggata cctgtccgcc tttctccctt cgggaagcgt    3480
ggcgctttct catagctcac gctgtaggta tctcagttcg gtgtaggtcg ttcgctccaa    3540
gctgggctgt gtgcacgaac cccccgttca gcccgaccgc tgcgccttat ccggtaacta    3600
tcgtcttgag tccaacccgg taagacacga cttatcgcca ctggcagcag ccactggtaa    3660
caggattagc agagcgaggt atgtaggcgg tgctacagag ttcttgaagt ggtggcctaa    3720
ctacggctac actagaagga cagtatttgg tatctgcgct ctgctgaagc cagttacctt    3780
cggaaaaaga gttggtagct cttgatccgg caaacaaacc accgctggta gcggtggttt    3840
ttttgtttgc aagcagcaga ttacgcgcag aaaaaaagga tctcaagaag atcctttgat    3900
cttttctacg gggtctgacg ctcagtggaa cgaaaactca cgttaaggga ttttggtcat    3960
gagattatca aaaaggatct tcacctagat ccttttaaat taaaaatgaa gttttaaatc    4020
aatctaaagt atatatgagt aaacttggtc tgacagttac caatgcttaa tcagtgaggc    4080
acctatctca gcgatctgtc tatttcgttc atccatagtt gcctgactcc ccgtcgtgta    4140
gataactacg atacgggagg gcttaccatc tggccccagt gctgcaatga taccgcgaga    4200
cccacgctca ccggctccag atttatcagc aataaaccag ccagccggaa gggccgagcg    4260
cagaagtggt cctgcaactt tatccgcctc catccagtct attaattgtt gccgggaagc    4320
tagagtaagt agttcgccag ttaatagttt gcgcaacgtt gttgccattg ctacaggcat    4380
```

```
cgtggtgtca cgctcgtcgt ttggtatggc ttcattcagc tccggttccc aacgatcaag    4440
gcgagttaca tgatccccca tgttgtgcaa aaaagcggtt agctccttcg gtcctccgat    4500
cgttgtcaga agtaagttgg ccgcagtgtt atcactcatg gttatggcag cactgcataa    4560
ttctcttact gtcatgccat ccgtaagatg ctttttctgtg actggtgagt actcaaccaa    4620
gtcattctga gaatagtgta tgcggcgacc gagttgctct tgcccggcgt caatacggga    4680
taataccgcg ccacatagca gaactttaaa agtgctcatc attggaaaac gttcttcggg    4740
gcgaaaactc tcaaggatct taccgctgtt gagatccagt tcgatgtaac ccactcgtgc    4800
acccaactga tcttcagcat cttttacttt caccagcgtt tctgggtgag caaaaacagg    4860
aaggcaaaat gccgcaaaaa agggaataag ggcgacacgg aaatgttgaa tactcatact    4920 cttcctttt caatattatt gaagcattta tcagggttat tgtctcatga gcggatacat    4980
atttgaatgt atttagaaaa ataaacaaat aggggttccg cgcacatttc cccgaaaagt    5040
gccacctgac gtctaagaaa ccattattat catgacatta acctataaaa ataggcgtat    5100
cacgaggccc ttaaggccgc ctgatgcggt attttctcct tacgcatctg tgcggtattt    5160
cacaccgcat atggtgcact ctcagtacaa tctgctctga tgccgcatag ttaagccagc    5220
cccgacaccc gccaacaccc gctgacgcgc cctgacgggc ttgtctgctc ccggcatccg    5280
cttacagaca agctgtgacc gtctccggga gctgcatgtg tcagaggttt tcaccgtcat    5340
caccgaaacg cgcgagacga agggccgcg atcacccgag gtcaggagtt caagaccagc    5400
ctggccaaca tggtaaaacc tcgtctctac taaaaaatac gaaaaattag ctggttgtgg    5460
tggtgcgtgc ttgtaatccc agctactcgg gaggctgagg caggagaatc acttgaatct    5520
gggaggcaga ggttgcagtg agctgagata gtgccattgc actccagcct gggcaacaga    5580
cggagactct gtctccaaaa aaaaaaaaaa aaatcttaga ggacaagaat ggctctctca    5640 aactttgaa gaaagaataa ataaattatg cagttctaga agaagtaatg gggatatagg    5700
tgcagctcat gatgaggaag acttagctta actttcataa tgcatctgtc tggcctaaga    5760
cgtggtgagc tttttatgtc tgaaaacatt ccaatataga atgataataa taatcacttc    5820 tgaccccccct ttttttttcct ctccctagac tgtgaagcag aaaccccata ttttcttag    5880 ggaagtggct acgcactttg tatttatatt aacaactacc ttatcaggaa attcatattg    5940 ttgcccttttt atggatgggg aaactggaca agtgacagag caaatccaa acacagctgg    6000 ggatttccct cttttagatg atgatttta aagaatgctg ccagagagat tcttgcagtg    6060
ttggaggaca tatatgacct ttaagatatt ttccagctca gagatgctat gaatgtatcc    6120
tgagtgcatg gatggacctc agttttgcag attctgtagc ttatacaatt tggtggtttt    6180
ctttagaaga aaataacaca tttataaata ttaaaatagg cccaagacct tacaagggca    6240
ttcatacaaa tgagaggctc tgaagtttga gtttgttcac tttctagtta attatctcct    6300
gcctgtttgt cataaatgcg tttagtaggg agctgctaat gacaggttcc tccaacagag    6360
tgtggaagaa ggagatgaca gctggcttcc cctctgggac agcctcagag ctagtgggga    6420
aactatgtta gcagagtgat gcagtgacca agaaaatagc actaggagaa agctggtcca    6480
tgagcagctg gtgagaaaag gggtggtaat catgtatgcc cttcctgtt ttatttttta    6540 ttgggtttcc ttttgcctct caattccttc tgacaataca aatgttggt tggaacatgg    6600 agcacctgga agtctggttc attttctctc agtctcttga tgttctctcg ggttcactgc    6660
ctattgttct cagttctaca cttgagcaat ctcctcaata gctaaagctt ccacaatgca    6720
gattttgtga tgacaaattc agcatcaccc agcagaactt aggtttttt ctgtcctccg    6780
```

```
tttcctgacc ttttttcttct gagtgcttta tgtcacctcg tgaaccatcc tttccttagt    6840
catctaccta gcagtcctga ttcttttgac ttgtctccct acaccacaat aaatcactaa    6900
ttactatgga ttcaatccct aaaatttgca caaacttgca aatagattac gggttgaaac    6960
ttagagattt caaacttgag aaaaaagttt aaatcaagaa aaatgacctt taccttgaga    7020
gtagaggcaa tgtcatttcc aggaataatt ataataatat tgtgtttaat atttgtatgt    7080
aacatttgaa taccttcaat gttcttattt gtgttatttt aatctcttga tgttactaac    7140
tcatttggta gggaagaaaa catgctaaaa taggcatgag tgtcttatta aatgtgacaa    7200
gtgaatagat ggcagaaggt ggattcatat tcagttttcc atcaccctgg aaatcatgcg    7260
gagatgattt ctgcttgcaa ataaaactaa cccaatgagg ggaacagctg ttcttaggtg    7320
aaaacaaaac aaaacacgcca aaaacccttta ttctctttat tatgaatcaa attttttcctc    7380 tcagataatt gttttattta tttatttta ttattattgt tattatgtcc agtctcactc    7440
tgtcgcctaa gctggcatga tcggatctga taattccttt gcctaattt cgagttctat    7500 agtgtcgcgg ccgctatggt accggcgcgc caagcttgga tcctaaaatt ttgtgaccct    7560
agagcaagta ctaactatga aagtgaaata gagaatgaag gaattattta attaagtcca    7620
gcaaaaccca accaaatcat ctgtaaaata tatttgtttt caacatccag gtattttctg    7680
tgtaaaaggt tgagttgtat gctgacttat tgggaaaaat aattgagttt tccccttcac    7740
tttgccagtg agaggaaatc agtactgtaa ttgttaaagg ttacccatac ctacctctac    7800
taccgtctag cataggtaaa gtaatgtaca ctgtgaagtt tcctgcttga ctgtaatgtt    7860
ttcagtttca tcccattgat tcaacagcta tttattcagc acttactaca accatgctgg    7920
aaacccaaga gtaaataggc tgtgttactc aacaggactg aggtacagcc gaactgtcag    7980
gcaaggttgc tgtcctttgg acttgcctgc tttctctcta tgtaggaaga gaaatggac    8040 ataccgtcca ggaaatagat atatgttaca tttccttatt ccataattaa tattaataac    8100
cctggacaga aactaccaag tttctagacc cttatagtac caccttaccc tttctggatg    8160
aatccttcac atgttgatac atttatcca aatgaaaatt ttggtactgt aggtataaca    8220
gacaaagaga gaacagaaaa ctagagatga agtttgggaa aaggtcaaga aagtaaataa    8280
tgcttctaga agacacaaaa agaaaaatga aatggtaatg ttgggaaagt tttaatacat    8340
tttgccctaa ggaaaaaaac tacttgttga aattctactt aagactggac cttttctcta    8400
aaaattgtgc ttgatgtgaa ttaaagcaac acagggaaat ttatgggctc cttctaagtt    8460
ctacccaact caccgcaaaa ctgttcctag taggtgtggt atactctttc agattctttg    8520
tgtgtatgta tatgtgtgtg tgtgtgtgtg tttgtatgtg tacagtctat atacatatgt    8580
gtacctacat gtgtgtatat ataaatatat atttacctgg atgaaatagc atattataga    8640
atattctttt ttctttaaat atatatgtgc atacatatgt atatgcacat atatacataa    8700
atgtagatat agctaggtag gcattcatgt gaaacaaaga agcctattac ttttaatgg    8760 ttgcatgata ttccatcata ggagtatagt acaacttatg taacacacat ttggcttgtt    8820
gtaaaatttt ggtattaata aaatagcaca tatcatgcaa agacacccctt gcataggtct    8880 attcattctt tgatttttac cttaggacaa aatttaaaag tagaatttct gggtcaagca    8940
gtatgctcat ttaaaatgtc attgcatatt tccaaattgt cctccagaaa agtagtaaca    9000
gtaacaattg atggactgcg tgttttctaa aacttgcatt ttttttcctta ttggtgaggt    9060 ttggcatttt ccatatgttt attggcattt taatttttttt tggttcatgt ctttttattcc    9120
```

```
cttcctgcaa atttgtggtg tgtctcaact ttatttatac tctcattttc ataatttct     9180
aaaggaattt gactttaaaa aaataagaca gccaatgctt tggtttaatt tcattgctgc     9240
tttttgaagt gactgctgtg tttttatata cttttatatt ttgttgtttt agcaaattct     9300
tctatattat aattgtgtat gctggaacaa aaagttatat tcttaatct agataaaata     9360
tttcaagatg ttgtaattac agtccctct aaaatcatat aaatagacgc atagctgtgt     9420
gatttgtaat tagttatgtc cattgataga tccaagcttg gcgcgccggg ccagatatac     9480
gcgtcctgca gctgaaagat acaaggccag ggacaggaca gtcccatccc caggaggcag     9540
ggagtataca ggctggggaa gtttgccctt gcgtggggtg gtgatggagg aggctcagca     9600
agtcttctgg actgtgaacc tgtgtctgcc actgtgtgct gggtggtggt catctttccc     9660
accaggctgt ggcctctgca accttcaagg gaggagcagg tcccattggc tgagcacagc     9720
cttgtaccgt gaactggaac aagcagcctc cttcctggcc acaggttcca tgtccttata     9780
tggactcatc tttgcctatt gcgacacaca ctcagtgaac acctactacg cgctgcaaag     9840
agccccgcag gcctgaggtg cccccacctc accactcttc ctattttgt gtaaaaatcc     9900
agcttcttgt caccacctcc aaggaggggg aggaggagga aggcaggttc ctctaggctg     9960
agccgaatgc ccctctgtgg tcccacgcca ctgatcgctg catgcccacc acctgggtac    10020
acacagtctg tgattcccgg agcagaacgg accctgccca cccggtcttg tgtgctactc    10080
agtggacaga cccaaggcaa gaaagggtga caaggacagg gtcttcccag gctggctttg    10140
agttcctagc accgccccgc ccccaatcct ctgtggcaca tggagtcttg gtccccagag    10200
tcccccagcg gcctccagat ggtctgggag ggcagttcag ctgtggctgc gcatagcaga    10260
catacaacgg acggtgggcc cagacccagg ctgtgtagac ccagcccccc cgccccgcag    10320
tgcctaggtc acccactaac gccccaggcc ttgtcttggc tgggcgtgac tgttaccctc    10380
aaaagcaggc agctccaggg taaaaggtgc cctgccctgt agagcccacc ttccttccca    10440
gggctgcggc tgggtaggtt tgtagccttc atcacgggcc acctccagcc actgaccgc    10500
tggcccctgc cctgtcctgg ggagtgtggt cctgcgactt ctaagtggcc gcaagccacc    10560
tgactccccc aacaccacac tctacctctc aagcccaggt ctctcctag tgacccaccc    10620
agcacattta gctagctgag ccccacagcc agaggtcctc aggccctgct ttcagggcag    10680
ttgctctgaa gtcggcaagg gggagtgact gcctggccac tccatgccct ccaagagctc    10740
cttctgcagg agcgtacaga acccagggcc ctggcacccg tgcagaccct ggcccacccc    10800
acctgggcgc tcagtgccca agagatgtcc acacctagga tgtcccgcgg tgggtggggg    10860
gcccgagaga cgggcaggcc ggggcaggc ctggccatgc ggggccgaac cgggcactgc    10920
ccagcgtggg gcgcggggc cacgcgcgcg cccccagcc cccggcccca gcaccccaag    10980
gcggccaacg ccaaaactct ccctcctcct cttcctcaat ctcgctctcg ctctttttt    11040
tttccgcaaa aggaggggag aggggtaaa aaaatgctgc actgtgcggc gaagccggtg    11100
agtgagcggc gcgggccaa tcagcgtgcg ccgttccgaa agttgccttt tatggctcga    11160
gcggccgcgg cggcgcccta taaaacccag cggcgcgacg cgccaccacc gccgagaccg    11220
cgtccgcccc gcgagcacag agcctcgcct ttgccgatcc gccgcccgtc cacacccgcc    11280
gccaggtaag cccggccagc cgaccgggc aggcggctca cggcccggcc gcaggcggcc    11340
gcggcccctt cgcccgtgca gagccgccgt ctgggccgca gcgggggggcg catggggggg    11400
gaaccggacc gccgtgggg gcgcgggaga agcccctggg cctccggaga tggggacac    11460
cccacgccag ttcggaggcg cgaggccgcg ctcgggaggc gcgctccggg ggtgccgctc    11520
```

-continued

```
tcggggcggg ggcaaccggc ggggtctttg tctgagccgg gctcttgcca atggggatcg   11580
cagggtgggc gcggcggagc ccccgccagg cccggtgggg gctggggcgc cattgcgcgt   11640
gcgcgctggt cctttgggcg ctaactgcgt gcgcgctggg aattggcgct aattgcgcgt   11700
gcgcgctggg actcaaggcg ctaactgcgc gtgcgttctg gggcccgggg tgccgcggcc   11760
tgggctgggg cgaaggcggg ctcggccgga aggggtgggg tcgccgcggc tcccgggcgc   11820
ttgcgcgcac ttcctgcccg agccgctggc cgcccgaggg tgtggccgct gcgtgcgcgc   11880
gcgccgaccc ggcgctgttt gaaccgggcg gaggcggggc tggcgcccgg ttgggagggg   11940 gttgggggcct ggcttcctgc cgcgcgccgc ggggacgcct ccgaccagtg tttgccttttt  12000 atggtaataa cgcggccggc ccggcttcct ttgtccccaa tctgggcgcg cgccggcgcc   12060
ccctggcggc ctaaggactc ggcgcgccgg aagtggccag ggcgggggcg acctcggctc   12120
acagcgcgcc cggctattct cgcagctcac caccggtgag ctcgtttagt gaaccgtcag   12180
atcactagaa gctttattgc ggtagtttat cacagttaaa ttgctaacgc agtcagtgct   12240
tctgacacaa cagtctcgaa cttaagctgc agtgactctc ttaaggtagc cttgcagaag   12300
ttggtcgtga ggcactgggc aggtaagtat caaggttaca agacaggttt aaggagacca   12360
atagaaactg ggcttgtcga gacagagaag actcttgcgt ttctgatagg cacctattgg   12420
tcttactgac atccactttg cctttctctc cacaggtgtc cactcccagt tcaattacag   12480
ctcttaaggc tagagtactt aatacgactc actataggct agatccggaa tggtgagcaa   12540
gggcgaggag ctgttcaccg gggtggtgcc catcctggtc gagctggacg gcgacgtaaa   12600
cggccacaag ttcagcgtgt ccggcgaggg cgagggcgat gccacctacg gcaagctgac   12660
cctgaagttc atctgcacca ccggcaagct gcccgtgccc tggcccaccc tcgtgaccac   12720
cctgacctac ggcgtgcagt gcttcagccg ctaccccgac cacatgaagc agcacgactt   12780
cttcaagtcc gccatgcccg aaggctacgt ccaggagcgc accatcttct tcaaggacga   12840
cggcaactac aagacccgcg ccgaggtgaa gttcgagggc gacaccctgg tgaaccgcat   12900
cgagctgaag ggcatcgact tcaaggagga cggcaacatc ctggggcaca gctggagta    12960 caactacaac agccacaacg tctatatcat ggccgacaag cagaagaacg gcatcaaggt   13020
gaacttcaag atccgccaca acatcgagga cggcagcgtg cagctcgccg accactacca   13080
gcagaacacc cccatcggcg acggccccgt gctgctgccc gacaaccact acctgagcac   13140
ccagtccgcc ctgagcaaag accccaacga gaagcgcgat cacatggtcc tgctggagtt   13200
cgtgaccgcc gccgggatca ctctcggcat ggacgagctg tacaagaagc ttagccatgg   13260
cttcccgccg gaggtggagg agcaggatga tggcacgctg cccatgtctt gtgcccagga   13320
gagcgggatg gaccgtcacc ctgcagcctg tgcttctgct aggatcaatg tgtagtccgg   13380
aacgcgtcga gcatgcatct agggcggcca attccgcccc tctccctccc cccccctaa    13440 cgttactggc cgaagccgct tggaataagg ccggtgtgcg tttgtctata tgtgattttc    13500
caccatattg ccgtcttttg gcaatgtgag ggcccggaaa cctggccctg tcttcttgac   13560
gagcattcct aggggtcttt cccctctcgc caaaggaatg caaggtctgt tgaatgtcgt   13620
gaaggaagca gttcctctgg aagcttcttg aagacaaaca acgtctgtag cgaccctttg   13680
caggcagcgg aaccccccac ctggcgacag gtgcctctgc ggccaaaagc cacgtgtata   13740
agatacacct gcaaaggcgg cacaaccccca gtgccacgtt gtgagttgga tagttgtgga   13800
aagagtcaaa tggctctcct caagcgtatt caacaagggg ctgaaggatg cccagaaggt   13860
```

```
acccccattgt atgggatctg atctgggggcc tcggtgcaca tgctttacat gtgtttagtc    13920
gaggttaaaa aaacgtctag gccccccgaa ccacggggac gtggttttcc tttgaaaaac    13980
acgatgataa tatggccaca acca                                            14004

<210> SEQ ID NO 4
<211> LENGTH: 7
<212> TYPE: RNA
<213> ORGANISM: Artificial
<220> FEATURE:
<223> OTHER INFORMATION: Kozak sequence
<220> FEATURE:
<221> NAME/KEY: misc_feature
<222> LOCATION: (2)..(3)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u

<400> SEQUENCE: 4 annaugn                                                                    7

<210> SEQ ID NO 5
<211> LENGTH: 7
<212> TYPE: RNA
<213> ORGANISM: Artificial
<220> FEATURE:
<223> OTHER INFORMATION: Kozak sequence
<220> FEATURE:
<221> NAME/KEY: misc_feature
<222> LOCATION: (2)..(3)
<223> OTHER INFORMATION: n is a, c, g, or u

<400> SEQUENCE: 5 gnnaugg                                                                    7

<210> SEQ ID NO 6
<211> LENGTH: 10
<212> TYPE: RNA
<213> ORGANISM: Artificial
<220> FEATURE:
<223> OTHER INFORMATION: Kozak sequence

<400> SEQUENCE: 6 gccrccaugg                                                                10

<210> SEQ ID NO 7
<211> LENGTH: 270
<212> TYPE: DNA
<213> ORGANISM: Artificial
<220> FEATURE:
<223> OTHER INFORMATION: synthetic pp90

<400> SEQUENCE: 7
gaaattgctt ctggtggcgc tcccctctct aaggaagtcg gggaagcggt tgccaagagg      60
ttccatctgc aggtatcag gcaaggatat gggctcactg agactacatc agctattctg      120
attacacccg aggggatga taaaccgggc gcggtcggta agttgttcc attttttgaa       180 gcgaaggttg ggatctggat acgggaaaac gctggcgtt aatcaaagag gcgaactgtg     240
tgtgagaggt cctatgatta tgtccggtta                                     270

<210> SEQ ID NO 8
<211> LENGTH: 375
<212> TYPE: DNA
<213> ORGANISM: Artificial
```

```
<220> FEATURE:
<223> OTHER INFORMATION: synthetic wt Zeo resistance gene

<400> SEQUENCE: 8
atggccaagt tgaccagtgc cgttccggtg ctcaccgcgc gcgacgtcgc cggagcggtc      60
gagttctgga ccgaccggct cgggttctcc cggacttcg tggaggacga cttcgccggt      120
gtggtccggg acgacgtgac cctgttcatc agcgcggtcc aggaccaggt ggtgccggac      180
aacaccctgg cctgggtgtg ggtgcgcggc ctggacgagc tgtacgccga gtggtcggag      240
gtcgtgtcca cgaacttccg ggacgcctcc gggccggcca tgaccgagat cggcgagcag      300
ccgtgggggc gggagttcgc cctgcgcgac ccggccggca ctgcgtgca cttcgtggcc      360 gaggagcagg actga                                                      375

<210> SEQ ID NO 9
<211> LENGTH: 411
<212> TYPE: DNA
<213> ORGANISM: Artificial
<220> FEATURE:
<223> OTHER INFORMATION: bicistronic coding sequence of pp8 Zeo EPP5

<400> SEQUENCE: 9
atgggtccta tgattatgtc cggttaagga tccaccatgg ccaagttgac cagtgccgtt      60
ccggtgctca ccgcgcgcga cgtcgcagga gcggtcgggt tctggaccga ccggctcggg      120
ttctcccggg acttcgtgga ggacgacttc gccggtgtgg tccgggacga cgtgaccctg      180
ttcatcagcg cggtccagga ccaggtggtg ccggacaaca ccctggcctg ggtgtgtgtg      240
cgcggcctgg acgagctgta caccgagtgg tcggaggtcg tgtccacgaa cttccgggac      300
gcctccgggc cggccatgac cgagatcggc gagcagccgt ggggcggga gttcgccctg      360 cgcgacccgg ccggcaactg cgtgcacttc gtggccgagg agcaggactg a              411

<210> SEQ ID NO 10
<211> LENGTH: 3500
<212> TYPE: DNA
<213> ORGANISM: Artificial
<220> FEATURE:
<223> OTHER INFORMATION: human beta actin promoter fragment

<400> SEQUENCE: 10
gccccagtga cagctccgaa agctccctta cagggcaaag ttcccaagca cagaagagaa      60
cctgttcact tctcccctgc tcggcccgcc cctggccag gcacctctac ttcctctttt     120
cctgctccgc tgcttgcttt ctctcttcag ctcctccctg cccctcaccc caggctgctc     180
ggccacctcc aacctgccac ctgaggacac ccaggcagtc actcattcaa cagcgaggag     240
ccctggggtg ggtgtagtgg gaaggagtgg gggtgacgga gaccctggga gggctcgcag     300
cctggtggct gaggcccagt tctaaatgcc agctgcaagc cttggtctga ggtagggagg     360
aaggcgtggc tgcagaggct aaaacgcttc cccaaagagg ggctttctgg gatgggactt     420
gaagggtgca taggagagca ctaggaagtg gccgctgcag acagagggaa ccacaagcca     480
ggaggacagg ccaggaatgc tgcagcccgg ggcggggtgg gctgagct cctgtctctt     540 ggccagctga atggaggccc agtggcaaca caggtcctgc tggggatca ggtctgctct     600 gcaccccacc ttgctgcctg agccgcccca cctgacaacc tctcatccct gctctgcaga     660
tccggtccca tccccactgc ccaccccacc ccccagcac tccacccagt tcaacgttcc     720
acgaaccccc agaaccagcc ctcatcaaca ggcagcaaga agggcccccc gcccatcgcc     780
```

```
ccacaacgcc agccgggtga acgttggcag gtcctgaggc agctggcaag acgcctgcag    840
ctgaaagata caaggccagg gacaggacag tcccatcccc aggaggcagg gagtatacag    900
gctggggaag tttgcccttg cgtggggtgg tgatggagga ggctcagcaa gtcttctgga    960
ctgtgaacct gtgtctgcca ctgtgtgctg ggtggtggtc atctttccca ccaggctgtg   1020
gcctctgcaa ccttcaaggg aggagcaggt cccattggct gagcacagcc ttgtaccgtg   1080
aactggaaca agcagcctcc ttcctggcca caggttccat gtccttatat ggactcatct   1140
ttgcctattg cgacacacac tcagtgaaca cctactacgc gctgcaaaga gccccgcagg   1200
cctgaggtgc ccccacctca ccactcttcc tattttgtg taaaaatcca gcttcttgtc   1260
accacctcca aggaggggga ggaggaggaa ggcaggttcc tctaggctga gccgaatgcc   1320
cctctgtggt cccacgccac tgatcgctgc atgcccacca cctgggtaca cacagtctgt   1380
gattcccgga gcagaacgga ccctgcccac ccggtcttgt gtgctactca gtggacagac   1440
ccaaggcaag aaagggtgac aaggacaggg tcttcccagg ctggctttga gttcctagca   1500
ccgccccgcc cccaatcctc tgtggcacat ggagtcttgg tccccagagt cccccagcgg   1560
cctccagatg gtctgggagg gcagttcagc tgtggctgcg catagcagac atacaacgga   1620
cggtgggccc agacccaggc tgtgtagacc cagcccccc gccccgcagt gcctaggtca   1680
cccactaacg ccccaggcct tgtcttggct gggcgtgact gttaccctca aaagcaggca   1740
gctccagggt aaaaggtgcc ctgccctgta gagcccacct tccttcccag ggctgcggct   1800
gggtaggttt gtagccttca tcacgggcca cctccagcca ctggaccgct ggcccctgcc   1860
ctgtcctggg gagtgtggtc ctgcgacttc taagtggccg caagccacct gactccccca   1920
acaccacact ctacctctca agcccaggtc tctccctagt gacccaccca gcacatttag   1980
ctagctgagc cccacagcca gaggtcctca ggccctgctt tcaggcagt tgctctgaag    2040
tcggcaaggg ggagtgactg cctggccact ccatgccctc caagagctcc ttctgcagga   2100
gcgtacagaa cccagggccc tggcacccgt gcagaccctg gcccacccca cctgggcgct   2160
cagtgcccaa gagatgtcca cacctaggat gtcccgcggt gggtggggg cccgagagac    2220
gggcaggccg ggggcaggcc tggccatgcg gggccgaacc gggcactgcc cagcgtgggg   2280
cgcggggggcc acggcgcgcg ccccccagccc ccgggcccag caccccaagg cggccaacgc  2340
caaaactctc cctcctcctc ttcctcaatc tcgctctcgc tctttttttt tttcgcaaaa   2400
ggagggggaga ggggggtaaaaa aaaatgctgca ctgtgcggcg aagccggtga gtgagcggcg 2460
cggggccaat cagcgtgcgc cgttccgaaa gttgccttt atggctcgag cggccgcggc    2520
ggcgccctat aaaacccagc ggcgcgacgc gccaccaccg ccgagaccgc gtccgccccg   2580
cgagcacaga gcctcgcctt tgccgatccg ccgcccgtcc acaccgccg ccaggtaagc    2640
ccggccagcc gaccggggca ggcggctcac ggcccggccg caggcggccg cggccccttc   2700
gcccgtgcag agccgccgtc tgggccgcag cgggggcgc atgggggggg aaccggaccg    2760
ccgtgggggg cgcgggagaa gcccctgggc ctccggagat gggggacacc ccacgccagt   2820
tcggaggcgc gaggccgcgc tcgggaggcg cgctccgggg gtgccgctct cggggcgggg   2880
gcaaccggcg gggtctttgt ctgagccggg ctcttgccaa tggggatcgc agggtgggcg   2940
cggcggagcc cccgccaggc ccggtggggg ctggggcgcc attgcgcgtg cgcgctggtc   3000
ctttgggcgc taactgcgtg cgcgctggga attggcgcta attgcgcgtg cgcgctggga   3060
ctcaaggcgc taactgcgcg tgcgttctgg ggcccggggt gccgcggcct gggctggggc   3120
gaaggcgggc tcggccggaa ggggtggggt cgccgcggct cccgggcgct tgcgcgcact   3180
```

| | |
|---|---:|
| tcctgcccga gccgctggcc gcccgagggt gtggccgctg cgtgcgcgcg cgccgacccg | 3240 |
| gcgctgtttg aaccgggcgg aggcggggct ggcgcccggt tgggaggggg ttggggcctg | 3300 |
| gcttcctgcc gcgcgccgcg gggacgcctc cgaccagtgt ttgcctttta tggtaataac | 3360 |
| gcggccggcc cggcttcctt tgtccccaat ctgggcgcgc gccggcgccc cctggcggcc | 3420 |
| taaggactcg gcgcgccgga agtggccagg gcggggcga cctcggctca cagcgcgccc | 3480 |
| ggctattctc gcagctcacc | 3500 |

<210> SEQ ID NO 11
<211> LENGTH: 6969
<212> TYPE: DNA
<213> ORGANISM: Homo sapiens

<400> SEQUENCE: 11

| | |
|---|---:|
| ctatgtcatt tttgctaaca tgtaatgggc ttactattgt tattttaatt aaattgataa | 60 |
| atatatattt aaaatgttct tagtttaaat ttctaatata gtaaatattg atagatacaa | 120 |
| cctacataaa caaaagctat atggagtcct caataatttt taagaatgta aagggattct | 180 |
| gaggccaaaa tgtttgagaa ttgctgggct aggattgttc aagcctctct ggggcatatg | 240 |
| ctaattatct taaagccacc caatcatcac ccaccttccc accaatgtct tcgtactcac | 300 |
| ttcttgtgag ccaatcctca cagtcaggag gcagtagtgt taggatggtt gaaagtaaaa | 360 |
| gcacaaagag attgagttca attctttct tggctacctg tgaagtttgt aactttgact | 420 |
| aatttactgg gcccttcaaa agtctcagtt ttctcatcta taaaggggt ataatggtag | 480 |
| tacctacctt atacgtttgt gagaattaag aaagaaggca cataatttat gttagctata | 540 |
| atagatgaaa ttcttttagag ttttatttgt ggttatctaa tcataaggat tggaaagaag | 600 |
| taaagtccat gccaacttgt tttacttctt tgaaaaagag aaacaagagg tatagtaacg | 660 |
| tttaatgttt ggtttaacat gtacagtgga tgagagggca ttctatattg atctcctcaa | 720 |
| tctggccaga aaagtgttgt gatttctaac agtttatttt cacattttgt ttccctaagt | 780 |
| tcaatgagcc ctccacttct aatgaggtgg cttttaggggta gagaaatcaa aaggcagttg | 840 |
| gctttgttgt gacgggcaga tctggatgga gcattataag ggtgaggctg ctgagtttcc | 900 |
| catcttgctt atacatatga tgcttttgaaa cctacgctga cctgttttaa ctctggccta | 960 |
| aagacaggcc aggtgaacag aaatagagcc agcgtctcca ctggcaacac agccatcctg | 1020 |
| aagaggaatg tctgtgtgtg catctgccac cagaagtggg atgctagaga ggcattgatc | 1080 |
| tctttttga tattgagttt tatccaagta ctcattaagt agatcccttt tattttcaaa | 1140 |
| atatctgggg ttaatgtgct taatttggtt agacctagtg agtgagctat ggagaactgg | 1200 |
| aatcatttta tatcagttcc tcatctttgc tcagattcat tctgtactgc ctgtctcttc | 1260 |
| tgcttcttag acaaagattg aacttgcagg ccaggtgcag tggctcatgc ctgtaattcc | 1320 |
| aacactttgg gaggccgagg cgggcagatc acttgaggtc gggaattcga accagcctg | 1380 |
| accaacatgg agaaaccccg cctctactaa aaatacaaag ttagctgggt gtggtggtgc | 1440 |
| atgcctgtaa tcccagctac tcaggaggct gaggcaggag aattgcttca acccaggaga | 1500 |
| cggagattgt ggtgagccga ggtgacgcca ttgcactcca gcctgggcaa caagagtgaa | 1560 |
| actccatctc aaaataaata aataaaaaga ttgaacttgc tacatgcttc tatctctatc | 1620 |
| tgccttctgt gctgccagct cctgcttcta gcaagaagca agagaactta tgttttttca | 1680 |
| acccctagtt ctctcctggt aaaactgtga agaatctatt tgcatatcta gccattctac | 1740 |

```
atgcataaaa atgctatatc gacacaaaga aaagacttgt tcataggctc atagttctga      1800
tacaaggctt accagctgaa ttgcccacag tcaggcccta cagagaactc tgctagtttg      1860
atactcctat taatatacag ctaataggtg gtcctgtatc ctacagctgt ggccaaggtc      1920
ccacacacaa tcaattttcc attccgttag actgggaggg agattgttag ctttctatga      1980
acataagaag atccctgat ggagccatct acataggata ggttttgta taggtttaat       2040 gacccttcag agttggtaaa tggtccacaa tttctctaac cttcacttcc tggacccaaa      2100
gagagattgg caccaacttt actgtgtcat taatttcagg agtcattcac tgaccttctc      2160
cagcagtggc agcaactccc caagtcaatc aggcaataaa accagctgta ccaaaaatgt      2220
aacaacagtt caagtttact ttatccaggg gcctcaagta ttcaagattg acgtccctac      2280
ctccccatct ccaaggatgc cccccctcc ccgccatgat gatacccaag agtgagtcag       2340
tgtagccagg taccattgcc cacaggaggc tcagctttgt cccttcaaa tgatcctccc       2400 caagggcttc tgtttctctt acttctagcc atttggtctt agccattgtg tttcctgtga      2460
tccatatgcc aagcccccac atcttacata ggccattgga aatttgggtg ctctgggaaa      2520
cctcattaat caaccatgt cctgcaaggc tgactgccaa ccagcccaaa gactgacctg       2580
gtgtcacaga gatgtcctga aggccttctc ctcctggtga agcccatcat caagaagatg      2640
ttggacttgc agatccagac aagagaatat gaggatgttc ttaccacatc aggcagtaat      2700
acaatggcct cctaactggt gtccttgtgc ccgtgctttt cctcttctcc attccccata     2760
cagcagtcag gaaatctgat tgtgttcttc ctttgtttaa aacccttttcc tgtgtcccac     2820 atgatggcct gcatgatcct tcatgccctt gaccttgcca acctctcagg tctcatctca      2880
tgccaccttc ttcctccctg ctgtgctcag gccacatggc cttcctctag ctcctcaagt      2940
gcctagaggc ccttccagag gctggtccct ttgactcttc aactcattaa tttccactca      3000
tccttcagag ctcagctcaa atgtcacttc ctcgaggcga ctgtccttga gtccccactc      3060
gctcatcata cttttgctag ctctgcgtcc cgttccatca taggttgtaa ttacaagtct     3120
gagtaatgtg tgcctccttt agtggcttgt aaggttcatg aaggcaggat ctatatctat      3180
caaagttccc cctgaattct gagtacctac acagtaggag tctgataaat atttattgga      3240
caaataaatc aacaaaaata aatatggaaa agttgctatt gtgggcttca ccagttggtg      3300
agtacagatg tagtcctata acttcataca ctttcaattg ctctatcaca tttgtgatag      3360
ctatgaagtt tttccttcta tgcaacatgc tgctattaga cagctacagg aatgagtgaa      3420
tagcttctcc tctagtttct tgtcctcaat ctctctcttt cctcccctct ggcccaccct      3480
aaatacttat acaggcgagt gtggacacac acacacacac acatcctgtg aagaggaatg      3540
agagcacaaa aagttatata caattcattg taatatgaat caggaaaaag cttcctgact      3600
tcagcctaaa gattccctgg gctgagggga aagggaatgt ccagatggca aatggagtga      3660
ggagagaact tatcctggtg ggtcactgaa aagagtgcta agcctgctcc agtggggaag      3720
aggaagatga cagaaatgtc aggtaagttt gtgggaactg aaagggggagg caatctagaa      3780 gtgttctcag gcaaaggccc aaggagaccc aagatctcag agactaaggt gctatgtggc      3840
agatatgagt ctgggacagc ttacagagtc ccatacgtca cagtgtggcc tggaagcaga      3900
tggatggttc tggggcctga gagtgccgca ggagtccatg ggtcttgggt cacagcctgc      3960
agtttccatg actcagcctg gcagtggaat gacttcctgg gcaccccaaa ggctttatag      4020
aagttgaaag gatagttgtc aaacgtgcag gagccttta aatgggatca tagggacaag       4080
gtagcaatca tctgcatgtc aggaaacgaa cactaaacag gatgatggat ggcccagtga      4140
```

```
aggcccaggt gatagcagtc tagaaccagg tacccatct ccccacatgt tgacatgcca   4200
caagcacccc agaaattagt tatttccctg cagttacata ttgactaatt ttaaattgtt   4260
actgcttaca ggatggaggc tctaaataga aaaaagtta gagagaaaca taaatttgtt   4320 atgttttat acagctgggt ttgtgggctg caaattgaaa ccattataca attctctttt   4380
aaaatgcaaa tatccctcat acgcatatca tgtggacaaa gtgtttgttt tattaatagc   4440
atcccctaac ctagtttcac tattaaaagg taggtctgag tgggatgtgg gtccctagtg   4500
acctagtgtg agaatagagg gtgttttgtt ttgttttgtt tttgagactg agtctcgctc   4560
tgttgcccag gctggagtgc agtggcatga tctcggctca ctgcaacctc tgcctcctgg   4620
gttcaagtga ttctcatgcc tcagcctctt gagtagctgg gattagatgt gcccaacacc   4680
acgcctgact aatttttgta ttttagtag ggatggggtt tcaccatgtt ggccaggctg   4740
gtctcaaact cctgacctca gtaatccac ccactttggt ctcccaaagt gctgggatta   4800
caggcgtgag ccaccacgtc cggccttaga gggcattta agggaagaag agaggagttg   4860
ggaaaggatc ttctttctaa tgggaagaga agaagagac aatagaaaaa ggaagaagga   4920
aaagggccca atgaatgtcc aatattcctt ttgttttcat tgtgattctc atacagaatt   4980
cataaatact tcaacctaaa ccattgaaat tggaatttaa tctgaggtat gaaaaaaatg   5040
ctaggtttaa aatcacaacc caggttgaat ttcttacttt gcccattaat agatgtgtga   5100
ccttgagcat tctcttaact tctctgagcc tcagttactt cagttgtaaa aagggtctaa   5160
taaaacacat cccactgaat tactgagagg attgatccaa ttacatgaaa gagctctgaa   5220
acaataaaaa gttgcaccat ctggggtatc agtttgcggt cgaggagaca atggggagaa   5280
ataatgtaag tgttgagcac atctgcggtc tttaaacaga gagctcaaca caaggacatg   5340
ggcatattgg aaaaaactat ttcagaagag gggaaaaggg agaaaggggg atatgtgggt   5400
attagaggca aacccagata tcctgccttg aggtcaaata attataacat taaatcctgt   5460
ttactgatgc ttagctgtca ggctcttgct catttaccct tggagatccat ttagaattag   5520 tgtaaggtgt aattgacctg tactttagagt tccagaatag acaatcact tccaaatgcc   5580 ctcagtataa gaaattaaca gtacttgggg ctttagaaat caatgttcaa cctttcaact   5640
actagaaagc cttttagtt attgtgctta ctatgaaagc ccttggctgt cagttcaaca   5700
agtcgttctt gctttgtgac atctctggaa gtttaatagt tctgtgagaa agtccttgtc   5760
agtgttctga aaactgggaa ttaggaagtc gacttccaat caagcttcag atgacatgcg   5820
acatgcgtta agtttagaaa taacgttagt gttctaatt tagcatcgtg ttggagtcct   5880
aattatgaaa tgacattaag aaaattccat tcctcagaat tcttgtgcag tagcattggg   5940
tagaaacacc attgtgttct gtgacctggg gtagggatga tatctcaaaa acgcatgctc   6000
aggttgccca tggtgatagc taaactgtct tctcaggaga ggagcaggct ttattaactg   6060
gaactcacca gatttcacag aacattttga agggcttagg attgtgagtt tggaggtaga   6120
tgccaagcag aggtaaacat tttgtataac agaagaaaca tatttgatat gggagagaga   6180
cagaaatctt gtggaaaact ccagagccat caaagctggg acagtgttaa agacgagcac   6240
cctggaagtc aggagccaag tgtgggtttt gaggaacaga tatattaagg gggattctca   6300
caaatgtttt attttgacaa atatcaataa tttagaaaag ttgcaagaat agtatagcaa   6360
ttattcatat acccccttcca tatagtacac agaaaaagag ggtatatatt ttaataaata   6420
tttgtgtata cacattttgt gtatagatag gcagataaat agataaagag acaaatgtgc   6480
```

```
acctgtgtat aattttctga actgtttgag aattggttgt aagcatcacg acacttcacc    6540
accaaatact tcagcatgtg tctcctaaga acaaggctgt tctctacatg accacaacat    6600
agttatttca cccagaaact taaacttgat acaatacaat atctaatatt cagtccatat    6660
tcaaatttct cctatcatcc aaataatatc attactaatc tccaatataa agagatttaa    6720
aacatgtttt ccatgttcaa cataaatgtc ttctccattt ttcttacaaa atcatcaaaa    6780
acaactacgt ttcccattta tacttttaca ccagtagttt ctttggagga acttgcactt    6840
gtcccacatc cagattggca ggggataaaa tagaaataat aagagctggc agaagagagg    6900
ctggttgatg ctgattacat tcaaaataac tatttggagg aaaaagcact gattctgttc    6960
ctggggtgt                                                            6969

<210> SEQ ID NO 12
<211> LENGTH: 3498
<212> TYPE: DNA
<213> ORGANISM: Homo sapiens

<400> SEQUENCE: 12
gcccacccta aatacttata caggcgagtg tggacacaca cacacacaca catcctgtga      60
agaggaatga gagcacaaaa agttatatac aattcattgt aatatgaatc aggaaaaagc     120
ttcctgactt cagcctaaag attccctggg ctgagggaa agggaatgtc cagatggcaa     180
atggagtgag gagagaactt atcctggtgg gtcactgaaa agagtgctaa gcctgctcca     240
gtggggaaga ggaagatgac agaaatgtca ggtaagtttg tgggaactga aggggaggc     300 aatctagaag tgttctcagg caaaggccca aggagaccca agatctcaga gactaaggtg     360
ctatgtggca gatatgagtc tgggacagct tacagagtcc catacgtcac agtgtggcct     420
ggaagcagat ggatggttct ggggcctgag agtgccgcag gagtccatgg gtcttgggtc     480
acagcctgca gtttccatga ctcagcctgg cagtggaatg acttcctggg cacccccaaag   540 gctttataga agttgaaagg atagttgtca aacgtgcagg agccttttaa atgggatcat    600
agggacaagg tagcaatcat ctgcatgtca ggaaacgaac actaaacagg atgatggatg    660
gcccagtgaa ggcccaggtg atagcagtct agaaccaggt accccatctc cccacatgtt    720
gacatgccac aagcacccca gaaattagtt atttccctgc agttacatat tgactaattt     780
taaattgtta ctgcttacag gatggaggct ctaaatagaa aaaagttag agagaaacat     840 aaatttgtta tgttttata cagctgggtt tgtgggctgc aaattgaaac cattatacaa     900
ttctctttta aaatgcaaat atccctcata cgcatatcat gtggacaaag tgtttgtttt    960
attaatagca tcccctaacc tagtttcact attaaaggt aggtctgagt gggatgtggg    1020
tccctagtga cctagtgtga aatagaggg tgtttttgttt tgttttgttt ttgagactga    1080
gtctcgctct gttgcccagg ctggagtgca gtggcatgat ctcggctcac tgcaacctct    1140
gcctcctggg ttcaagtgat tctcatgcct cagcctcttg agtagctggg attagatgtg    1200
cccaacacca cgcctgacta atttttgtat ttttagtagg gatggggttt caccatgttg    1260
gccaggctgg tctcaaactc ctgacctcaa gtaatccacc cactttggtc tcccaaagtg    1320
ctgggattac aggcgtgagc caccacgtcc ggccttagag ggcattttaa gggaagaaga    1380
gaggagttgg gaaaggatct tctttctaat gggaagagaa agaagagaca atagaaaaag    1440
gaagaaggaa aagggcccaa tgaatgtcca atattccttt tgttttcatt gtgattctca    1500
tacagaattc ataaatactt caacctaaac cattgaaatt ggaatttaat ctgaggtatg    1560
aaaaaaatgc taggtttaaa atcacaaccc aggttgaatt tcttactttg cccattaata    1620
```

| | | | |
|---|---|---|---|
| gatgtgtgac | cttgagcatt | ctcttaactt | ctctgagcct | cagttacttc | agttgtaaaa | 1680 |
| agggtctaat | aaaacacatc | ccactgaatt | actgagagga | ttgatccaat | acatgaaag | 1740 |
| agctctgaaa | caataaaaag | ttgcaccatc | tggggtatca | gtttgcggtc | gaggagacaa | 1800 |
| tggggagaaa | taatgtaagt | gttgagcaca | tctgcggtct | ttaaacagag | agctcaacac | 1860 |
| aaggacatgg | gcatattgga | aaaaactatt | tcagaagagg | ggaaaaggga | gaaaggggga | 1920 |
| tatgtgggta | ttagaggcaa | acccagatat | cctgccttga | ggtcaaataa | ttataacatt | 1980 |
| aaatcctgtt | tactgatgct | tagctgtcag | gctcttgctc | atttaccttg | gagatccatt | 2040 |
| tagaattagt | gtaaggtgta | attgacctgt | acttagagtt | ccagaatagg | acaatcactt | 2100 |
| ccaaatgccc | tcagtataag | aaattaacag | tacttggggc | tttagaaatc | aatgttcaac | 2160 |
| ctttcaacta | ctagaaagcc | tttttagtta | ttgtgcttac | tatgaaagcc | cttggctgtc | 2220 |
| agttcaacaa | gtcgttcttg | ctttgtgaca | tctctggaag | tttaatagtt | ctgtgagaaa | 2280 |
| gtccttgtca | gtgttctgaa | aactgggaat | taggaagtcg | acttccaatc | aagcttcaga | 2340 |
| tgacatgcga | catgcgttaa | gtttagaaat | aacgttagtg | tttctaattt | agcatcgtgt | 2400 |
| tggagtccta | attatgaaat | gacattaaga | aaattccatt | cctcagaatt | cttgtgcagt | 2460 |
| agcattgggt | agaaacacca | ttgtgttctg | tgacctgggg | tagggatgat | atctcaaaaa | 2520 |
| cgcatgctca | ggttgcccat | ggtgatagct | aaactgtctt | ctcaggagag | gagcaggctt | 2580 |
| tattaactgg | aactcaccag | atttcacaga | acattttgaa | gggcttagga | ttgtgagttt | 2640 |
| ggaggtagat | gccaagcaga | ggtaaacatt | ttgtataaca | gaagaaacat | atttgatatg | 2700 |
| ggagagagac | agaaatcttg | tggaaaactc | cagagccatc | aaagctggga | cagtgttaaa | 2760 |
| gacgagcacc | ctggaagtga | ggagccaagt | gtgggttttg | aggaacagat | atattaaggg | 2820 |
| ggattctcac | aaatgtttta | ttttgacaaa | tatcaataat | ttagaaaagt | tgcaagaata | 2880 |
| gtatagcaat | tattcatata | ccccttccat | atagtacaca | gaaaaagagg | gtatatattt | 2940 |
| taataaatat | ttgtgtatac | acattttgtg | tatagatagg | cagataaata | gataaagaga | 3000 |
| caaatgtgca | cctgtgtata | attttctgaa | ctgtttgaga | attggttgta | agcatcacga | 3060 |
| cacttcacca | ccaaatactt | cagcatgtgt | ctcctaagaa | caaggctgtt | ctctacatga | 3120 |
| ccacaacata | gttatttcac | ccagaaactt | aaacttgata | caatacaata | tctaatattc | 3180 |
| agtccatatt | caaatttctc | ctatcatcca | aataatatca | ttactaatct | ccaatataaa | 3240 |
| gagatttaaa | acatgttttc | catgttcaac | ataaatgtct | tctccatttt | tcttacaaaa | 3300 |
| tcatcaaaaa | caactacgtt | tcccatttat | acttttacac | cagtagttc | tttggaggaa | 3360 |
| cttgcacttg | tcccacatcc | agattggcag | gggataaaat | agaaataata | agagctggca | 3420 |
| gaagagaggc | tggttgatgc | tgattacatt | caaaataact | atttggagga | aaaagcactg | 3480 |
| attctgttcc | tggggtgt | | | | | 3498 |

<210> SEQ ID NO 13
<211> LENGTH: 3352
<212> TYPE: DNA
<213> ORGANISM: Homo sapiens

<400> SEQUENCE: 13

| | | | |
|---|---|---|---|
| ttagtctaaa | ttagggatac | acactcctcc | ctgagctcta | gacccctctc | tctaactttc | 60 |
| actggatatc | tccaccttga | tagttcacca | tgtctcaagt | tcagttttgc | tgaacctgaa | 120 |
| ctcataatct | tcaccttaaa | ctgcatcctc | atccagcatt | ccctaccttg | gtgaccatga | 180 |

```
tcaccaacct ctctcattgt aaaaacctgc ctaacacctt cccttccctc atcttccatc    240
tccagttcat tgctaagtgc tgatgttatt ctttaaatat gtcttaaagc aatctacttc    300
tctccatctt ggctcaggca ctttagtcca agctaccata acctatcctc tgaactactg    360
gcccacagaa tccactcttg cctctcccct aaaccattct ccaaaatgca ttccaagtat    420
tttttaaatt taactgaaaa tctgatcaca tcatgtgtct ttataaacac atcaatggct    480
tatccttaag ataaagacaa aagtcctaac atggcctata cagctctaca acatttttcc    540
atgcttattt ctcagctagc tacaatgttt tcctccatcc ctatgctcca gtcacaattc    600
cttcaatatg tccttgcttt gtcccacctc agagcttgcc acatgcagtt tcttctgact    660
cacatcccct tccttggaat gactgcctct cttttgatta gttaattttc tataatactg    720
cagacctcaa ctcaaatatc tcttgattcc ctcaaccacc agaccagatc agctctctca    780
ctatgcactt accatgtttt gaaattaata ctctctgaat tgtttatcac ctgtacctag    840
aatatagtgt atgatattta ttgggggggc tcaatatttt gagtggatga gtaaatatat    900
tacagatagc taattattca agatttcatg ttcacattat tgctaaaaat gtagatgaag    960
taaaagtaga ttgaaatagg aggatataaa catgttggcg ctcttttacat cacatacatg   1020 gattatgttt ttctttgttt gttttttagat gaagtcttgc gctgtcaccc aggctggacg   1080
gcagtggccc gagtgcacag gcaacctctg cctcccaggt tcaagcgatt ctcctccctc    1140
agcctcccga gtagctggga ttacaggagc ccaccaccaa gcccagctaa tttttgtatt    1200
tttagtagag acggggtttc gccatgttgg ccaggctggt ctgaactgct gacctcaggt    1260
gatccacccg cctcggcctc ccaaagtgct gggattacag gcgtgagcca ccatgcgcgg    1320
cccatggcat atgttatcag taatatgtaa gtatggcttc agtcaaagca aggaagttga    1380
aagtaacaat taaaaaaaaa aaagtcatca ggatccaaag ctgtggagaa aactcaacct    1440
ctgcctcctg ggttcaagca attctcctgc ctcagcctcc ctggtagctg ggattacagg    1500
tgcctgacac caccccagc taattttgt attttagta gagacatggt ttcaccatgt    1560
tggtcaggct ggtcttgaac tcctgacctc aggtgatcca cccacctcag cctcccaaag    1620
tgctgggatt acaggcgtga gccactttta gaaaatgttt tcatctatct caatacctca    1680
ctacccctcc tgatattcca tctataatag caacagttgt gaaatgcact agattctaac    1740
attaacacta gatccattaa gaacagagca gaagagagtc tggatacaca aatttcacaa    1800
ttattggctc ccatcaacat atctaactca agcataaagt tgtttcagca gtagtttaag    1860
gttggttact aatgcaacac ctctttgcat gcaatggccc attaaattat cttcaacttt    1920
aaaaggttcc tttgttttta atgcttata atgaacaaat atataccaat accttggcag    1980
aattcattaa cttaataact tcaatatgtt gttcatataa aaatttctgg taaatgagaa    2040
ctgtacatta ctgatgtgac aaggtacaca agccaatgtt gacataatgt tttcaaaatg    2100
gggtgtctgc tgtaactgaa ctaaatataa taactttatt caagaatgag tttcaatgat    2160
aggacaaaac ttgataaaat gaataaataa ataattatat gccagagttc agtaaaccct    2220
gtgtgtacac ctgaaaaagc tcaaacttgc ctagcacata tagagtccga attcagttgg    2280
gtttgtgtga acgggtagg ttgagcccta aaaagaggt agataaccca tataggcaga    2340
cttccttatt ttatttattt ttttctgctt cagcctcctg agtagctggg actacaggtg    2400
tgtgccacca cgtctggcta attttgtttg ttttttagtag agatggggtt tcaccatatt    2460
ggccaggctg gtctcgaact cctgaccttg tgatctgcgc cctcggcct cccaaagtgc    2520 tgggattaca ggcgtgagcc actgcgcctc gccaacttcc ttattttaaa tgccatttcc    2580
```

```
cactaaaaat aaaaccagta attctttgaa aaaaagttaa tattatgtat aggactggaa    2640
gtatataaga taaaactgga atatattgtc ataccagaaa tcaaagattt tgtcaaagac    2700
taatagttcc atgtcaaaaa gattcactaa tcaatttgca gaggctccca ctggccaaag    2760
atagagcttg atcatcaaca ggaataataa ctataatggg ttaaaacata gcaattatgt    2820
ttaaatctat aggtttatag taataatgtt aaaatcatta gtcacctttg aaagatgcta    2880
cgactcttta atccatcttg aattaatttt tgtataaggt gtaaggaagg gatccagttt    2940
cagctttcta catatggcta gccagttttc ccagcaccat ttattcaata gggaatcctt    3000
tccccattgc ttgtttttct caggtttgtc aaagatcaga tagttgtaga tatgcggtgt    3060
tatttctgag ggctctgttc tgttccattg atctatatct ctgttttggt accagtacca    3120
tgctgttttg gttactgtag ccttgtagta tagtttgaag tcaggttgca tgatgcctcc    3180
agctttgttc ttttggctta ggattgactt ggcaatgcgg gctccttttt ggttccatat    3240
gaactttaaa gtagtttttt ccaattctgt gaagaaagtc attggcagct tgatggggat    3300
gacattgaat ctataaatta ccttgggcag tatggccatt ttcacgatat tg           3352
```

```
<210> SEQ ID NO 14
<211> LENGTH: 40
<212> TYPE: DNA
<213> ORGANISM: Artificial
<220> FEATURE:
<223> OTHER INFORMATION: beta-actin promoter primer F

<400> SEQUENCE: 14
gccccagtga cagctccgaa agctccctta cagggcaaag                          40

<210> SEQ ID NO 15
<211> LENGTH: 30
<212> TYPE: DNA
<213> ORGANISM: Artificial
<220> FEATURE:
<223> OTHER INFORMATION: beta-actin promoter primer R

<400> SEQUENCE: 15
ggtgagctgc gagaatagcc gggcgcgctg                                     30

<210> SEQ ID NO 16
<211> LENGTH: 32
<212> TYPE: DNA
<213> ORGANISM: Artificial
<220> FEATURE:
<223> OTHER INFORMATION: gamma-actin promoter primer F

<400> SEQUENCE: 16
aattccagca gcgcacaagg aaaccgtagt gc                                  32

<210> SEQ ID NO 17
<211> LENGTH: 30
<212> TYPE: DNA
<213> ORGANISM: Artificial
<220> FEATURE:
<223> OTHER INFORMATION: gamma-actin promoter primer R

<400> SEQUENCE: 17
tgcgacctgc ccggaaaagg atggactcag                                     30

<210> SEQ ID NO 18
<211> LENGTH: 31
<212> TYPE: DNA
```

```
<213> ORGANISM: Artificial
<220> FEATURE:
<223> OTHER INFORMATION: UBC promoter primer F

<400> SEQUENCE: 18
ccatgcctcc ctgttggcat caagtaggac c                                    31

<210> SEQ ID NO 19
<211> LENGTH: 41
<212> TYPE: DNA
<213> ORGANISM: Artificial
<220> FEATURE:
<223> OTHER INFORMATION: UBC promoter primer R

<400> SEQUENCE: 19
tgtctaacaa aaaagccaaa aacggccaga atttagcgga c                         41

<210> SEQ ID NO 20
<211> LENGTH: 36
<212> TYPE: DNA
<213> ORGANISM: Artificial
<220> FEATURE:
<223> OTHER INFORMATION: GAPDH promoter primer F

<400> SEQUENCE: 20
cacaatgtca atagcgtcac agttgagaaa acctgc                               36

<210> SEQ ID NO 21
<211> LENGTH: 24
<212> TYPE: DNA
<213> ORGANISM: Artificial
<220> FEATURE:
<223> OTHER INFORMATION: GAPDH promoter primer R

<400> SEQUENCE: 21
ggtgtctgag cgatgtggct cggc                                            24

<210> SEQ ID NO 22
<211> LENGTH: 35
<212> TYPE: DNA
<213> ORGANISM: Artificial
<220> FEATURE:
<223> OTHER INFORMATION: RPS21 promoter primer F

<400> SEQUENCE: 22
tttgagacgc agtcttgctc tgtcgcccag gctgg                                35

<210> SEQ ID NO 23
<211> LENGTH: 30
<212> TYPE: DNA
<213> ORGANISM: Artificial
<220> FEATURE:
<223> OTHER INFORMATION: RPS21 promoter primer R

<400> SEQUENCE: 23
ttcgaggctg ggctgcgcct ggggagtcac                                      30

<210> SEQ ID NO 24
<211> LENGTH: 30
<212> TYPE: DNA
<213> ORGANISM: Artificial
<220> FEATURE:
<223> OTHER INFORMATION: RPL41 promoter primer F

<400> SEQUENCE: 24
gaggcgggag aatcgcttgt attcaggagg                                      30
```

<210> SEQ ID NO 25
<211> LENGTH: 29
<212> TYPE: DNA
<213> ORGANISM: Artificial
<220> FEATURE:
<223> OTHER INFORMATION: RPL41 promoter primer R

<400> SEQUENCE: 25
ggcgcagagg tttctacagg gaaagagag                                29

<210> SEQ ID NO 26
<211> LENGTH: 39
<212> TYPE: DNA
<213> ORGANISM: Artificial
<220> FEATURE:
<223> OTHER INFORMATION: RPL32 promoter primer F

<400> SEQUENCE: 26
cttggcattg acttagacac cctaggaatc taacttgag                     39

<210> SEQ ID NO 27
<211> LENGTH: 24
<212> TYPE: DNA
<213> ORGANISM: Artificial
<220> FEATURE:
<223> OTHER INFORMATION: RPL32 promoter primer R

<400> SEQUENCE: 27
gatgcctttt ggggaagaag cggc                                     24

<210> SEQ ID NO 28
<211> LENGTH: 31
<212> TYPE: DNA
<213> ORGANISM: Artificial
<220> FEATURE:
<223> OTHER INFORMATION: RPL8 promoter primer F

<400> SEQUENCE: 28
tgtgagcaac agcgggcaca ggacaccctt c                             31

<210> SEQ ID NO 29
<211> LENGTH: 32
<212> TYPE: DNA
<213> ORGANISM: Artificial
<220> FEATURE:
<223> OTHER INFORMATION: RPL8 promoter primer R

<400> SEQUENCE: 29
ggcgacgggt cctgggggcg actcacgatt ag                            32

<210> SEQ ID NO 30
<211> LENGTH: 39
<212> TYPE: DNA
<213> ORGANISM: Artificial
<220> FEATURE:
<223> OTHER INFORMATION: RPLP1 promoter primer F

<400> SEQUENCE: 30
ggggcagtgg aatttgtctg aagtaactgt tgaatccac                     39

<210> SEQ ID NO 31
<211> LENGTH: 22
<212> TYPE: DNA
<213> ORGANISM: Artificial
<220> FEATURE:

<223> OTHER INFORMATION: RPLP1 promoter primer R

<400> SEQUENCE: 31
ggcgcgggcg agtgtagggc tg                                    22

<210> SEQ ID NO 32
<211> LENGTH: 18
<212> TYPE: DNA
<213> ORGANISM: Artificial
<220> FEATURE:
<223> OTHER INFORMATION: EF1-alpha promoter primer F

<400> SEQUENCE: 32
gtgcccgtca gtgggcag                                         18

<210> SEQ ID NO 33
<211> LENGTH: 21
<212> TYPE: DNA
<213> ORGANISM: Artificial
<220> FEATURE:
<223> OTHER INFORMATION: EF1-alpha promoter primer R

<400> SEQUENCE: 33
tcacgacacc tgaaatggaa g                                     21

<210> SEQ ID NO 34
<211> LENGTH: 39
<212> TYPE: DNA
<213> ORGANISM: Artificial
<220> FEATURE:
<223> OTHER INFORMATION: RPL32 (-1918 - 504) primer F

<400> SEQUENCE: 34
cttggcattg acttagacac cctaggaatc taacttgag                  39

<210> SEQ ID NO 35
<211> LENGTH: 25
<212> TYPE: DNA
<213> ORGANISM: Artificial
<220> FEATURE:
<223> OTHER INFORMATION: RPL32 (-1918 - 504) primer R

<400> SEQUENCE: 35
cgacctacag ctcgtctttc cttgg                                 25

<210> SEQ ID NO 36
<211> LENGTH: 39
<212> TYPE: DNA
<213> ORGANISM: Artificial
<220> FEATURE:
<223> OTHER INFORMATION: RPL32 (-1918 - 94) primer F

<400> SEQUENCE: 36
cttggcattg acttagacac cctaggaatc taacttgag                  39

<210> SEQ ID NO 37
<211> LENGTH: 24
<212> TYPE: DNA
<213> ORGANISM: Artificial
<220> FEATURE:
<223> OTHER INFORMATION: RPL32 (-1918 - 94) primer R

<400> SEQUENCE: 37
gccagatgaa tcccgcagga atgc                                  24

```
<210> SEQ ID NO 38
<211> LENGTH: 24
<212> TYPE: DNA
<213> ORGANISM: Artificial
<220> FEATURE:
<223> OTHER INFORMATION: RPL32 (-691 - 1302) primer F

<400> SEQUENCE: 38
agtagctcgt gcccgtaatc ccag                                              24

<210> SEQ ID NO 39
<211> LENGTH: 24
<212> TYPE: DNA
<213> ORGANISM: Artificial
<220> FEATURE:
<223> OTHER INFORMATION: RPL32 (-691 - 1302) primer R

<400> SEQUENCE: 39
gatgcctttt ggggaagaag cggc                                              24

<210> SEQ ID NO 40
<211> LENGTH: 35
<212> TYPE: DNA
<213> ORGANISM: Artificial
<220> FEATURE:
<223> OTHER INFORMATION: RPL32 (-137 - 1302) primer F

<400> SEQUENCE: 40
ctcagaattt ttgcggcatt attttttgac gtgtc                                  35

<210> SEQ ID NO 41
<211> LENGTH: 24
<212> TYPE: DNA
<213> ORGANISM: Artificial
<220> FEATURE:
<223> OTHER INFORMATION: RPL32 (-137 - 1302) primer R

<400> SEQUENCE: 41
gatgcctttt ggggaagaag cggc                                              24

<210> SEQ ID NO 42
<211> LENGTH: 24
<212> TYPE: DNA
<213> ORGANISM: Artificial
<220> FEATURE:
<223> OTHER INFORMATION: RPL32 (-691 - 504) primer F

<400> SEQUENCE: 42
agtagctcgt gcccgtaatc ccag                                              24

<210> SEQ ID NO 43
<211> LENGTH: 25
<212> TYPE: DNA
<213> ORGANISM: Artificial
<220> FEATURE:
<223> OTHER INFORMATION: RPL32 (-691 - 504) primer R

<400> SEQUENCE: 43
cgacctacag ctcgtctttc cttgg                                             25

<210> SEQ ID NO 44
<211> LENGTH: 39
<212> TYPE: DNA
<213> ORGANISM: Artificial
<220> FEATURE:
<223> OTHER INFORMATION: RPL32 (-1918- -1302) primer F
```

```
<400> SEQUENCE: 44
cttggcattg acttagacac cctaggaatc taacttgag                              39

<210> SEQ ID NO 45
<211> LENGTH: 34
<212> TYPE: DNA
<213> ORGANISM: Artificial
<220> FEATURE:
<223> OTHER INFORMATION: RPL32 (-1918- -1302) primer R

<400> SEQUENCE: 45
gctccggctc ttttaaataa aataaagaca cgtc                                   34

<210> SEQ ID NO 46
<211> LENGTH: 21
<212> TYPE: DNA
<213> ORGANISM: Artificial
<220> FEATURE:
<223> OTHER INFORMATION: RPL32 (-1918- -1302) primer 2 F

<400> SEQUENCE: 46
ctcttcctcg gcgctgccta c                                                 21

<210> SEQ ID NO 47
<211> LENGTH: 24
<212> TYPE: DNA
<213> ORGANISM: Artificial
<220> FEATURE:
<223> OTHER INFORMATION: RPL32 (-1918- -1302) primer 2 R

<400> SEQUENCE: 47
gatgcctttt ggggaagaag cggc                                              24
```

NUCLEIC ACID FRAGMENTS FROM A RIBOSOMAL PROTEIN PROMOTER FOR ENHANCING GENE EXPRESSION

CROSS-REFERENCE TO RELATED APPLICATIONS

This application is the National Phase of International Patent Application No. PCT/NL2011/050593, filed Aug. 31, 2011, published as WO 2012/030218, which claims the benefit to U.S. Provisional Application No. 61/379,025, filed Sep. 1, 2010. The contents of these applications are herein incorporated by reference in their entirety.

FIELD OF THE INVENTION

The present invention relates to the field of molecular biology and biotechnology. More specifically the present invention relates to means and methods for improving the selection of host cells with high expression levels.

BACKGROUND OF THE INVENTION

Bioactive proteins are produced in various host cells, ranging from bacteria and yeast to mammalian cells. Mammalian cells as host cell are preferred when the protein requires certain posttranslational modifications, such as glycosylation to function properly. In general, proteins produced in mammalian cells are expressed from a so-called 'transgene' encoding the protein of interest. To ensure that the right, protein-producing cell is selected, the transgene coding for the gene of interest is coupled to a second transgene encoding a selectable marker that most often is placed on the same vector. A common problem is that the stringency of selection is often low, meaning that the cell has to make only very small amounts of selection protein in order to survive the toxic selective conditions. If only a limited expression of the selectable marker protein is required for selection of the cells, this also has implications for the expression levels of the transgenic protein. Low expression levels of selectable marker protein will usually be accompanied by low expression of the transgene protein. This is obviously an unwanted side effect of low selection stringency.

An improvement in selection stringency is seen with the Zeocin selection marker. This is because the Zeocin selection protein does not act as an enzyme but rather stoichiometrically binds two Zeocin selection molecules without further processing them. As a consequence, the cell must produce much more molecules of a stoichiometric selectable marker such the Zeocin selection protein as compared to an enzymatic selectable marker protein of which a single molecule is capable of katalysing inactivation many molecules of the selection agent. When coupled to a gene of interest, the higher stringency of the stoichiometric selectable marker usually results in higher levels of mRNA and/or expression of the gene product of interest.

Because stably transfected clones can only be selected for the expression levels of the selection marker and not for the expression level of the gene of interest, it is preferred that the expression of the gene of interest is directly linked to the expression level of the selection marker. One way of achieving this by placing an IRES (Internal Ribosome Entry Site) sequence between the gene of interest and the gene encoding the selection marker. This creates a single bicistronic mRNA from which both the gene product of interest and the selection protein are translated (Rees et al., 1996, Biotechniques 20: 102-110). A high level of expression of the selectable marker, e.g. by using a high stringency marker, is thereby directly coupled to a high level of expression of the gene product of interest. This is an accepted and often employed method procedure for selection of clones that express relatively high levels of the gene product of interest (see e.g. WO 03/106684, WO 2006/005718 and WO 2007/096399).

The stringency of selection can be further increased by using selectable markers that harbor mutations that attenuate but do not completely destroy the activity of the selection marker. Under the same selective conditions, higher levels of the impaired selection protein will be required as compared to the wild type selection protein. When coupled to the gene of interest through an IRES sequence, the higher mRNA levels of the impaired selection marker warrant that there will also be more mRNA of the gene of interest available for translation. (see e.g. WO 01/32901 and WO 2006/048459)

In another example of high selection stringency systems the translation initiation of the selection marker protein is severely impaired by using sub-optimal, non-ATG codons for initiation of translation of the selectable marker protein. These selection systems have been termed STAR-Select (Otte et al. (2007) Biotechnol. Progr. 23(4):801-807; WO 2006/048459 and WO 2007/096399).

Recently, the present inventors developed a novel stringent selection principle whereby translation initiation of the selection marker protein is severely impaired by placing a coding sequence for a short peptide immediately upstream of a selection marker, thereby requiring the ribosome to re-initiate translation at the translation initiation codon of the selectable marker protein (co-pending application PCT/NL2010/050367). In this system, the stringency of selection can be fined tuned by increasing the length of the short peptide: when the short peptide becomes longer, the translation machinery will have increasing difficulties to re-initiate at the translation initiation codon of the selectable marker protein. In combination with the Zeocin selectable marker protein this stringent selection system has been dubbed the "ppZeo selection system" (pp=petite peptides).

However, one problem with the high-stringency selection systems is that the number of colonies obtained after transformation is significantly reduced, even down to a level that hardly any colonies are obtained. This problem has been addressed by the inclusion in expression vectors of expression enhancing sequences such as Locus Control Regions (LCR; Needham et al., 1995. Protein Expr Purif 6:124-131) or STARs (WO 03/004704; WO 03/106674; WO 03/106684; WO 2006/005718; WO 2006/048459 and WO 2007/096399). WO 2006/123097 discloses that also DNA fragments from the promoter region of the genes coding for the ribosomal proteins S3 and S11 (RPS3 and RPS11, respectively), when linked to an expression cassette comprising an heterologous promoter, are capable of increasing transcription from the heterologous promoter in the cassette.

There is however, still a need in the art for improved means and methods for high stringency selection of mammalian cells to achieve high production of colonies and/or high expression levels of gene products of interest. In particular, there is still a need for further improved DNA fragments that are capable of increasing expression of expression cassettes comprising highly stringent selectable markers.

DESCRIPTION OF THE INVENTION

Definitions

A "nucleic acid construct" is herein understood to mean a man-made nucleic acid molecule resulting from the use of recombinant DNA technology. A nucleic acid construct is a nucleic acid molecule, either single- or double-stranded, which has been modified to contain segments of nucleic acids, which are combined and juxtaposed in a manner, which would not otherwise exist in nature. A nucleic acid construct usually is a "vector", i.e. a nucleic acid molecule which is used to deliver exogenously created DNA into a host cell. Common types of vectors may be derived from naturally occurring plasmids, phages and viruses. Vectors usually comprise further genetic elements to facilitate their use in molecular cloning, such as e.g. selectable markers, multiple cloning sites and replication origins functional in one or more host cells and the like.

The term "expression" is typically used to refer to the production of a specific nucleic acid product (preferably a specific RNA product) or a specific protein or proteins, in a cell. In the case of RNA products, it refers to the process of transcription. In the case of proteins, it refers to the processes of transcription, translation and optionally post-translational modifications. In the case of secreted proteins, it refers to the processes of transcription, translation, and optionally post-translational modification (e.g., glycosylation, disulfide bond formation, etc.), followed by secretion. In the case of multimeric proteins, it optionally includes assembly of the multimeric structure from the polypeptide monomers.

One type of nucleic acid construct is an "expression construct" or "expression cassette" or "expression vector". These terms refer to nucleotide sequences that are capable of effecting expression of a gene in host cells or host organisms compatible with such sequences. Expression constructs, expression cassettes or expression vectors typically include at least suitable transcription regulatory sequences and optionally, 3' transcription termination signals. Additional factors necessary or helpful in effecting expression may also be present, such as expression enhancer elements.

The term "monocistronic gene" is defined as a gene capable of providing a RNA molecule that encodes one gene product. A "multicistronic transcription unit", also referred to as multicistronic gene, is defined as a gene capable of providing an RNA molecule that encodes at least two gene products. The term "bicistronic gene", also referred to as "dicistronic gene", is defined as a gene capable of providing a RNA molecule that encodes two gene products. A bicistronic gene is therefore encompassed within the definition of a multicistronic gene.

The term peptide herein refers to any molecule comprising a chain of amino acids that are linked in peptide bonds. The term peptide thus includes oligopeptides, polypeptides and proteins, including multimeric proteins, without reference to a specific mode of action, size, 3-dimensional structure or origin. A "polypeptide" as used herein usually comprises at least five amino acids linked by peptide bonds. The terms "protein" or "polypeptide" are used interchangeably. A "fragment" or "portion" of a protein may thus still be referred to as a "protein". An "isolated protein" is used to refer to a protein which is no longer in its natural environment, for example in vitro or in a recombinant (fungal or plant) host cell. The term peptide also includes post-translation modifications of peptides, e.g. glycosylations, acetylations, phosphorylations, and the like. A "gene product" of interest or a "transcription unit" as used in the present invention can comprise chromosomal DNA, cDNA, artificial DNA, combinations thereof, and the like. A "gene product of interest" can be any gene product, such as for example a protein, a RNAi, shRNA and the like. Non-limiting examples of a protein of interest are enzymes, immunoglobulin chains, therapeutic proteins like anti-cancer proteins or diagnostic proteins. Transcription units comprising several cistrons are transcribed as a single mRNA.

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence is designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in eukaryotic (host) cells.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

As used herein, an "internal ribosome entry site" or "IRES" refers to an element that promotes direct internal ribosome entry to the translation initiation codon (also known as start codon) of a cistron (a protein encoding region), thereby leading to the cap-independent translation of the gene. See, e.g., Jackson R J, Howe 11 M T, Kaminski A (1990) Trends Biochem Sci 15 (12): 477-83) and Jackson R J and Kaminski, A. (1995) RNA 1 (10): 985-1000. The present invention encompasses the use of any cap-independent translation initiation sequence, in particular any IRES element that is able to promote direct internal ribosome entry to the initiation codon of a cistron. "Under translational control of an IRES" as used herein means that translation is associated with the IRES and proceeds in a cap-independent manner. As used herein, the term "IRES" encompasses functional variations of IRES sequences as long as the variation is able to promote direct internal ribosome entry to the initiation codon of a cistron.

As used herein, "cistron" refers to a segment of a polynucleotide sequence (DNA) that contains all the information for production of single polypeptide chain.

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention is ClustalW (1.83) using a blosum matrix and default settings (Gap opening penalty: 10; Gap extension penalty: 0.05). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

Nucleotide sequences encoding a nucleic acid sequence of the invention may also be defined by their capability to hybridise with the specific nucleotide sequences disclosed herein or parts thereof, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

The adaptiveness of a nucleotide sequence encoding a gene product of interest to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51).

A preferred nucleic acid according to the invention is a nucleic acid construct, wherein the nucleotide sequence encoding the gene product of interest is operably linked to a promoter and optionally other regulatory elements such as e.g. terminators, enhancers, polyadenylation signals, signal sequences for secretion and the like. Such nucleic acid constructs are particularly useful for the production of the gene product of interest using recombinant techniques in which a nucleotide sequence encoding the gene product of interest is expressed in suitable host cells such as described in Ausubel et al., "Current Protocols in Molecular Biology", Greene Publishing and Wiley-Interscience, New York (1987) and in Sambrook and Russell (2001) Molecular Cloning: A Laboratory Manual (3$^{rd}$ edition), Cold Spring Harbor Laboratory, Cold Spring Harbor Laboratory Press, New York). As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

DETAILED DESCRIPTION OF THE INVENTION

The present inventors found that particular sequences of the promoter region of the ribosomal protein L32 genes (also known as 60S ribosomal protein L32; PP9932; RPL32) (SEQ ID NO:1) and parts thereof as further defined herein, when placed in an expression vector (comprising, operably linked, a promoter, a nucleotide sequence encoding a selectable marker functional in a eukaryotic host cell and optionally an open reading frame encoding a gene product of interest) are capable of increasing the number of colonies that are formed under selection conditions, preferably stringent selection conditions, as compared to the same expression vector without these particular sequences under stringent selection conditions, and preferably also as compared to the same expression vector without the RPL32 sequences under stringent selection conditions, but flanked by STAR 6/67/7 elements as described in WO 2006/048459 and WO 2007/096399.

RPL32 encodes a ribosomal protein that is a component of the 60S subunit. The protein belongs to the L32E family of ribosomal proteins and is located in the cytoplasm. The RPL32 gene itself as well as its promoter region are well conserved in chimpanzee, dog, cow, mouse, rat, zebrafish, *Drosophila*, mosquito, *Caenorhabditis elegans, Saccharomyce cerevisiae, Arabidobsis thaliana*, rice and *Plasmodium falciparum*.

A nucleic acid construct according to the invention, i.e. an expression construct comprising sequences from an RPL32 promoter region, can be used to select cells, preferably eukaryotic cells, more preferably plant cells or mammalian cells, that have high expression levels of a gene product of interest (as compared to a control that does not have the nucleotide sequence of the invention) and/or that result in a high number of stable colonies (as compared to a control that does not have the nucleotide sequence of the invention), by selecting for the expression of the selectable marker. Subsequently or simultaneously, one or more of the selected cell(s) can be identified, and further used for expression of high levels of the gene product of interest.

The present invention is based on an impaired efficiency of expression of a selectable marker. Expression of a selectable marker can be detected using routine methods known to the person skilled in the art, e.g. by determining the number of surviving colonies after a normal selection period. As is well known to the person skilled in the art there are a number of parameters that indicate the expression level of a selection marker polypeptide such as, the maximum concentration of selection agent to which cells are still resistant, number of surviving colonies at a given concentration, growth speed (doubling time) of the cells in the presence of selection agent, combinations of the above, and the like. By using the present invention, cells can be identified that have high levels of expression of the selectable marker and/or that provide a high number of colonies of cells.

In a first aspect, the present invention relates to a nucleic acid fragment comprising or consisting of a nucleotide sequence having at least 80, 85, 87, 90, 91, 92, 93, 94, 95, 96, 97, 98 or 99% sequence identity (preferably, over its entire length) with a nucleotide sequence, which, i) comprises at least 1001, 1187, 1195, 1250, 1500, 1750, 2000, 2500, 3000 or all of the contiguous nucleotides from SEQ ID NO:1; and, ii) includes nucleotide residues 1782 to 1921 of SEQ ID NO:1 (position 1921 in SEQ ID NO:1 being the transcription start site). Preferably, the nucleic acid fragment, when directly flanking an expression cassette having the nucleotide sequence of SEQ ID NO: 2 upstream of the expression cassette, produces at least 50, 75, 90, 100, 101, 110, 125 or 150% of number of colonies obtained with the same expression cassette when flanked with STARs 7 and 67 upstream of the expression cassette and STAR 7 downstream of the expression cassette (SEQ ID NO: 3), when tested under the conditions of Example 1.

Preferably, the nucleic acid fragment is a fragment comprising or consisting of a nucleotide sequence having at least 80, 85, 87, 90, 91, 92, 93, 94, 95, 96, 97, 98 or 99% sequence identity (preferably, over its entire length) with a nucleotide sequence, which, i) comprises at least 1187, 1195, 1250, 1500, 1750, 2000, 2500, 3000 or all of the contiguous nucleotides from SEQ ID NO:1 and ii), includes nucleotide residues 1236 to 2423 of SEQ ID NO:1 and which fragment otherwise is as defined above. More preferably, the nucleic acid fragment is a fragment comprising or consisting of a nucleotide sequence having at least 80, 85, 87, 90, 91, 92, 93, 94, 95, 96, 97, 98 or 99% sequence identity (preferably, over its entire length) with a nucleotide sequence, which, i) comprises at least 1750, 2000, 2500, 3000 or all of the contiguous nucleotides from SEQ ID NO:1 and ii), includes nucleotide residues 1236 to 3220 or nucleotide residues 1 to 2423 of SEQ ID NO:1; and which fragment otherwise is as defined above. Most preferably, the nucleic acid fragment is a fragment selected from the group consisting of nucleic acid fragments having at least 80, 85, 87, 90, 91, 92, 93, 94, 95, 96, 97, 98 or 99% sequence identity (preferably, over its entire length) with a nucleotide sequence comprising or consisting of nucleotide residues 1236 to 2423, 1782 to 3220, 1236 to 3220, 1 to 2013, 1 to 2423, or 1 to 3220 of SEQ ID NO:1.

The nucleic acid fragment preferably is an isolated nucleic acid fragment, which is understood to mean a fragment isolated or purified from its natural environment. Preferably, the nucleic acid fragment is from a mammalian genome, more preferably from a primate or rodent genome, and most preferably the nucleic acid fragment is from a human, mouse, rat, hamster, bovine, chicken, dog, cavia, pig or rabbit genome. A preferred nucleic acid fragment is from SEQ ID NO: 1. In a preferred embodiment, the nucleic acid fragment has a length of less than 30,000 nucleotide residues, more preferably less than 20,000, 10,000, 5000, 4500, 3750, 3600, 3500, 3000, 2750, 2500, 2000, 1750 or 1500 nucleotide residues.

In a second aspect the invention relates to a nucleic acid construct comprising a nucleic acid fragment as defined above, wherein the fragment is linked to at least one nucleotide that does not naturally occur immediately adjacent to the fragment in the genome from which the fragment is derived. Preferably the nucleic acid construct comprises more than one non-naturally occurring nucleotide attached to the fragment, such as e.g. a stretch of nucleotides comprising one or more restriction sites or adapter sequences that are complementary to PCR primers.

More preferably, in the nucleic acid construct comprising a nucleic acid fragment as defined above, the fragment is linked to an expression cassette. The expression cassette preferably comprises at least a promoter operably linked to a nucleotide sequence encoding a gene product of interest. The promoter may be a promoter as defined below. The expression cassette may further comprise a nucleotide sequence encoding a selectable marker functional in a eukaryotic host cell e.g. as described below.

A nucleic acid fragment according to the invention functions "in cis". Hence, it is preferred that in the nucleic acid construct, a nucleic acid fragment of the invention is present within 5 kb, more preferably within 2 kb, still more preferably within 1 kb, most preferably within 500 bp from the expression cassette or more preferably from the most 5' promoter in the expression cassette (preferably, when present upstream of the cassette). If a nucleic acid fragment of the invention is present downstream of the expression cassette in the construct, the nucleic acid fragment of the invention is present within 5 kb, more preferably within 2 kb, still more preferably within 1 kb, most preferably within 500 bp from the expression cassette or more preferably from the most 3' transcription terminator sequence and/or polyadenylation site in the expression cassette. Thus, a nucleic acid construct may comprise a nucleic acid fragment of the invention either downstream or upstream of an expression cassette. Alternatively, a nucleic acid construct may comprise a nucleic acid fragment of the invention both downstream and upstream of the expression cassette. In the nucleic acid construct the nucleic acid fragments according to the invention that are present up- and downstream of the expression cassette may be independently selected from the nucleic acid fragments as defined above. Thus, in the nucleic acid construct, the nucleic acid fragment upstream of the expression cassette may be different from the nucleic acid fragment downstream of the expression cassette. Alternatively, in the nucleic acid construct, the nucleic acid fragments up- and downstream of the expression cassette may be (essentially) identical.

Furthermore, in the nucleic acid construct it is preferred that the one or more nucleic acid fragments according to the invention are linked to the expression cassette in an orientation so that transcription from the promoters in the fragments is in the same direction as transcription from the promoter in the expression cassette.

A "expression cassette" as used herein is a nucleotide sequence comprises at least a promoter functionally linked to a nucleotide sequence encoding a gene product of interest, of which expression is desired. Preferably, the expression cassette further contains transcription termination and polyadenylation sequences. Other regulatory sequences such as enhancers may also be included in the expression cassette. In addition to the nucleotide sequence encoding a gene product of interest, the expression cassette preferably also comprises a nucleotide sequence encoding a selectable marker for selection of host cells comprising the expression cassette. In a preferred embodiment, the nucleotide sequence encoding the gene product of interest and the nucleotide sequence encoding a selectable marker are part of the same (multicistronic) transcription unit in the expression cassette. Hence, the invention provides for an expression cassette preferably comprising in a 5' to 3' direction, and operably linked: a) 5'- a promoter—a nucleotide sequence encoding a selectable marker—an open reading frame encoding a gene product of interest—optionally, transcription termination and/or polyadenylation sequences -3', or b) 5'- a promoter— an open reading frame encoding a gene product of interest—a nucleotide sequence encoding a selectable marker— optionally, transcription termination and/or polyadenylation sequences -3'. The promoter, as well as the other regulatory sequences, must be capable of functioning in the eukaryotic host cell in question, i.e. they must be capable of driving transcription of the gene product of interest and the selectable marker. The promoter is thus operably linked to the transcription unit(s) comprising the selectable marker and the open reading frame encoding a gene product of interest. The expression cassette may optionally further contain other elements known in the art, e.g. splice sites to comprise introns, and the like. In some embodiments, an intron is present behind the promoter and before the sequence encoding an open reading frame.

In other embodiments, an IRES may be present in the transcription unit that contains the selectable marker coding sequence and the sequence encoding the gene product of interest, which IRES may be present in between the open reading frames of the selectable marker and the gene product of interest. Internal ribosome binding site (IRES) elements are known from viral and mammalian genes (Martinez-Salas, 1999, Curr Opin Biotechnol 10: 458-464), and have also been identified in screens of small synthetic oligonucleotides (Venkatesan & Dasgupta, 2001 Mol Cell Biol 21: 2826-2837). The IRES from the encephalomyocarditis virus has been analyzed in detail (Mizuguchi et al., 2000, Mol Ther 1: 376-382). An IRES is an element encoded in DNA that results in a structure in the transcribed RNA at which eukaryotic ribosomes can bind and initiate translation. An IRES permits two or more proteins to be produced from a single RNA molecule (the first protein is translated by ribosomes that bind the RNA at the cap structure of its 5' terminus, (Martinez-Salas, 1999, supra). Thus, the invention provides an expression cassette preferably comprising in a 5' to 3' direction: 5'- a promoter—an open reading frame encoding a gene product of interest—an IRES—a selectable marker—optionally, transcription termination and/or polyadenylation sequences -3' or 5'- promoter—a selectable marker—an IRES—an open reading frame encoding a gene product of interest—optionally, transcription termination and/or polyadenylation sequences -3'. A promoter to be applied in the expression cassettes comprised in the nucleic acid constructs of the invention preferably is functional in a eukaryotic host cell, more preferably, the promoter is functional in a plant or animal host cell, still more preferably the promoter is functional in a vertebrate host cell and most preferably in a mammalian host cell, for initiating transcription of the transcription unit. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000, Mol. Biotechnol 16: 151-160). According to the present invention, strong promoters that give high transcription levels in the eukaryotic cells of choice are preferred. Some well-known and frequently used strong promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable e.g. from pcDNA, Invitrogen), promoters derived from Simian Virus 40 (SV40) (Das et al, 1985, Prog Nucleic Acid Res Mol Biol. 32: 217-36), and the like. Suitable strong promoters can also be derived from eukaryotic cells, such as methallothionein (MT) promoters, an elongation factor (EF-1α) promoter, an ubiquitin C or UB6 promoter (Gill et al., 2001, Gene Therapy 8: 1539-1546; Schorpp et al, 1996, Nucleic Acids Res 24: 1787-8), an actin promoter such as a β-actin promoter, e.g. a hamster or human β-actin promoter (SEQ ID NO: 10), an immunoglobulin promoter, a heat shock promoter and the like. Testing for promoter function and strength of a promoter is a matter of routine for a person skilled in the art, and in general may for instance encompass cloning a reporter gene such as lacZ, luciferase, GFP, etc. behind the promoter sequence, and test for expression of the reporter gene. Of course, promoters may be altered by deletion, addition, mutation of sequences therein, and tested for functionality, to find new, attenuated, or improved promoter sequences. Preferred promoters for use in the present invention are a human β-actin promoter, a CMV promoter, an SV40 promoter, an ubiquitin C promoter or an EF1-alpha promoter.

An open reading frame is herein understood as a nucleotide sequence comprising in a 5' to 3' direction 1) a translation initiation codon, 2) one or more codons coding for a gene product of interest, preferably a protein, and 3) a translation stop codon, whereby it is understood that 1), 2) and 3) are operably linked in frame. The open reading frame will thus consist of a multiple of 3 nucleotides (triplets).

A gene product of interest according to the invention can be any gene product, e.g. a protein. A gene product of interest may be a monomeric protein or a (part of a) multimeric protein. A multimeric protein comprises at least two polypeptide chains. Non-limiting examples of a protein of interest according to the invention are enzymes, hormones, immunoglobulins or chains or fragments thereof, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

A gene product of interest may be from any source, and in certain embodiments is a mammalian protein, an artificial protein (e.g. a fusion protein or mutated protein), and preferably is a human protein.

In a preferred embodiment, a nucleotide sequence encoding a gene product of interest is codon optimized for the host cell in which the peptide of interest is to be expressed, using the codon adaptation index of the host cell. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al., Gene. 1997, 199:293-301; zur Megede et al., Journal of Virology, 2000, 74: 2628-2635). Preferably, a nucleotide sequence encoding a gene product of interest has a CAI of at least 0.5, 0.6, 0.7, 0.8, 0.9 or 0.95.

In one embodiment, a nucleic acid construct of the present invention is used when the ultimate goal is not the production of a polypeptide of interest, but rather an RNA molecule, e.g. for producing increased quantities of RNA from an expression cassette, which may be used for purposes of regulating other genes (e.g. RNAi, antisense RNA), gene therapy, in vitro protein production, etc.

For the production of multimeric proteins, two or more nucleic acid constructs according to the invention can be used. For example, both expression cassettes can be multicistronic nucleic acid constructs, each coding for a different selectable marker protein, so that selection for both expression cassettes is possible. This embodiment is advantageous, e.g. for the expression of the heavy and light chain of immunoglobulins such as antibodies. It will be clear that both nucleic acid constructs may be placed on one nucleic acid molecule or both may be present on a separate nucleic acid molecule, before they are introduced into host cells. An advantage of placing them on one nucleic acid molecule is that the two nucleic acid constructs are present in a single predetermined ratio (e.g. 1:1) when introduced into host cells. On the other hand, when present on two different nucleic acid molecules, this allows the possibility to vary the molar ratio of the two nucleic acid constructs when introducing them into host cells, which may be an advantage if the preferred molar ratio is different from 1:1 or when it is unknown beforehand what is the preferred molar ratio, so that variation thereof and empirically finding the optimum can easily be performed by the skilled person. According to the invention, preferably at least one of the nucleic acid constructs, but more preferably each of them, comprises a at least one but preferably two nucleic acid fragments according to the invention.

In another embodiment, the different subunits or parts of a multimeric protein are present in a single expression construct. Useful configurations of anti-repressors combined with expression constructs have been described in WO 2006/048459 (e.g. page 40), incorporated by reference herein.

In a preferred embodiment, the gene product of interest is a coagulation factor such as Factor VIII or factor VII, interferons and interleukins, such as human interferon-gamma or therapeutic, anti-cancer monoclonal antibodies such as Herceptin (anti-EGF receptor) or Avastin (anti-vascular endothelial growth factor (VEGF)) or EPO.

A nucleic acid construct of the invention can be present in the form of double stranded DNA, having with respect to the selectable marker and the open reading frame encoding a gene product of interest a coding strand and a non-coding strand, the coding strand being the strand with the same sequence as the translated RNA, except for the presence of T instead of U. Hence, an AUG startcodon is coded for in the coding strand by an ATG sequence, and the strand containing this ATG sequence corresponding to the AUG startcodon in the RNA is referred to as the coding strand of the DNA. It will be clear to the skilled person that startcodons or translation initiation sequences are in fact present in an RNA molecule, but that these can be considered equally embodied in a DNA molecule coding for such an RNA molecule; hence, wherever the present invention refers to a startcodon or translation initiation sequence, the corresponding DNA molecule having the same sequence as the RNA sequence but for the presence of a T instead of a U in the coding strand of said DNA molecule is meant to be included, and vice versa, except where explicitly specified otherwise. In other words, a startcodon is for instance an AUG sequence in RNA, but the corresponding ATG sequence in the coding strand of the DNA is referred to as startcodon as well in the present invention. The same is used for the reference of 'in frame' coding sequences, meaning triplets (3 bases) in the RNA molecule that are translated into an amino acid, but also to be interpreted as the corresponding trinucleotide sequences in the coding strand of the DNA molecule.

A selectable marker to be applied in the expression cassettes comprised in the nucleic acid constructs of the invention preferably is functional in a eukaryotic host cell, more preferably, the marker is functional in a plant or animal host cell, still more preferably in a vertebrate host cell and most preferably in a mammalian host cell.

The term "selectable marker" is a term familiar to one of ordinary skill in the art and is used herein to describe any genetic entity which, when expressed, can be used to select for a cell or cells containing (and/or expressing) the selectable marker. Selectable markers may be dominant or recessive or bidirectional. The selectable marker may be a gene coding for a product which confers to a cell expressing the gene resistance to a selection agent such as e.g. an antibiotic or herbicide. The selectable marker may e.g. encode a selection protein that is able to neutralize or inactivate a toxic selection agent and protects the host cell from the agent's lethal or growth-inhibitory effects. Other selectable markers complement a growth-inhibitory deficiency in the cell under certain conditions. Examples of such genes include a gene which confers prototrophy to an auxotrophic strain. The term "reporter" is mainly used to refer to visible markers, such as green fluorescent protein (GFP), d2EGFP, luciferase, GUS and the like, as well as nptII markers and the like. Such reporters can be used for selecting cells expressing the visible marker by actively sorting cells expressing the marker from cells that do not, e.g. using a fluorescence activated cell sorter (FACS) for selecting cells that express a fluorescent marker protein. Preferably, the selectable marker according to the invention provides resistance against lethal and/or growth-inhibitory effects of a selection agent.

A nucleotide sequence encoding a selectable marker for use in the present invention encodes a protein that can be used for selection of eukaryotic host cells, e.g. because upon expression of the protein in the host cell it provides a growth advantage to the host cells expressing the selectable marker protein, as compared to host that do not. A preferred nucleotide sequence encoding a selectable marker provides resistance to a selection agent (e.g. an antibiotic) upon expression of the encoded selectable marker protein in the host cell, which selection agent causes lethality and/or growth inhibition of host cells not expressing the selectable marker protein. The selectable marker according to the invention must thus be functional in a eukaryotic host cell, and hence being capable of being selected for in eukaryotic host cells. Any selectable marker polypeptide fulfilling this criterion can in principle be used according to the present invention. Such selectable markers are well known in the art and routinely used when eukaryotic host cell clones are to be obtained, and several examples are provided herein.

For convenience and as generally accepted by the skilled person, in many publications as well as herein, often the gene encoding for the selectable marker and the selectable marker that causes resistance to a selection agent is referred to as the 'selectable agent (resistance) gene' or 'selection agent (resistance) protein', respectively, although the official names may be different, e.g. the gene coding for the protein conferring resistance to neomycin (as well as to G418 and kanamycin) is often referred to as neomycin (resistance) (or neo') gene, while the official name is aminoglycoside 3'-phosphotransferase gene.

In a preferred embodiment of the invention, the selectable marker provides resistance against lethal or growth-inhibitory effects of a selection agent selected from the group consisting of the bleomycin family of antibiotics, puromycin, blasticidin, hygromycin, an aminoglycoside antibiotic, methotrexate, and methionine sulphoximine.

A nucleotide sequence encoding a selectable marker providing resistance to bleomycin family of antibiotics is e.g. a nucleotide sequence encoding a wild-type "ble" gene, including but not limited to Sh ble, Tn5 ble and Sa ble or a variant thereof. An example thereof is depicted in SEQ ID NO: 8. In general the gene products encoded by the ble genes confer to their host resistance to the copper-chelating glycopeptide antibiotics of the bleomycin family, which are DNA-cleaving glycopeptides. Examples of antibiotics of the bleomycin family for use as selection agents in accordance with the present invention include but are not limited to bleomycin, phleomycin, tallysomycin, pepleomycin and Zeocin™. Zeocin is particularly advantageous as a selection agent, because the zeocin-resistance protein (zeocin-R) acts by binding the drug and thereby rendering it harmless. Therefore it is easy to titrate the amount of drug that kills cells with low levels of zeocin-R expression, while allowing the high-expressors to survive. Most if not all other antibiotic-resistance selectable markers in common use are enzymes, and thus act catalytically (i.e. not in a given, e.g. 1:1, stoichiometry with the selection agent). Hence, the antibiotic zeocin is a preferred selectable marker.

A nucleotide sequence encoding a selectable marker providing resistance to the aminoglycoside antibiotic is e.g. a nucleotide sequence encoding a wild-type aminoglycoside 3'-phosphotransferase or a variant thereof. An aminoglycoside according to the present invention are the commonly known aminoglycoside antibiotics (Mingeot-Leclercq, M. et al., 1999, Chemother. 43: 727-737) comprising at least one amino-pyranose or amino-furanose moiety linked via a glycosidic bond to the other half of the molecule. Their antibiotic effect is based on inhibition of protein synthesis. Examples of aminoglycoside antibiotics for use as selection agents in accordance with the present invention include but are not limited Kanamycin, Streptomycin, Gentamicin, Tobramycin, G418 (Geneticin), Neomycin B (Framycetin), Sisomicin, Amikacin, Isepamicin and the like.

Other examples of selectable markers which can be used in the invention are DHFR, cystathionine gamma-lyase and glutamine synthetase (GS) genes. A potential advantage of the use of these types of metabolic enzymes as selectable marker polypeptides is that they can be used to keep the host cells under continuous selection, which may advantageous under certain circumstances.

The DHFR gene, which can be selected for by methotrexate, especially by increasing the concentration of methotrexate cells can be selected for increased copy numbers of the DHFR gene. The DHFR gene may also be used to complement a DHFR-deficiency, e.g. in CHO cells that have a DHFR⁻ phenotype, in a culture medium with folate and lacking glycine, hypoxanthine and thymidine. If the selectable marker is DHFR, the host cell in advantageous embodiments is cultured in a culture medium that contains folate and which culture medium is essentially devoid of hypoxanthine and thymidine, and preferably also of glycine. In general, with "culture medium is essentially devoid" is meant herein that the culture medium has insufficient of the indicated component present to sustain growth of the cells in the culture medium, so that a good selection is possible when the genetic information for the indicated enzyme is expressed in the cells and the indicated precursor component is present in the culture medium. Preferably, the indicated component is absent from the culture medium. A culture medium lacking the indicated component can be prepared according to standard methods by the skilled person or can be obtained from commercial media suppliers.

Selection for a glutamine synthetase (GS) gene, e.g. a wild-type human or mouse glutamine synthetase gene, is possible in cells having insufficient GS (e.g. NS-O cells) by culturing in media without glutamine, or alternatively in cells having sufficient GS (e.g. CHO cells) by adding an inhibitor of GS, methionine sulphoximine (MSX).

Cystathionine gamma-lyase (EC 4.4.1.1) is an enzyme that is crucial for the synthesis of the amino acid L-cysteine. CHO cells are natural auxotrophs for the conversion of cysthathionine to cysteine. Therefore, the cystathionine gamma-lyase (cys-lyase) gene, e.g. from mouse or human, can be used for selection of cells by complementation by culturing cells in media without L-cysteine and L-cystine. Selection on the basis of the cys-lyase marker may require the non-toxic precursor L-cystathionine to be present in the culture medium. The use of cys-lyase as selectable marker in some vertebrate cell lines may first require inactivation (knock-out) of the endogenous cystathionine gamma-lyase genes. Alternatively, selection on the basis of the cys-lyase marker may further require an inhibitor of cystathionine gamma-lyase activity to be present in the culture medium. Suitable inhibitors of cystathionine gamma-lyase activity for this purpose include e.g. propargylglycine, trifluoroalanine, aminoethoxyvinylglycine and L-beta-oxalyl-amino-L-alanine.

Further selectable markers and their selection agents that could be used in the context of the present invention, are for instance described in Table 1 of U.S. Pat. No. 5,561,053, incorporated by reference herein; see also Kaufman, Methods in Enzymology, 185:537-566 (1990), for a review of these selectable markers and their selection agents.

In a preferred embodiment, the expression cassette in a nucleic acid construct of the present invention, comprises a selectable marker that is a stringent selection marker. A stringent selection marker is herein understood as a selection marker that requires to be transcribed (and/or expressed) at high level in the host cell expressing the marker for that host cell to be selected, i.e. for that host cell to survive the applied selection. In the context of the present invention, the stringency of the selectable marker is preferably increased by at least one of a) reducing the translation (initiation) efficiency of the selectable marker and b) reducing the activity and/or efficacy of the selectable marker polypeptide. Therefore, the expression cassette in a nucleic acid construct of the present invention, preferably comprises a nucleotide sequence encoding the selectable marker which nucleotide sequence is a least one of:

a) a nucleotide sequence having a mutation in the startcodon that decreases the translation initiation efficiency of the selectable marker polypeptide in a eukaryotic host cell;

b) a nucleotide sequence that is part of a multicistronic transcription unit comprising i) the nucleotide sequence encoding the selectable marker; and, ii) a functional open reading frame comprising in a 5' to 3' direction a translation initiation codon, at least one amino acid codon and a translation stop codon; wherein the stop codon of functional open reading frame is present between 0 and 250 nucleotides upstream of the separate translation initiation codon of the nucleotide sequence encoding the selectable marker, and wherein the sequence separating the stop codon of functional open reading frame and the separate translation initiation codon of the nucleotide sequence encoding the selectable marker is devoid of translation initiation codons; and, c) a nucleotide sequence encoding a selectable marker polypeptide comprising a mutation encoding at least one amino acid change that reduces the activity of the selectable marker polypeptide compared to its wild-type counterpart.

Nucleotide sequences encoding a selectable marker having a mutation in the (translation) startcodon (a sub-optimal non-AUG initiation codon) that decreases the translation initiation efficiency of the selectable marker polypeptide in a eukaryotic host cell are known in the art (see e.g. WO 2007/096399). A non-ATG (non-AUG) startcodon is herein understood as a translation initiation codon comprising a mutation in the startcodon that decreases the translation initiation efficiency of the selectable marker polypeptide in a eukaryotic host cell. Examples of non-ATG start codons that may be used for the coding sequence of the selectable marker in the invention include e.g. GTG, TTG, CTG, ATT, and ACG. In a preferred embodiment, the ATG startcodon is mutated into a GTG startcodon. More preferably, the ATG startcodon is mutated to a TTG startcodon, which provides even lower expression levels of the selectable marker polypeptide than with the GTG startcodon. When using a non-ATG startcodon, it is preferred that the non-ATG start codon is present in an optimal context for translation initiation codon, such as a Kozak consensus sequence as herein defined below. When applying a non-ATG startcodon for the selectable marker the nucleotide sequence coding for the selectable marker can be mutated to be devoid of internal ATG codons, particularly devoid of internal ATG codons that are in frame with the non-ATG start codon. This is preferred in constructs wherein the selectable marker is upstream of a nucleotide sequence coding for a gene product of interest without using an IRES in between the sequences coding for the gene product of interest and the marker. WO 2006/048459 discloses how to bring this about (e.g. by substitution, insertion or deletion, preferably by substitution) and how to test the resulting selectable marker polypeptides for functionality.

The second option for reducing the efficiency of translation initiation in b) above, uses a (short) functional open reading frame ($pp^x$; wherein $pp^x$ is a petit peptide of x amino acid residues) directly preceding the translation initiation codon of the selectable marker. The length of the functional open reading frame ($pp^x$) can be varied in order to fine tune low levels of translational efficiency of the selectable marker polypeptide, so that the exact required level of stringency of selection is obtained. Thus, the functional open reading frame may thus encode at least 1, 2, 3, 4, 5, 6, 7, 8, 9, 10, 11, 12, 13, 14, 15, 20, 25, 30, 35, 40, 45, 50, 55, 60, 70, 80 or 90 amino acid residues and preferably encodes no more than 200, 180, 160, 150, 140, 130, 120, 110, 100, 99, 98, 97, 96, 95, 94, 93, 92, 91, or 90 amino acid residues with a startcodon at the 5' and a stopcodon at the 3' end. By thus varying the length of the functional open reading frame ($pp^x$) that immediately precedes the sequence encoding the selectable marker in the transcript, a near continuous range of translational efficiencies of the selectable marker is provided. The functional open reading frame ($pp^x$) may be located immediately upstream of the separate startcodon of the selectable marker, in which case the stopcodon of the functional open reading frame is immediately adjacent to the start codon of the sequence coding for the selectable marker. Alternatively the stopcodon of the upstream functional open reading frame (pp$^x$) and the startcodon of the sequence coding for the selectable marker may be separated by 1, 2, 3, 4, 5, 6, 7, 8, 9, 10, 12, 14, 16, 18, 19, 20, 25, 30, 35, 40, 45, 50, 60, 70, 80, 90, 100, 120, 140, 160 180, 200, 250 or more nucleotides. Variation of the length of the spacer sequence separating the stopcodon of the upstream functional open reading frame (pp$^x$) and the startcodon of the sequence coding for the selectable marker adds a further level of fine tuning of the translational efficiency of the selectable marker. The spacer sequence separating the stop codon of functional open reading frame (pp$^x$) and the separate translation initiation codon of the nucleotide sequence encoding the selectable marker is devoid of translation initiation codons. Preferably therefore, the spacer sequence lacks ATG codons. More preferably, the spacer sequence also lacks suboptimal non-ATG codons such as GTG, TTG, CTG, ATT, and ACG (see below) embedded in a Kozak sequence (see below). Most preferably, the spacer sequence is devoid of any of the ATG, GTG, TTG, CTG, ATT, and ACG codons. In a further preferred embodiment, the spacer sequence separating the stop codon of functional open reading frame (pp$^x$) and the separate translation initiation codon of the nucleotide sequence encoding the selectable marker is devoid of stopcodons, i.e. lacks TAA, TAG and TGA codons.

In a preferred embodiment, at least one of the translation initiation codons of the nucleotide sequence encoding the selectable marker and of the functional open reading frame (pp$^x$) is an ATG codon. More preferably at least the initiation codon of the nucleotide sequence encoding the functional open reading (pp$^x$) is an ATG codon, in which case the initiation codon of the nucleotide sequence encoding the selectable marker can be a non-ATG startcodon (also known as suboptimal or less-favorable translation initiation codon), in order to allow for even more stringent selection (see above). Most preferably both the translation initiation codons of the nucleotide sequence encoding the selectable marker and the functional open reading frame (pp$^x$) are ATG codons. However, the invention does not exclude that the initiation codon of the nucleotide sequence encoding the functional open reading (pp$^x$) is a non-ATG startcodon.

In one embodiment, at least one of the initiation codons of the nucleotide sequence encoding the selectable marker and the functional open reading frame (pp$^x$) is embedded in a Kozak consensus sequence. The Kozak consensus sequence (for vertebrate host cells) is herein defined as ANN(AUG)N (SEQ ID NO: 4) and GNN(AUG)G (SEQ ID NO: 5), wherein (AUG) stands for the initiation codon of the relevant coding sequence. Preferably, both N's preceding the (AUG) are C's. A more preferred Kozak consensus sequence is GCCRCC(AUG)G (SEQ ID NO: 6), wherein R is a purine. In a further preferred embodiment, the Kozak consensus sequence may be preceded by yet another GCC triplet.

A preferred selectable markers preceded by a functional open reading frame (pp$^x$) is e.g. pp$^{90}$ZEO (a pp$^x$ open reading frame that encodes 90 amino acids preceding the zeomycin resistance protein; the pp$^{90}$ coding sequence is given in SEQ ID NO: 7).

In one embodiment, alternatively or in combination with a decreased translation initiation efficiency of a) or b) above, it can be beneficial to also provide for decreased translation elongation efficiency of the selectable marker polypeptide. This may be achieved by e.g. mutating the sequence coding the selectable marker polypeptide so as to decrease the adaptation of the codon usage to the host cell in question. This again provides a further level of controlling the stringency of selection of the nucleic acid constructs of the invention. Thus, a nucleotide sequence encoding a selectable marker protein, is preferably adapted to a codon usage to that is suboptimal in host cell in question. An codon adapted nucleotide sequence in accordance with the present invention preferably has a CAI of no more than 0.7, 0.6, 0.5, 0.4, 0.3 or 0.2 (see above for definition of CAI).

In one embodiment, alternatively or in combination with the embodiments of selectable markers with a decreased translation initiation efficiency as described in a) or b) above, mutants or derivatives of selectable markers are suitably used according to the invention, and are therefore included within the scope of the term 'selectable marker', as long as the selectable marker is still functional. Mutants or derivatives of a selectable marker preferably have reduced activity of the selectable marker compared to its wild-type counterpart allowing a further level of control in fine tuning of the stringency of selection of the nucleic acid constructs of the invention. Alternatively or in combination with one or more other embodiments, in a preferred embodiment, the nucleotide sequence encoding the selectable marker encodes a selectable marker polypeptide comprising one or more mutations that (collectively) reduce the activity of the selectable marker polypeptide compared to its wild-type counterpart. The activity of the mutated selectable marker polypeptide can be or more than 90, 80, 70, 60, 50, 40, 30, 20, 10, 5 or 1% to its wild-type counterpart.

As non-limiting examples, proline at position 9 in the zeocin resistance polypeptide may be mutated, e.g. to Thr or Phe (see e.g. example 14 of WO 2006/048459, incorporated by reference herein), and for the neomycin resistance polypeptide, amino acid residue 182 or 261 or both may further be mutated (see e.g. WO 01/32901). A preferred selectable marker polypeptide with reduced activity is a zeocin resistance polypeptide having the amino acids sequence encoded by SEQ ID NO: 8 wherein the glutamic acid at position 21 is changed into glycine, and the alanine at position 76 is changed into threonine (Zeo$^{EPP5}$).

A particularly preferred stringent selectable marker is pp$^8$ZEO$^{EPP5}$, which combines a pp$^x$ open reading frame of 8 amino acids and the Zeo$^{EPP5}$ zeocin resistance protein with reduced activity. The sequence of pp$^8$ZEO$^{EPP5}$ is depicted in SEQ ID NO: 9.

A nucleic acid construct according to the invention is preferably comprised in a plasmid or an expression construct can be a plasmid. A plasmid can easily be manipulated by methods well known to the person skilled in the art, and can for instance be designed for being capable of replication in prokaryotic and/or eukaryotic cells. Alternatively, a nucleic acid construct may be a vector. Many vectors can directly or in the form of isolated desired fragment therefrom be used for transformation of eukaryotic cells and will integrate in whole or in part into the genome of such cells, resulting in stable host cells comprising the desired nucleic acid in their genome.

Conventional expression systems are DNA molecules in the form of a recombinant plasmid or a recombinant viral genome. The plasmid or the viral genome is introduced into (eukaryotic host) cells and preferably integrated into their genomes by methods known in the art, and several aspects hereof have been described in WO 2006/048459 (e.g. pages 30-31), incorporated by reference herein.

It is widely appreciated that chromatin structure and other epigenetic control mechanisms may influence the expression of transgenes in eukaryotic cells (e.g. Whitelaw et al, 2001, Methods Mol Biol 158: 351-68). To increase the chance of finding clones of host cells that survive rigorous selection regimes, and possibly to increase the stability of expression in obtained clones, it will generally be preferable to increase the predictability of transcription. The nucleic acid constructs and vectors according to the invention therefore preferably comprise at least one or more further "expression enhancing nucleic acid fragments" linked to the expression cassette, in addition to the nucleic acid fragments of the invention as defined above (i.e. comprising sequences from or with similarity to the RPL32 promoter region). Such further "expression enhancing nucleic acid fragments" may include "chromatin control elements", "anti-repressor sequences" and "gene expression enhancing elements" as herein described below.

A "chromatin control element" as used herein is a collective term for DNA sequences that may somehow have an effect on the chromatin structure and therewith on the expression level and/or stability of expression of transgenes in their vicinity (they function "in cis", and hence are placed preferably within 5 kb, more preferably within 2 kb, still more preferably within 1 kb from the transgene) within eukaryotic cells. Such elements have sometimes been used to increase the number of clones having desired levels of transgene expression. Several types of such elements that can be used in accordance with the present invention have been described in WO 2006/048459 (e.g. page 32-34), incorporated by reference herein, and for the purpose of the present invention chromatin control elements are chosen from the group consisting of matrix or scaffold attachment regions (MARs/SARs), insulators such as the beta-globin insulator element (5' HS4 of the chicken beta-globin locus), scs, scs', and the like, a ubiquitous chromatin opening element (UCOE), and anti-repressor sequences (also referred to as "STAR" sequences).

Preferably, said chromatin control element is an anti-repressor sequence, preferably chosen from the group consisting SEQ. ID. NO. 1 to SEQ. ID. NO. 66 as disclosed in WO 2007/096399. More preferably, said chromatin control element is chosen from the group consisting of STAR67, STAR7, STAR9, STAR17, STAR27, STAR29, STAR43, STAR44, STAR45, STAR47, STAR61, as disclosed in WO 2007/096399 or a functional fragment or derivative of said STAR sequences. In a most preferred embodiment, a combination of STAR7 and STAR 67 is used, or functional fragments or derivatives of STAR7 and STAR67. In certain preferred embodiments, at least one of STAR7 and STAR 67 or a functional fragment or derivative thereof is positioned upstream of a promoter driving expression of the multicistronic transcription unit. In other preferred embodiments, the expression cassettes according to the invention are flanked on both sides by at least one the anti-repressor sequence as described above. In certain embodiments, expression cassettes are provided according to the invention, comprising in 5' to 3' order: anti-repressor sequence A—anti-repressor sequence B—[promoter—multicistronic transcription unit according to the invention (encoding the gene product of interest and downstream thereof the functional selectable marker protein)—transcription termination sequence]—anti-repressor sequence C, wherein A, B and C may be the same or different. In a preferred embodiment A and C are STAR7 and B is STAR67. Sequences having anti-repressor activity (anti-repressor sequences) and characteristics thereof, as well as functional fragments or derivatives thereof, and structural and functional definitions thereof, and methods for obtaining and using them, which sequences are useful for the present invention, have been described in WO 2006/048459 (e.g. page 34-38), incorporated by reference herein.

Another preferred gene expression enhancing element (that may be used instead of, or in addition to, the above-mentioned chromatin control elements or anti-repressor sequences) for use in the present invention is a nucleic acid fragment which functions as a source for intergenic transcription. Preferably the nucleic acid fragment which functions as a source for intergenic transcription comprising at least 1,000, 1,500, 2,000, 3,500 or 7,000 consecutive nucleotides of a genomic region that is present upstream of the translation initiation site of a vertebrate Rb1 or P15 gene and functions as a source for intergenic transcription. Preferably the nucleic acid fragment comprises at least 1,000, 1,500, 2,000, 3,500 or 7,000 consecutive nucleotides of SEQ ID NO: 11 (human Rb1F and E) consisting of a nucleotide sequences present about 7 kb upstream of the translation initiation site of the human Rb1 gene. More preferably the nucleic acid fragment comprises at least 1,000, 1,500, 2,000, 2,500, 3,000 or 3,498 consecutive nucleotides of SEQ ID NO: 12 (human Rb1E) (see also Examples herein). Alternatively preferred, the nucleic acid fragment comprises at least 1,000, 1,500, 2,000, 2,500, 3,000 or 3,352 consecutive nucleotides of SEQ ID NO: 13 (human P15C). In certain embodiments, expression cassettes are provided according to the invention, comprising in 5' to 3' order: a nucleic acid fragment which functions as a source for intergenic transcription A—[promoter—multicistronic transcription unit according to the invention (encoding the gene product of interest and a CLase selectable marker)—transcription termination sequence]—a nucleic acid fragment which functions as a source for intergenic transcription B, wherein A and B may be the same or different. In a preferred embodiment A and B are SEQ ID NO: 12, or A and B are SEQ ID NO: 13, or A and B are a sub fragment of one of SEQ ID NO's: 12 and 13 as indicated above.

In one embodiment, a nucleic acid construct according to the invention comprises an additional selection marker, e.g. a DHFR metabolic selection marker as described supra. An advantage of such a nucleic acid construct is that selection of a host cell with high expression can be established by use of a selection marker operably linked with an IRES, e.g. zeocin, neomycin, etc, whereas after the selection of a host cell with high expression the antibiotic selection is discontinued and either continuous or intermittent selection is done using the additional selection marker. The multicistronic transcription units in this embodiment are at least tricistronic.

It is preferred to use separate nucleic acid constructs for the expression of different gene products of interest, also when these form part of a multimeric protein (see e.g. example 13 of WO 2006/048459, incorporated by reference herein): the heavy and light chain of an antibody each are encoded by a separate transcription unit according to the invention. When two transcription units of the invention are to be selected for according to the invention in a single host cell, each one preferably contains the coding sequence for a different selectable marker, to allow selection for both transcription units. Of course, both transcription units may be present on a single nucleic acid molecule or alternatively each one may be present on a separate nucleic acid molecule.

In a third aspect, the present invention relates to an expression vector or an expression construct comprising a nucleic acid construct according to the invention.

In a fourth aspect, the present invention relates to a host cell, preferably a eukaryotic host cell, comprising a nucleic acid construct according to the invention or an expression vector according to the invention.

The terms "cell" or "host cell" and "cell line" or "host cell line" are respectively defined as a cell and homogeneous populations thereof that can be maintained in cell culture by methods known in the art, and that have the ability to express heterologous or homologous proteins. The host is an eukaryotic host cell such as a cell of fungal, plant, or animal origin. Preferably the host cell is an animal cell of insect or vertebrate origin. More preferably the host cell is a mammalian cell. Preferably, the host cell is a cell of a cell line. Several exemplary host cells that can be used have been described in WO 2006/048459 (e.g. page 41-42), incorporated by reference herein, and such cells include for instance mammalian cells, including but not limited to CHO cells, e.g. CHO-K1, CHO-S, CHO-DG44, CHO-DG44-S, CHO-DP12, CHO-DUKXB1 1, including CHO cells having a dhfr⁻ phenotype, as well as myeloma cells (e.g. Sp2/0, NS0), HEK 293 cells, HEK 294 cells, and PER.C6 cells. Other examples of host cells that can be used are a U-2 OS osteosarcoma, HuNS-1 myeloma, WERI-Rb-1 retinoblastoma, BHK, Vero, non-secreting mouse myeloma Sp2/0-Ag 14, non-secreting mouse myeloma NS0 and NCI-H295R adrenal gland carcinoma cell line.

Such eukaryotic host cells can express desired gene products, and are often used for that purpose. They can be obtained by introduction of a nucleic acid construct of the invention, preferably in the form of an expression construct, an expression cassette or an expression vector according to the invention, into the cells. Preferably, the nucleic acid construct is integrated in the genome of the host cell, which can be in different positions in various host cells, and selection will provide for a clone where the transgene is integrated in a suitable position, leading to a host cell clone with desired properties in terms of expression levels, stability, growth characteristics, and the like.

Alternatively a nucleic acid construct without promoter may be targeted or randomly selected for integration into a chromosomal region that is transcriptionally active, e.g. behind a promoter present in the genome. Selection for cells containing the DNA of the invention can be performed by selecting for the selectable marker polypeptide, using routine methods known by the person skilled in the art. When such a nucleic acid construct without promoter is integrated behind a promoter in the genome, a nucleic acid construct according to the invention can be generated in situ, i.e. within the genome of the host cells.

Preferably the host cells are from a stable clone that can be selected and propagated according to standard procedures known to the person skilled in the art. A culture of such a clone is capable of producing gene product of interest, if the cells comprise the multicistronic transcription unit of the invention.

Introduction of nucleic acid that is to be expressed in a cell, can be done by one of several methods, which as such are known to the person skilled in the art, also dependent on the format of the nucleic acid to be introduced. Said methods include but are not limited to transfection, infection, injection, transformation, and the like. Suitable host cells that express the gene product of interest can be obtained by selection.

In preferred embodiments, a nucleic acid construct according to the invention is integrated into the genome of the eukaryotic host cell according to the invention. This will provide for stable inheritance of the nucleic acid construct.

In a fifth aspect, the present invention relates to a method of generating a host cell for expression of a gene product of interest, wherein the method comprises the steps of: a) introducing into a plurality of host cells a nucleic acid construct according to the invention or a expression vector according to the invention; b) culturing the plurality of host cells obtained in a) under conditions selecting for expression of the selectable marker polypeptide; and, c) selecting at least one host cell expressing the selectable marker polypeptide for expression of the gene product of interest.

Advantages of this method are similar to those described for the method disclosed in WO 2006/048459 (e.g. page 46-47), incorporated by reference herein. While clones having relatively low copy numbers of the nucleic acid construct and high expression levels can be obtained, the selection system of the invention nevertheless can be combined with amplification methods to even further improve expression levels. This can for instance be accomplished by amplification of a co-integrated DHFR gene using methotrexate, for instance by placing DHFR on the same nucleic acid molecule as the multicistronic transcription unit of the invention, or by cotransfection when DHFR is on a separate DNA molecule. The DHFR gene can also be part of a nucleic acid construct of the invention or of the expression vector of the invention.

Selection for the presence of the selectable marker polypeptide, and hence for expression, can be performed during the initial obtaining of the host cell. In certain embodiments, the selection agent is present in the culture medium at least part of the time during the culturing, either in sufficient concentrations to select for cells expressing the selectable marker or in lower concentrations.

In a sixth aspect, the present invention relates to a method of expressing a gene product of interest, comprising culturing a host cell comprising a nucleic acid construct according to the invention or a vector according to the invention, a host cell according to the invention or a host cell obtained in a method according to the invention, and expressing the gene product of interest from the nucleic acid construct. In preferred embodiments, selection agent is no longer present in the culture medium during final the production phase of gene product of interest so as to avoid any risk of contamination of the gene product with trace of the possibly noxious selection agent.

In certain embodiments, an expression vector of the invention encodes an immunoglobulin heavy or light chain or an antigen binding part, derivative and/or analogue thereof. In a preferred embodiment a protein expression unit according to the invention is provided, wherein said protein of interest is an immunoglobulin heavy chain. In yet another preferred embodiment a protein expression unit according to the invention is provided, wherein said gene product of interest is an immunoglobulin light chain. When these two protein expression units are present within the same (host) cell a multimeric protein and more specifically an immunoglobulin, is assembled. Hence, in certain embodiments, the protein of interest is an immunoglobulin, such as an antibody, which is a multimeric protein. Preferably, such an antibody is a human or humanized antibody. In certain embodiments thereof, it is an IgG, IgA, or IgM antibody. An immunoglobulin may be encoded by the heavy and light chains on different expression vectors, or on a single expression vector. Thus, the heavy and light chain can each be present on a separate expression vector, each having its own promoter (which may be the same or different for the two expression vectors), each comprising a transcription unit according to the invention, the heavy and light chain being the gene product of interest, and preferably each coding for a different selectable marker protein, so that selection for both heavy and light chain expression vector can be performed when the expression vectors are introduced and/or present in a eukaryotic host cell. Alternatively, the heavy and light chain coding sequences can be present on a single expression vector comprising a multicistronic transcription unit according to the invention, driven from a single promoter, and wherein the light and heavy chains are the gene products of interest with an IRES in between their respective coding sequences.

Culturing a cell is done to enable it to metabolize, and/or grow and/or divide and/or produce gene products of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant gene products through cell culture it is preferred in the art to have cells capable of growing in suspension, and it is preferred to have cells capable of being cultured in the absence of animal- or human-derived serum or animal- or human-derived serum components.

The conditions for growing or multiplying cells (see e.g. Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, a method of expressing a gene product of interest according to the invention further comprises harvesting the gene product of interest. The expressed gene product, e.g. protein may be harvested, collected or isolated either from the cells or from the culture medium or from both. It may then be further purified using known methods, e.g. filtration, column chromatography, etc, by methods generally known to the person skilled in the art.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, $2^{nd}$ edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988. [0088] The invention is further explained in the following examples. The examples do not limit the invention in any way. They merely serve to clarify the invention.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 1: Influence on colony formation of promoters that are used in combination with the human β-actin promoter in the context of a stringent selection system.

FIG. 2: Influence on protein expression of promoters that are used in combination with the human β-actin promoter in the context of a stringent selection system.

EXAMPLES

1. Example 1

Figure 3:
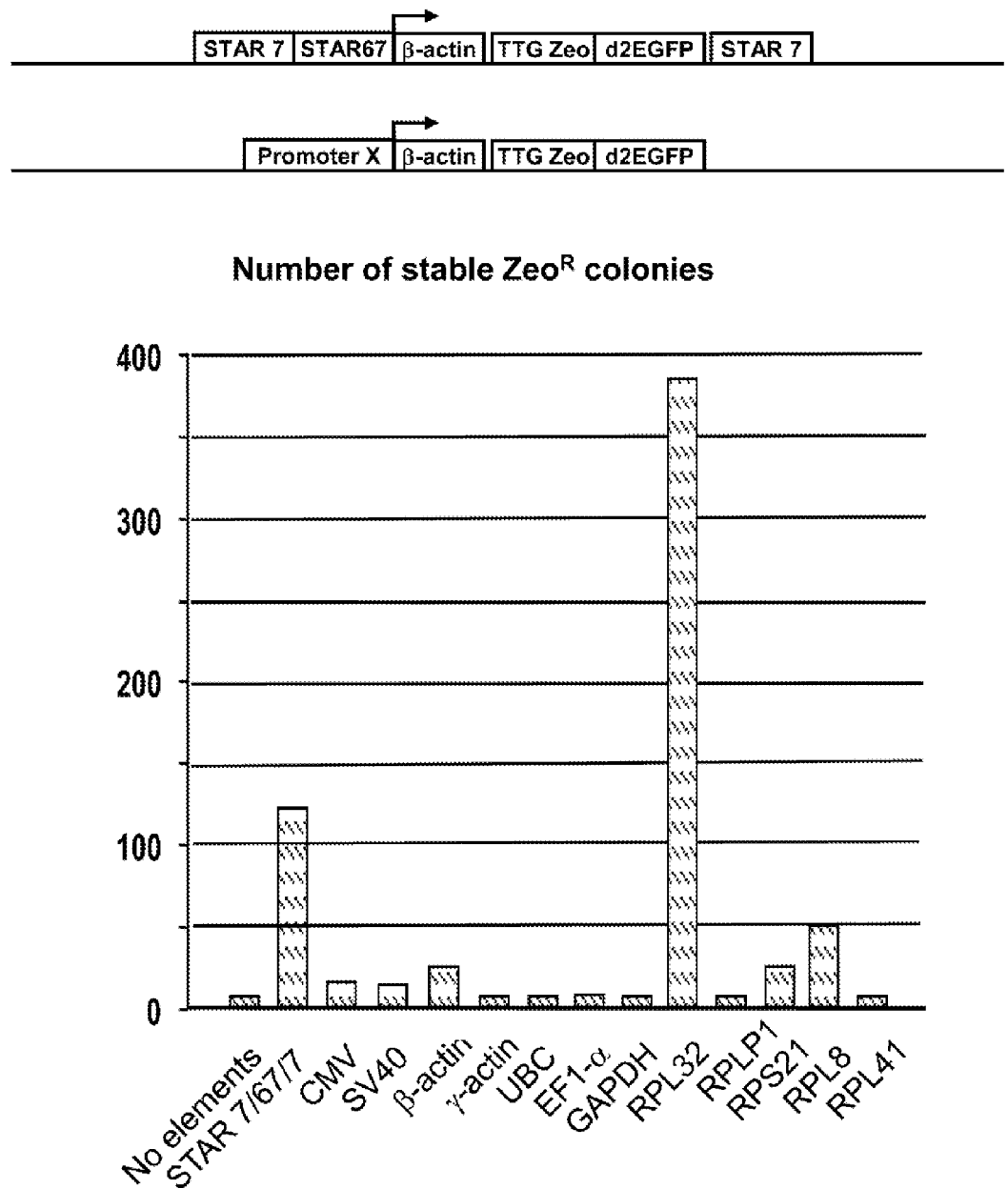
FIG. 3: Influence on colony formation of promoters that are used in combination with the human β-actin promoter and another stringent selection system.

Testing the Influence on Colony Formation and Protein Expression of Heterologous Promoters that are Placed Upstream of the Human β-Actin Promoter in the Context of a Stringent Selection System When CHO-DG44 are transfected with a plasmid that harbors a stringent selection marker, little or no colonies will emerge. Such a stringent selection marker can be the Zeocin resistance marker that has been mutated and that is preceded by a small peptide and that is placed downstream of the gene of interest, behind an IRES (internal ribosomal entry site) (see FIG. 1). However, when STAR elements are placed to flank the entire expression cassette, many more colonies will emerge, typically in the range of 50-100 per transfection (FIG. 1), when 400 µg/ml Zeocin is added to the CHO-DG44 culture medium. In general, the resulting clones convey high protein expression levels. Here, we tested whether placing a heterologous promoter upstream of the human β-actin promoter induces at least as many CHO-DG44 colonies as with STAR elements under the same selection conditions. We therefore used the same Zeocin resistance marker as is used with STAR elements, pp8Zeo$^{EPP5}$. The expression cassette was placed under control of the human β-actin promoter (FIG. 1). The sequence of the entire expression cassette is given in SEQ ID NO: 2. The sequence of the reference-construct wherein the expression cassette of SEQ ID NO: 2 is flanked by STAR elements (FIG. 1) is given in SEQ ID NO: 3.

1.1 Results

Twelve promoters were chosen for testing: the viral CMV and SV40 promoters, the human β-actin promoter itself, the human γ-actin promoter, the promoters of the human UBC, EF1-α, GAPDH genes and promoters of the human ribosomal genes RPL32, RPLP1, RPS21, RPL8 and RPL42. The promoters were isolated by PCR (see sequence listing for the primers: SEQ ID NO's: 14-47; F: forward, R: reverse) with human genomic DNA as template. The identity of the promoters was verified by DNA sequencing. The promoters were cloned immediately upstream of the human β-actin promoter. As control, a construct with the STAR 6/67/7 combination was chosen. Another control was a construct with the human β-actin promoter driving the d2EGFP IRES pp8Zeo$^{EPP5}$ expression unit, but without any other elements or heterologous promoter (FIG. 1).

We transfected the plasmids to CHO-DG44 cells. The same amount of DNA (3 μg) of all constructs was transfected to CHO-DG44 cells with Lipofectamine 2000 (Invitrogen). Selection was performed with 400 μg/ml Zeocin in the culture medium, which was added 24 hours after transfection. The culture medium consisted of HAMF12:DMEM=1:1+4.6% fetal bovine serum. After approximately two weeks the number of stably established colonies were counted. As shown in FIG. 1, transfection of the construct encompassing STAR7/67/7 resulted in 112 stable colonies. The construct with no elements or promoter (negative control) gave no colonies. The same result was obtained with ten heterologous promoters, except for the construct with the RPL8 upstream of the human β-actin promoter (55 colonies), but in particular with the RPL32 promoter (>250 colonies) (FIG. 1).

Up to 24 independent colonies induced by the indicated constructs were isolated. Colonies were propagated before analysis by flow cytometric analysis (EPICS-XLM, Beckman-Coulter), ~6 weeks after transfection. The fluorescence signal derived from d2EGFP (destabilized) is linear with the amount of available d2EGFP protein in a cell, and is thus a reliable indicator of the d2EGFP expression levels in the cell. In a single FACS analysis, fluorescence signals from a sample that contain up to 4000 cells are analyzed. One such sample of cells is taken from an independent, stably transfected cell colony. Since the signal will vary amongst the individual cells in the colony, the mean fluorescence level of the ~4000 cells in the sample is taken as a measure for the d2EGFP expression level in the stably transfected cell colony.

As shown in FIG. 2, placing heterologous promoters upstream of the human β-actin promoter resulted in varying d2EGFP expression values. At the lower end of the spectrum the CMV, EF1-α and RPL21 promoters, placed upstream of the human β-actin promoter induced very low d2EGFP values (FIG. 2), as well a hardly any colonies (FIG. 1). Importantly though, the d2EGFP expression levels in the construct with the RPL32-β-actin promoter combination were equally high as in the STAR7/67/7 induced d2EGFP values (FIG. 2). Only the RPL8 promoter gave also some colonies (FIG. 1), combined with intermediate d2EGFP values (FIG. 2).

We conclude that placing the RPL32 upstream of the human β-actin promoter, in combination with the d2EGFP IRES pp8Zeo$^{EPP5}$ expression unit induces many more colonies than the STAR7/67/7 combination in CHO-DG44 cells. Furthermore, the d2EGFP expression values in these clones equal the expression levels in the STAR 7/67/7 induced clones.

2. Example 2

Testing the Influence on Colony Formation and Protein Expression of Heterologous Promoters that are Placed Upstream of the Human β-Actin Promoter, in the Context of Another Stringent Selection System Another very stringent Zeocin selection marker is created by modifying its translation initiation codon. This is specifically the case with a Zeocin resistance marker that has a TTG translation initiation codon and that is placed under the control of the human β-actin promoter (See FIG. 3). Hardly any colonies will emerge in the context of this stringent selection marker. However, as in the case of the d2EGFP IRES pp8Zeo$^{EPP5}$ Zeocin marker, when STAR elements are placed to flank the TTG Zeo d2EGFP expression cassette, many more colonies will emerge, typically in the range of 50-100 per transfection (FIG. 3), when 400 μg/ml Zeocin is added to the CHO-DG44 culture medium. Also with the TTG Zeo, STAR-flanked plasmid, the resulting clones convey high protein expression levels. Here, we tested whether placing a heterologous promoter upstream of the human β-actin promoter induces at least as many CHO-DG44 colonies as with STAR elements under the same selection conditions. We therefore used the same Zeocin resistance marker as is used with STAR elements, TTG Zeo. The expression cassette was placed under control of the human β-actin promoter (FIG. 3).

2.1 Results

The same twelve promoters as in example 1 were chosen for testing: the viral CMV and SV40 promoters, the human β-actin promoter itself, the human γ-actin promoter, the promoters of the human UBC, EF1-α, GAPDH genes and promoters of the human ribosomal genes RPL32, RPLP1, RPS21, RPL8 and RPL42. The promoters were cloned immediately upstream of the human β-actin promoter. As control, a construct with the STAR 6/67/7 combination was chosen. Another control was a construct with the human β-actin promoter driving the TTG Zeo d2EGFP expression unit, but without any other elements or heterologous promoter (FIG. 3).

We transfected the plasmids to CHO-DG44 cells, as described in example 1. As shown in FIG. 3, transfection of the construct encompassing START/67/7 resulted in 135 stable colonies. The construct with no elements or promoter (negative control) gave <10 colonies. The same result was obtained with ten heterologous promoters, except for the construct with the RPL8 upstream of the human β-actin promoter (50 colonies), but in particular with the RPL32 promoter (>350 colonies) (FIG. 3). Overall, the number of stable colonies induced in the context of the TTG Zeo marker was slightly higher than in the context of the IRES pp8Zeo$^{EPP5}$ configuration (compare FIGS. 1 and 3).

Figure 4:
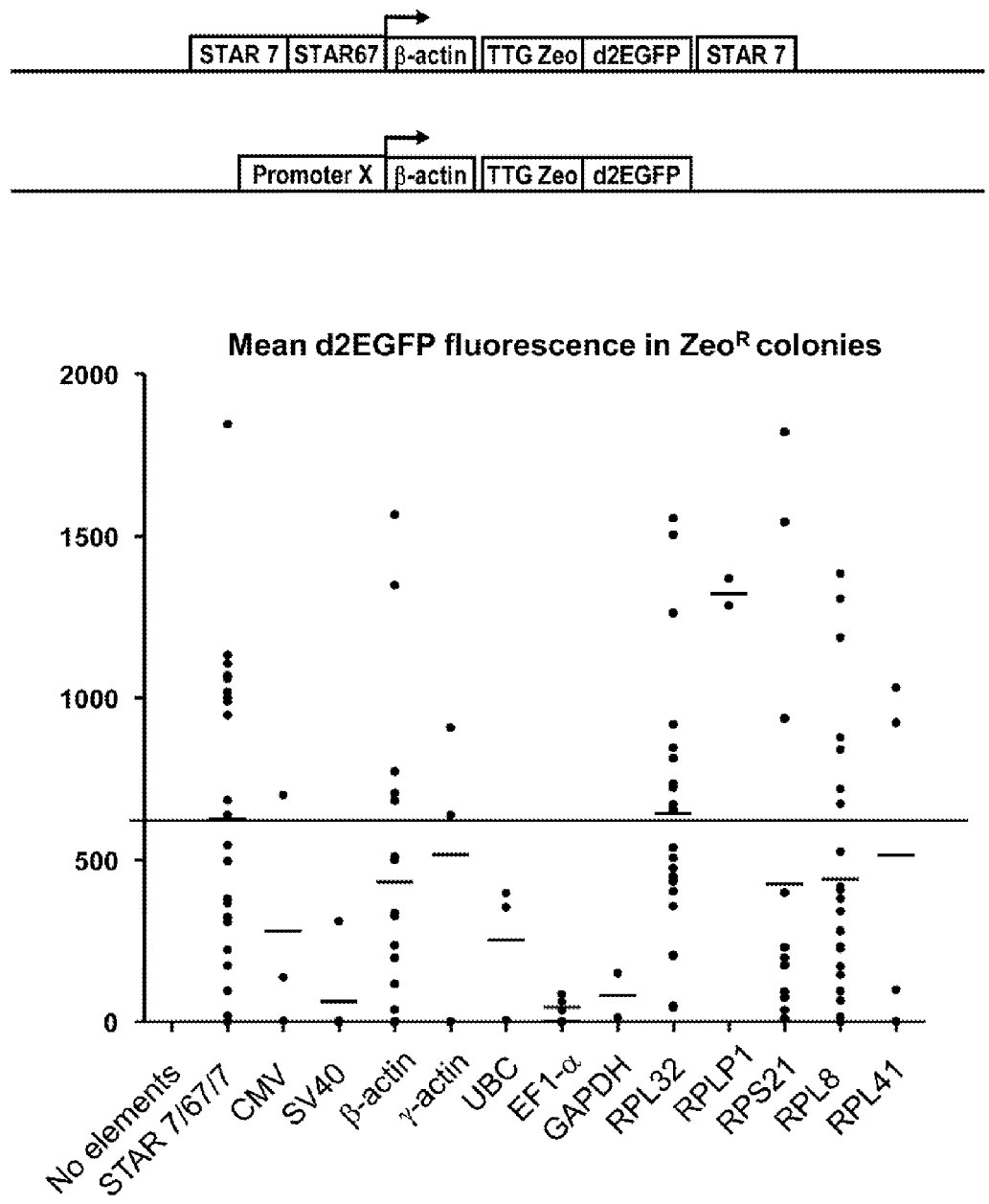
FIG. 4: Influence on protein expression of promoters that are used in combination with the human β-actin promoter and another stringent selection system.

Up to 24 independent colonies induced by the indicated constructs were isolated and d2EGFP values were determines, as described in example 1. As shown in FIG. 4, placing heterologous promoters upstream of the human β-actin promoter resulted in varying d2EGFP expression values. At the lower end of the spectrum the EF1-α promoter, placed upstream of the human β-actin promoter induced very low d2EGFP values (FIG. 4), as well a low number of colonies (FIG. 3). In contrast, the human γ-actin promoter, placed upstream of the human β-actin promoter induced a small number of colonies (FIG. 3), but the d2EGFP expression levels were high in these colonies (FIG. 4). Importantly though, the d2EGFP expression levels in the construct with the RPL32-human β-actin promoter combination were equally high as in the STAR7/67/7 induced d2EGFP values (FIG. 4).

Figure 5:
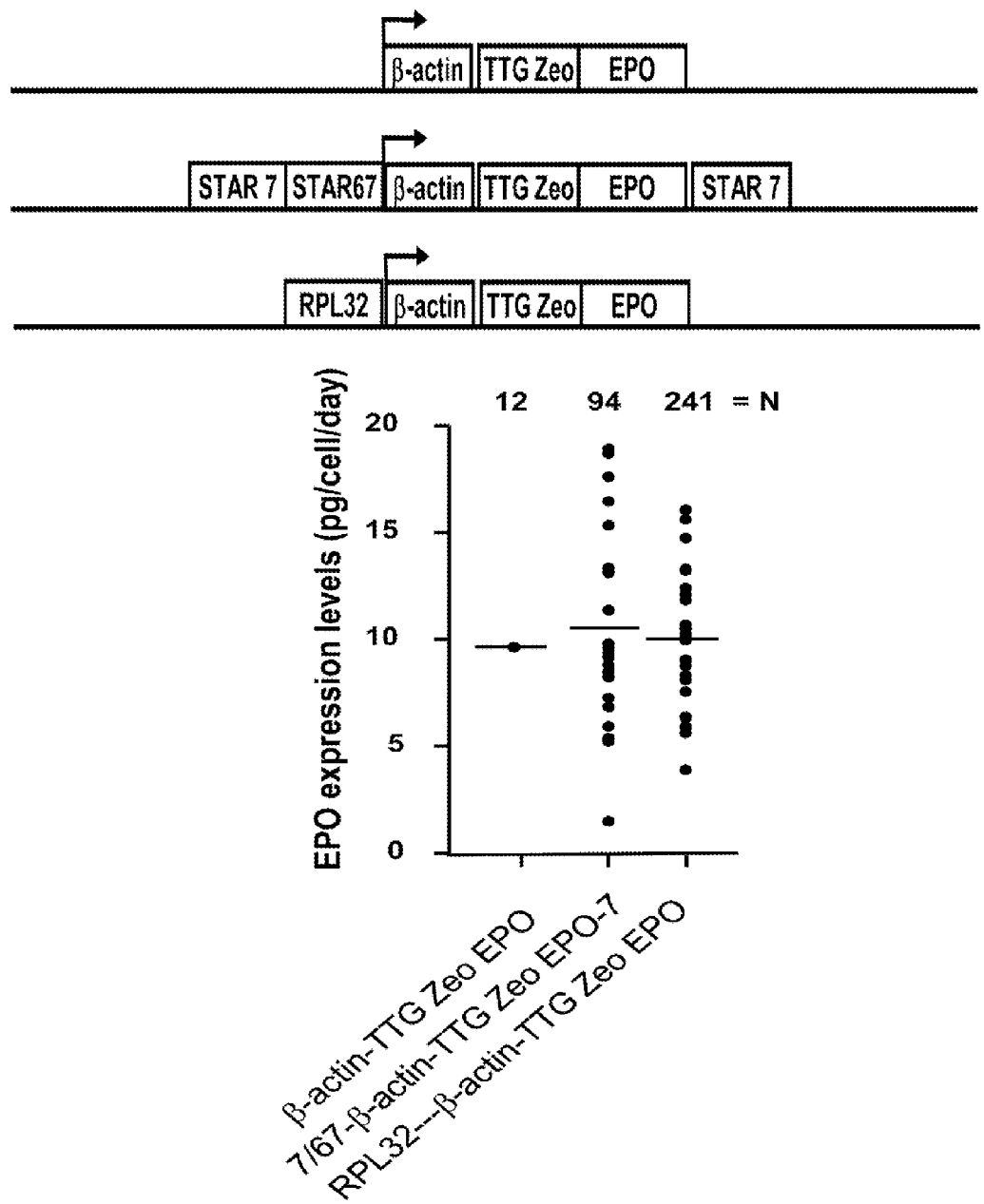
FIG. 5: Influence of the RPL32 promoter on EPO protein expression

We also tested another reporter protein in this last experimental set/up, using the TTG Zeo as selection marker. As shown in FIG. 5, RPL32 placed upstream of the human β-actin promoter induced many more colonies than with STAR 7/67/7 combination. In these colonies, EPO expression values were very similar with the STAR elements and the RPL32 promoter (FIG. 5).

We conclude that placing the RPL32 upstream of the human β-actin promoter, in combination with the TTG Zeo selection marker induces many more colonies than the STAR7/67/7 combination in CHO-DG44 cells. Furthermore, the d2EGFP expression values as well as EPO protein expression levels in these clones equal the expression levels in the STAR 7/67/7 induced clones. In combination with example 1, these results show that the RPL32 promoter exerts its positive effects in the context of two different stringent selection systems and with multiple reporter genes.

3. Example 3

Figure 6:
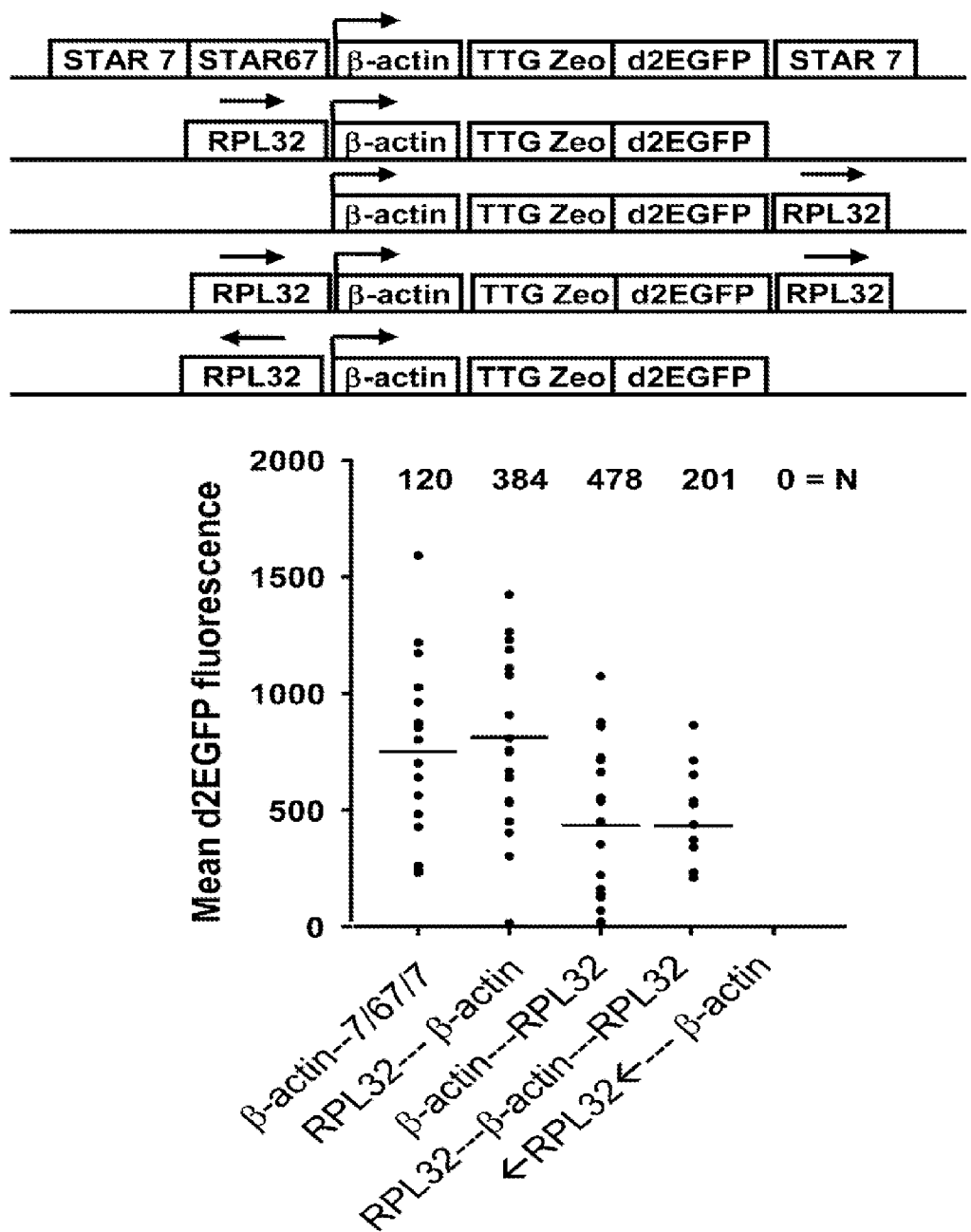
FIG. 6: Influence on different RPL32 promoter configurations on colony formation and protein expression.

Influence of the Configurations of Placing the RPL32 in an Expression Construct and the Influence of the RPL32 Promoter on Other Promoters We tested whether the location of the RPL32 promoter in the construct has influence on the number of induced colonies and the d2EGFP expression values. We also tested whether the RPL32 had a beneficial effect on promoters other than the human β-actin promoter.
3.1 Results We created constructs in which the RPL32 was placed upstream of the human β-actin promoter, downstream of the entire expression cassette or between the human β-actin promoter and the reporter gene (FIG. 6). Furthermore, we placed the RPL32 both up and downstream of the expression cassette. The plasmids were transfected to CHO-DG44 cells, colonies were counted as described above and the d2EGFP expression values in these colonies was determined. As shown in FIG. 6, in this experiment, most colonies were established when the RPL32 promoter was placed downstream of the entire expression cassette. The construct, in which the single RPL32 promoter was placed upstream of the human β-actin promoter, induced slightly less colonies, but almost two times more than when two RPL32 promoters were used to flank the entire expression cassette (FIG. 6). No colonies were formed when the RPL32 promoter was placed upstream of the β-actin promoter, but in such a configuration that the direction of transcription of the RPL32 promoter pointed away from the β-actin promoter (FIG. 6). This indicates that transcription originating from the RPL32 promoter must proceed through the β-actin promoter. When the d2EGFP values were determined in the respective clones, we observed that the 'single' RPL32-β-actin promoter configuration induced the highest average d2EGFP expression levels (FIG. 6). The d2EGFP values induced by plasmids in which either two RPL32 promoters were used or in which a single RPL32 promoter was placed downstream of the β-actin promoter were substantially lower (FIG. 6).

Figure 7:
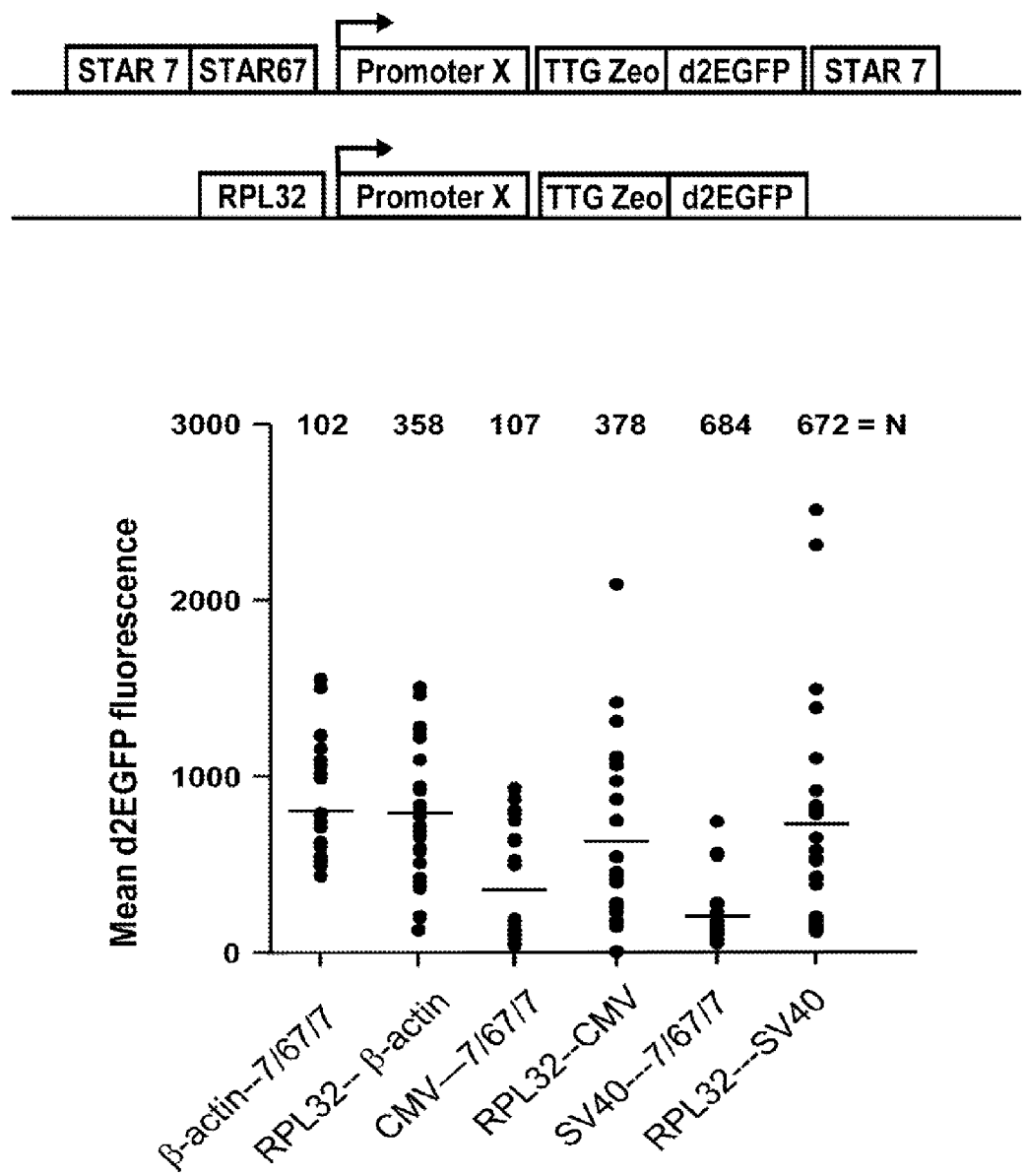
FIG. 7: Influence on colony formation of the RPL32 promoter combined with different promoters.

We next tested whether placing the RPL32 upstream of promoters other than the human β-actin promoter might also result in the formation of large numbers of colonies and d2EGFP expression values. We placed the RPL32 promoter upstream of the CMV and SV40 promoters (FIG. 7). As controls we flanked the CMV and SV40 driven constructs with the STAR 7/67/7 combination. As shown in FIG. 7, we found that the RPL32 promoter placed upstream of the CMV promoter induced >3 times more colonies than the STAR 7/67/7 combination. With the SV40 promoter, the RPL32 induced an equal number of colonies as the STAR 7/67/7 combination (FIG. 7). When the d2EGFP expression levels were determined in these respective clones we found that the RPL32-β-actin promoter combination induced equal d2EGFP expression levels as the STAR 7/67/7 combination (FIG. 7), as also observed above in examples 1 and 2. However, with the CMV and SV40 promoters, the RPL32 promoter induced substantially higher d2EGFP expression levels than the STAR 7/67/7 combination (FIG. 7).

We therefore conclude that the RPL32 promoter, placed upstream of different promoters has a beneficial effect on these promoters, both in terms of induced colony numbers and protein expression levels.

4. Example 4

The Orientation of the RPL32 Promoter and Functional Elements are Essential for its Influence on the Human β-Actin Promoter We tested what requirements determine the positive action of the RPL32 on the human β-actin promoter.
4.1 Results The RPL32 promoter lacks a canonical TATA box. The beta binding site of the RPL32 promoter contains the DNA sequence element (CGGAAC) and binds the Ets-related protein GA-binding protein (GABP) Thompson et al., 1991, Science 253:762-8; Macleod et al., 1992, Trends Biochem Sci 17:251-6; Yoganathan et al., 1992a, Biochem J 287: 349-53; Genuario et al., 1993, Gene Expr 3: 279-88). In spite of the lack of a canonical TATA element in the RPL32 gene promoter, TATA-binding protein (TBP) interacts with a region 30 base pairs upstream of the cap site without the aid of other factors (Yoganathan et al., 1992b, Biochem J 285: 721-3). This region contains the binding site for the gamma factor and indicates that the gamma factor may play a role similar to TBP in transcription of the RPL32 gene.

Figure 8A:
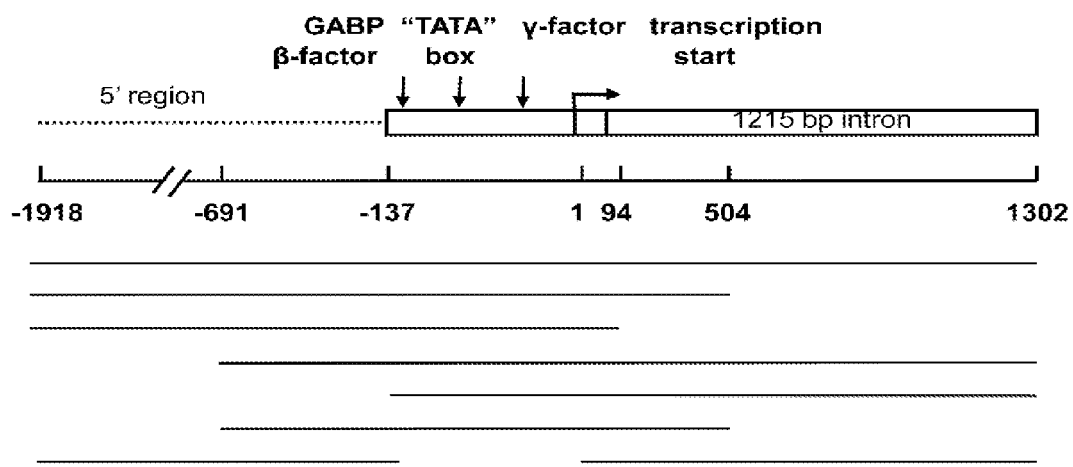
FIG. 8: Features of the RPL32 promoter that influence colony formation and protein expression.
Figure 8B:
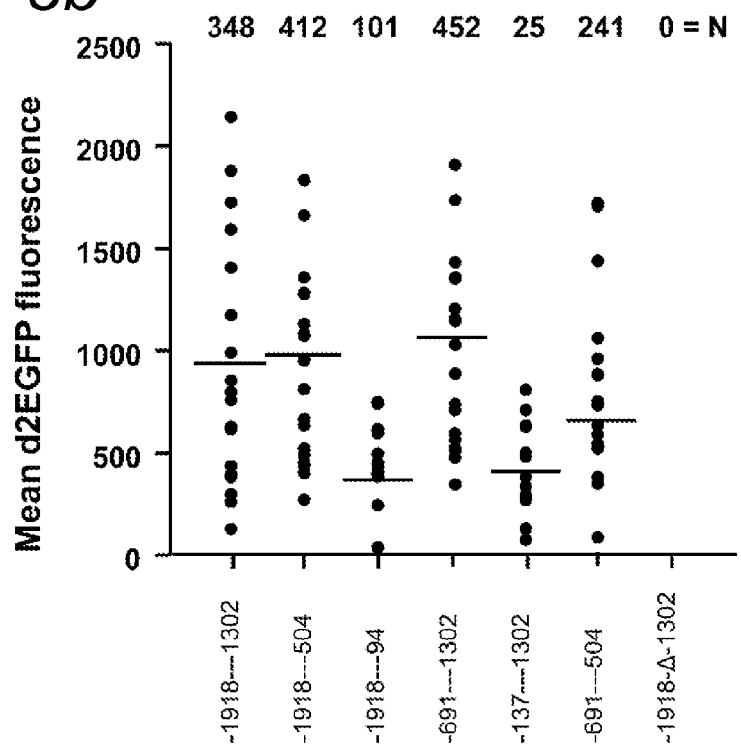

As indicated in FIG. 8A, we deleted several portions, 5' and 3' of the originally isolated 3220 bp RPL32 promoter region. In addition, we deleted the 100 bp immediately upstream of the transcription start site that contains all above-described binding sites that are considered important (FIG. 8A). We called this construct −1918-Δ-1302 (FIG. 8B). We transfected the respective constructs to CHO-DG44 cells. As shown in FIG. 8A, we found that the 100 bp upstream of the transcription start site of RPL32 was essential for its influence on the human β-actin promoter. No colonies were formed by the construct containing the −1918-Δ-1302 promoter construct. Surprisingly, deletions of either 5' or 3' sites (−1918 to 504 and −691 to 1302, respectively; corresponding to positions 1 to 2423 and 1236 to 3220 of SEQ ID NO:1, respectively) resulted in increased colony numbers, in comparison with the full length RPL32 promoter fragment (−1918 to 1302, i.e. entire SEQ ID NO:1). In either case, the average d2EGFP values were very similar. However, upon further shortening (−1918 to 94 and −137 to 1302, respectively; corresponding to positions 1 to 2013 and 1782 to 3220 of SEQ ID NO:1, respectively) resulted in strongly decreased colony numbers (FIG. 8B). In these colonies d2EGFP values were also strongly decreased. These results would argue that deleting either a large portion of the 5' or 3' site has no effect, but this was not the case.

With such a construct (−691 to 504; corresponding to positions 1236 to 2423 of SEQ ID NO:1) both colony numbers and d2EGFP values were decreased (FIG. 8B), indicating that a larger portion of the RPL32 promoter region is required to obtain the full beneficial effects.

We conclude that a functional RPL32 promoter is essential for its beneficial influence on the human β-actin promoter and that the orientation of the RPL32 promoter must be that RPL32 transcription is in the same direction as that of the human β-actin promoter. Finally, pinpointing the exact region within the RPL32 promoter that is responsible for the positive effects of the promoter on colony formation and gene expression levels is complex.

5. Example 5

The RPL32 Promoter Operates Under Serum Free Suspension Transfection and Culturing Conditions Above described experiments were all performed in adherent cell cultures. It is, however, possible that promoters and gene activity enhancing elements operate different under serum free culturing conditions. We, therefore, transfected control and RPL32 containing constructs under serum free conditions to suspension CHO-DG44-S suspension cells (Gibco/Invitrogen Catalogue No. 12609-012) and cultured them likewise under serum free suspension conditions.

5.1 Results

Wild-type CHO DG44-S suspension cells were grown in serum free CD-DG44 medium supplemented with 200 mM glutamine, pluronic acid, and anti-clumping agent at 37° C./8% $CO_2$ on a shaker (130 rpm). Cells were passaged every 2-3 days. Cells were transfected (nucleofected) with an Amaxa Nucleofector, using the Nucleofection-kit Amaxa V, as described by the manufacturer. In brief, culture medium was supplemented with ITS and medium was equilibrated in the incubator to adjust pH. For each nucleofection, $1 \cdot 10^6$ wild-type DG44-S cells, grown to a density between $7 \cdot 10^5$ and $1 \cdot 10^6$ and with a viability of >90%, were centrifuged in a swing out centrifuge (900 rpm, 5 min.). Cell pellets were dissolved in 100 μl nucleofector solution and 5 μg DNA (in a volume of 5 μl) was added. Samples were transferred to a cuvette and electroporation in the Amaxa Nucleofector was performed (using program U-30), after which the samples were transferred to the equilibrated culture medium (in 6-well culture plates). After 5-6 hours, the cells were transferred to T25 (suspension) culture flask, in a total volume of 5 ml. After 48 hours, selection was started by adding 50 μg/ml Zeocin to the culture medium. Medium was refreshed every 2-3 days. During the next three weeks, the viability of the cells was monitored and, if applicable, d2EGFP expression levels were determined.

Three weeks after nucleofection, 5000-10000 viable cells/ml were poured in Semi Solid medium (Genetix), to form subclones. After ten days, colonies were isolated and transferred to 96-wells culture plates in 100 μl culture medium. After another week, cells could be transferred to 24-wells plates (in 0.5 ml medium). At this point in time, either FACS or ELISA assays determined the d2EGFP, EPO or antibody expression levels. Selected subclones were propagated to grow in T25 culture flasks (in 5 ml medium). After another 2-3 weeks, d2EGFP, EPO or antibody expression levels were measured for the second time.

The following constructs were driven by the

Figure 9:
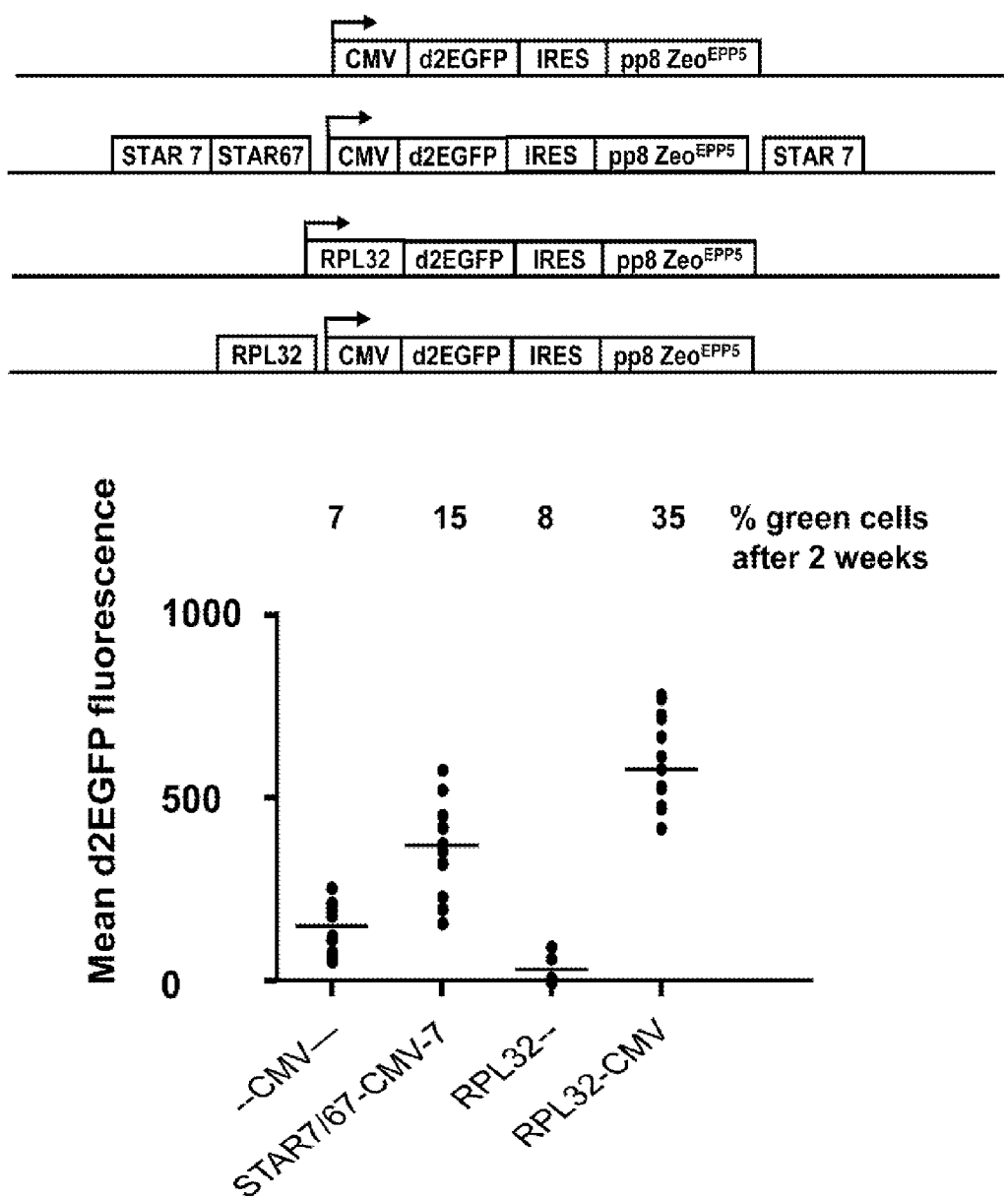
FIG. 9: Influence on protein expression of RPL32 combinations in suspension growing cells.

1 CMV promoter alone, without any flanking element,

2 CMV promoter, but flanked by STARs 7/67/7,

3 RPL32 promoter alone, without any further elements,

4 CMV promoter, with the RPL32 promoter placed upstream,

As selection marker, the pp8Zeo$^{EPP5}$ mutation was taken (FIG. 9). As measure for the effectiveness of the different constructs, we determined the percentage of green fluorescent cells within the suspension population, two weeks after nucleofection. As shown in FIG. 9, after two weeks, the CMV promoter alone gave displayed only 7% green cells, and so did the RPL32 as promoter alone (8%). Only when elements were added to the construct, the percentage green cells two weeks after nucleofection increased significantly. With flanking STAR elements the percentage rose to 15%, with the RPL32 promoter, placed upstream of the CMV promoter to 35% (FIG. 9).

When the d2EGFP was determined, three weeks after nucleofection, we noticed that the average d2EGFP expression values closely followed the percentage green cells after two weeks. The d2EGFP expression values were low with the CMV or RPL32 promoter alone (FIG. 9), increasing with flanking STAR elements, and highest with the RPL32 promoter. These results show that also in suspension growing CHO-DG44-S cells, the RPL32 promoter is an effective tool to increase the number of gene expressing cells as well as the d2EGFP expression values.

Figure 10:
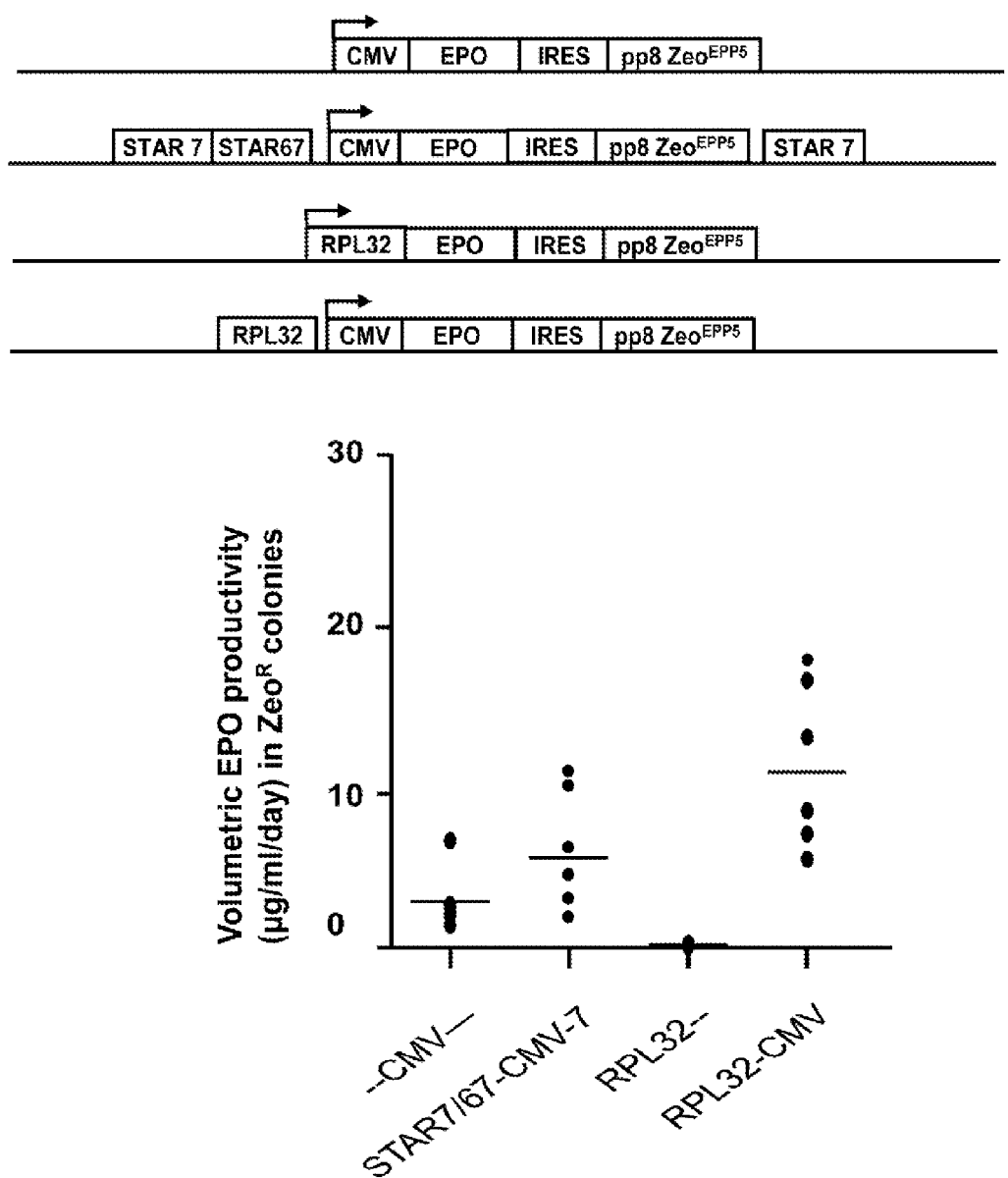
FIG. 10: Influence on protein expression of RPL32 combinations in suspension growing cells.

We also determined the effects of the RPL32 promoter in similar constructs, but with EPO as reporter gene, instead of the d2EGFP gene. We therefore replaced the d2EGFP gene with the EPO gene. In this case we could not use the % producing cell as measure for effectiveness of nucleofection, and, we therefore directly determined per construct the volumetric EPO production (in μg/ml/day) in six clones, isolated from semi solid medium. As shown in FIG. 10, we found the same trend with EPO expression as with d2EGFP expression. The CMV and RPL32 promoters alone were very ineffective. EPO expression levels increased with STAR elements, but were highest with the RPL32 promoter upstream of the CMV promoter. We conclude that also with a secreted protein such as EPO, the RPL32 promoter placed upstream of another promoter is an effective means to enhance the activity of this second promoter.

The invention claimed is:

1. A nucleic acid construct for expression of a gene product of interest in a host cell comprising:
   (a) a nucleic acid fragment comprising a promoter sequence having at least 90% sequence identity to nucleotide residues 1236 to 2423 of SEQ ID NO:1 and 95% sequence identity to nucleotide residues 1782 to 1921 therein
   (b) an expression cassette comprising a promoter operably linked to a nucleotide sequence encoding the gene product of interest, and
   wherein the fragment is linked to the expression cassette in an orientation so that transcription from the promoter in the fragment is in the same direction as transcription from the promoter in the expression cassette, and
   (c) a nucleotide sequence encoding a selectable marker functional in a eukaryotic host cell;
   wherein, when the fragment is upstream and operably linked to the expression cassette having the nucleotide sequence of SEQ ID NO: 2 and in an orientation so that transcription from the promoter in the fragment is in the same direction as transcription from the promoter in SEQ ID NO: 2, the fragment produces at least 50% of number of colonies obtained with the same expression cassette when flanked with STARs 7 and 67 upstream of the expression cassette and STAR 7 downstream of the expression cassette, when tested under the conditions of Example 1.

2. The nucleic acid construct according to claim 1, wherein the nucleic acid fragment comprises a sequence having at least 90% sequence identity to nucleotide residues 1236 to 3220, 1 to 2423, or 1 to 3220 of SEQ ID NO:1, and 95% sequence identity to nucleotide residues 1782 to 1921 therein.

3. The nucleic acid construct according to claim 1, wherein the nucleic acid fragment is located upstream, downstream, or both upstream and downstream of the expression cassette.

4. The nucleic acid construct according to claim 3, wherein the nucleic acid fragment is located both upstream and downstream of the expression cassette, and wherein the upstream fragment is different from the downstream fragment.

5. The nucleic acid construct according to claim 1, wherein the selectable marker provides resistance against lethal or growth-inhibitory effects of a selection agent selected from the group consisting of zeocin, puromycin, blasticidin, hygromycin, neomycin, methotrexate, methionine sulphoximine and kanamycin.

6. The nucleic acid construct according to claim 1, wherein the nucleotide sequence encoding the selectable marker is at least one of:
   (a) a nucleotide sequence having a mutation in the start codon that decreases the translation initiation efficiency of the selectable marker polypeptide in a eukaryotic host cell;
   (b) a nucleotide sequence that is part of a multicistronic transcription unit comprising:
      (i) the nucleotide sequence encoding the selectable marker; and,
      (ii) a functional open reading frame comprising in a 5' to 3' direction a translation initiation codon, at least one amino acid codon and a translation stop codon; wherein the stop codon of functional open reading frame is present between 0 and 250 nucleotides upstream of the separate translation initiation codon of the nucleotide sequence encoding the selectable marker, and wherein the sequence separating the stop codon of functional open reading frame and the separate translation initiation codon of the nucleotide sequence encoding the selectable marker is devoid of translation initiation codons; and, (c) a nucleotide sequence encoding a selectable marker polypeptide comprising a mutation encoding at least one amino acid change that reduces the activity of the selectable marker polypeptide compared to its wild-type counterpart.

7. The nucleic acid construct according to claim 1, wherein the nucleotide sequence encoding a selectable marker and the nucleotide sequence encoding a gene product of interest are comprised in a single multicistronic transcription unit, wherein the multicistronic transcription unit is operably linked to the promoter and to a transcription termination sequence downstream of the multicistronic transcription unit.

8. The nucleic acid construct according to claim 1, wherein the promoter is a β-actin promoter, a CMV promoter, an SV40 promoter, an ubiquitin C promoter or an EF1-alpha promoter.

9. An expression vector comprising a nucleic acid construct according to claim 1.

10. A host cell comprising a nucleic acid construct according to claim 1.

11. The host cell according to claim 10, wherein the host cell is a plant cell or a mammalian cell.

12. The host cell according to claim 10, wherein the host cell is of a cell line.

13. The host cell according to claim 12, wherein the cell line is selected from the group consisting of a U-2 OS osteosarcoma, CHO, CHO-K1, CHO-DG44, CHO-DG44-S, CHO-DP12, CHO-DUKXBl1, HEK 293, HuNS-1 myeloma, WERI-Rb-1 retinoblastoma, BHK, Vero, non-secreting mouse myeloma Sp2/0-Ag 14, non-secreting mouse myeloma NSO and NCI-H295R adrenal gland carcinoma cell line.

14. The nucleic acid construct according to claim 1, wherein the nucleic acid fragment comprises a sequence having at least 95% sequence identity to nucleotide residues 1236 to 2423 of SEQ ID NO:1.

15. A nucleic acid construct for expression of a gene product of interest in a host cell comprising:
(a) a nucleic acid fragment comprising a promoter sequence having at least 90% sequence identity to nucleotide residues 1236 to 2423 of SEQ ID NO:1 and 95% sequence identity to nucleotide residues 1782 to 1921 therein,
(b) an expression cassette comprising a promoter operably linked to a nucleotide sequence encoding the gene product of interest, wherein the fragment is linked to the expression cassette in an orientation so that transcription from the promoter in the fragment is in the same direction as transcription from the promoter in the expression cassette, and
(c) a nucleotide sequence encoding a selectable marker functional in a eukaryotic host cell.

16. The nucleic acid construct according to claim 15, wherein the nucleic acid fragment comprises a sequence having at least 95% sequence identity to nucleotide residues 1236 to 2423 of SEQ ID NO:1.

17. The nucleic acid construct according to claim 1, wherein the nucleic acid fragment comprising a sequence having at least 95% sequence identity to nucleotide residues 1236 to 2423 of SEQ ID NO:1 and sequence identity to nucleotide residues 1782 to 1921 therein.

18. The nucleic acid construct according to claim 15, wherein the nucleic acid fragment comprises nucleotide residues 1236 to 2423 of SEQ ID NO:1.

19. A method of generating a host cell for expression of a gene product of interest, comprising:
(a) introducing into a plurality of host cells a nucleic acid construct of claim 1;
(b) culturing the plurality of host cells obtained in (a) under conditions selecting for expression of a selectable marker polypeptide; and,
(c) selecting at least one host cell expressing the selectable marker polypeptide for expression of the gene product of interest.

20. The method of expressing a gene product of interest, comprising culturing a host cell of claim 10, and expressing the gene product of interest from the nucleic acid construct.

21. The method of claim 20, further comprising recovering the gene product of interest.

* * * * *